United States Patent
Seo et al.

(10) Patent No.: US 12,127,479 B2
(45) Date of Patent: Oct. 22, 2024

(54) LIGHT-EMITTING ELEMENT, LIGHT-EMITTING DEVICE, ELECTRONIC DEVICE, LIGHTING DEVICE, AND ORGANIC COMPOUND

(71) Applicant: Semiconductor Energy Laboratory Co., Ltd., Kanagawa-ken (JP)

(72) Inventors: Satoshi Seo, Kanagawa (JP); Takao Hamada, Kanagawa (JP); Tatsuyoshi Takahashi, Kanagawa (JP); Yasushi Kitano, Kanagawa (JP); Hiroki Suzuki, Kanagawa (JP); Hideko Inoue, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 18/381,846

(22) Filed: Oct. 19, 2023

(65) Prior Publication Data
US 2024/0147852 A1    May 2, 2024

Related U.S. Application Data

(63) Continuation of application No. 18/094,154, filed on Jan. 6, 2023, now Pat. No. 11,800,799, which is a (Continued)

(30) Foreign Application Priority Data
Jul. 25, 2014   (JP) ................ 2014-151493

(51) Int. Cl.
*H01L 51/50* (2006.01)
*C07D 403/14* (2006.01)
(Continued)

(52) U.S. Cl.
CPC ....... *H10K 85/6572* (2023.02); *C07D 403/14* (2013.01); *H10K 85/342* (2023.02); (Continued)

(58) Field of Classification Search
None
See application file for complete search history.

(56) References Cited

U.S. PATENT DOCUMENTS
7,175,922 B2   2/2007 Jarikov et al.
7,183,010 B2   2/2007 Jarikov
(Continued)

FOREIGN PATENT DOCUMENTS
CN   102190653 A   9/2011
CN   102655222 A   9/2012
(Continued)

OTHER PUBLICATIONS
Yersin.H et al., Highly Efficient OLEDs with Phosphorescent Materials, 2008, pp. 1-97,283-309, Wiley-VCH Verlag GmbH & Co.
(Continued)

*Primary Examiner* — Gregory D Clark
(74) *Attorney, Agent, or Firm* — Husch Blackwell LLP

(57) ABSTRACT

To provide a light-emitting element with an improved reliability, a light-emitting element with a high current efficiency (or a high quantum efficiency), and a novel dibenzo[f,h]quinoxaline derivative that is favorably used in a light-emitting element which is one embodiment of the present invention. A light-emitting element includes an EL layer between an anode and a cathode. The EL layer includes a light-emitting layer; the light-emitting layer contains a first organic compound having an electron-transport property and a hole-transport property, a second organic compound having a hole-transport property, and a light-emitting substance; the combination of the first organic compound and
(Continued)

the second organic compound forms an exciplex; the HOMO level of the first organic compound is lower than the HOMO level of the second organic compound; and a difference between the HOMO level of the first organic compound and the HOMO level of the second organic compound is less than or equal to 0.4 eV.

18 Claims, 38 Drawing Sheets

Related U.S. Application Data continuation of application No. 16/570,062, filed on Sep. 13, 2019, now Pat. No. 11,552,256, which is a continuation of application No. 15/988,152, filed on May 24, 2018, now Pat. No. 10,418,565, which is a continuation of application No. 14/807,426, filed on Jul. 23, 2015, now Pat. No. 9,985,221.

(51) Int. Cl.
  *H10K 85/60* (2023.01)
  *H10K 85/30* (2023.01)
(52) U.S. Cl.
  CPC ......... *H10K 85/633* (2023.02); *H10K 85/636* (2023.02); *Y02P 20/582* (2015.11)

(56) References Cited

U.S. PATENT DOCUMENTS

| | | | |
|---|---|---|---|
| 7,332,857 B2 | 2/2008 | Seo et al. |
| 7,597,967 B2 | 10/2009 | Kondakova et al. |
| 7,906,226 B2 | 3/2011 | Matsuura et al. |
| 7,993,760 B2 | 8/2011 | Komori et al. |
| 8,034,465 B2 | 10/2011 | Liao et al. |
| 8,105,701 B2 | 1/2012 | Matsuura et al. |
| 8,274,214 B2 | 9/2012 | Ikeda et al. |
| 8,470,455 B2 | 6/2013 | Matsuura et al. |
| 8,652,654 B2 | 2/2014 | Inoue et al. |
| 8,653,553 B2 | 2/2014 | Yamazaki et al. |
| 8,736,157 B2 | 5/2014 | Seo et al. |
| 8,828,561 B2 | 9/2014 | Kim et al. |
| 8,853,680 B2 | 10/2014 | Yamazaki et al. |
| 8,865,323 B2 | 10/2014 | Inoue et al. |
| 8,877,352 B2 | 11/2014 | Inoue et al. |
| 8,889,858 B2 | 11/2014 | Inoue et al. |
| 8,940,414 B2 | 1/2015 | Inoue et al. |
| 8,963,127 B2 | 2/2015 | Pieh et al. |
| 8,969,854 B2 | 3/2015 | Takemura et al. |
| 8,981,355 B2 | 3/2015 | Seo |
| 8,993,129 B2 | 3/2015 | Endo et al. |
| 8,994,043 B2 | 3/2015 | Seo et al. |
| 8,994,263 B2 | 3/2015 | Shitagaki et al. |
| 9,054,317 B2 | 6/2015 | Monkman et al. |
| 9,056,856 B2 | 6/2015 | Kadoma et al. |
| 9,059,414 B2 | 6/2015 | Inoue et al. |
| 9,067,916 B2 | 6/2015 | Osaka et al. |
| 9,076,976 B2 | 7/2015 | Seo et al. |
| 9,079,879 B2 | 7/2015 | Kadoma et al. |
| 9,099,617 B2 | 8/2015 | Yamazaki et al. |
| 9,123,907 B2 | 9/2015 | Seo et al. |
| 9,142,710 B2 | 9/2015 | Seo et al. |
| 9,159,942 B2 | 10/2015 | Seo et al. |
| 9,175,213 B2 | 11/2015 | Seo et al. |
| 9,178,158 B2 | 11/2015 | Kitano et al. |
| 9,276,228 B2 | 3/2016 | Seo et al. |
| 9,309,458 B2 | 4/2016 | Inoue et al. |
| 9,356,250 B2 | 5/2016 | Ohsawa et al. |
| 9,394,280 B2 | 7/2016 | Seo et al. |
| 9,450,193 B2 | 9/2016 | Kim et al. |
| 9,478,755 B2 | 10/2016 | Kim et al. |
| 9,502,666 B2 | 11/2016 | Nakayama et al. |
| 9,525,149 B2 | 12/2016 | Seo et al. |
| 9,537,106 B2 | 1/2017 | Kwong et al. |
| 9,559,313 B2 | 1/2017 | Seo et al. |
| 9,559,324 B2 | 1/2017 | Seo et al. |
| 9,604,928 B2 | 3/2017 | Shitagaki et al. |
| 9,663,711 B2 | 5/2017 | Takeda et al. |
| 9,786,860 B2 | 10/2017 | Yamazaki et al. |
| 9,899,608 B2 | 2/2018 | Kadoma et al. |
| 9,929,350 B2 | 3/2018 | Yamazaki et al. |
| 9,947,885 B2 | 4/2018 | Seo et al. |
| 9,985,221 B2 | 5/2018 | Seo et al. |
| 10,121,984 B2 | 11/2018 | Seo et al. |
| 10,141,524 B2 | 11/2018 | Inoue et al. |
| 10,193,077 B2 | 1/2019 | Inoue et al. |
| 10,361,390 B2 | 7/2019 | Yamazaki et al. |
| 10,418,565 B2 | 9/2019 | Seo et al. |
| 10,439,150 B2 | 10/2019 | Nakayama et al. |
| 10,505,120 B2 | 12/2019 | Yamazaki et al. |
| 10,505,132 B2 | 12/2019 | Seo et al. |
| 10,573,829 B2 | 2/2020 | Shitagaki et al. |
| 10,586,934 B2 | 3/2020 | Shitagaki et al. |
| 10,593,895 B2 | 3/2020 | Shitagaki et al. |
| 10,644,254 B2 | 5/2020 | Seo et al. |
| 10,665,808 B2 | 5/2020 | Seo et al. |
| 10,734,594 B2 | 8/2020 | Seo et al. |
| 2003/0175553 A1 | 9/2003 | Thompson et al. |
| 2005/0048310 A1 | 3/2005 | Cocchi et al. |
| 2005/0221116 A1 | 10/2005 | Cocchi et al. |
| 2006/0134464 A1 | 6/2006 | Nariyuki |
| 2007/0090756 A1 | 4/2007 | Okada et al. |
| 2008/0265760 A1 | 10/2008 | Aratani et al. |
| 2009/0160323 A1 | 6/2009 | Nomura et al. |
| 2010/0289406 A1 | 11/2010 | Ma et al. |
| 2011/0210316 A1 | 9/2011 | Kadoma et al. |
| 2011/0278555 A1 | 11/2011 | Inoue et al. |
| 2012/0205632 A1 | 8/2012 | Shitagaki et al. |
| 2012/0205687 A1 | 8/2012 | Yamazaki et al. |
| 2012/0211736 A1 | 8/2012 | Kim et al. |
| 2012/0217486 A1 | 8/2012 | Takemura et al. |
| 2012/0217487 A1 | 8/2012 | Yamazaki et al. |
| 2012/0242219 A1 | 9/2012 | Seo et al. |
| 2012/0305909 A1 | 12/2012 | Seo et al. |
| 2013/0048971 A1 | 2/2013 | Kitano et al. |
| 2013/0082591 A1 | 4/2013 | Seo et al. |
| 2013/0140549 A1 | 6/2013 | Xia et al. |
| 2013/0277655 A1 | 10/2013 | Seo et al. |
| 2014/0034929 A1 | 2/2014 | Hamada et al. |
| 2014/0084274 A1 | 3/2014 | Yamazaki et al. |
| 2014/0332758 A1 | 11/2014 | Kwong et al. |
| 2015/0021579 A1 | 1/2015 | Yamazaki et al. |
| 2015/0069352 A1 | 3/2015 | Kim et al. |
| 2015/0228912 A1 | 8/2015 | Inoue et al. |
| 2016/0315270 A1 | 10/2016 | Seo et al. |
| 2016/0372688 A1 | 12/2016 | Seo et al. |
| 2017/0012207 A1 | 1/2017 | Seo et al. |
| 2017/0025630 A1* | 1/2017 | Seo ...................... H10K 59/38 |
| 2017/0092878 A1 | 3/2017 | Seo et al. |
| 2017/0179411 A1 | 6/2017 | Shitagaki et al. |
| 2017/0253796 A1 | 9/2017 | Takeda et al. |
| 2017/0271610 A1 | 9/2017 | Takahashi |
| 2018/0009751 A1 | 1/2018 | Nomura et al. |
| 2018/0269410 A1 | 9/2018 | Shitagaki et al. |
| 2019/0040009 A1 | 2/2019 | Nomura et al. |
| 2019/0157577 A1 | 5/2019 | Shitagaki et al. |
| 2019/0341568 A1 | 11/2019 | Yamazaki et al. |
| 2020/0111966 A1 | 4/2020 | Yamazaki et al. |
| 2020/0194692 A1 | 6/2020 | Shitagaki et al. |
| 2020/0280011 A1 | 9/2020 | Seo et al. |
| 2020/0350503 A1 | 11/2020 | Seo et al. |

FOREIGN PATENT DOCUMENTS

| | | |
|---|---|---|
| CN | 102884156 A | 1/2013 |
| CN | 103081155 A | 5/2013 |
| CN | 103374043 A | 10/2013 |
| CN | 103518270 A | 1/2014 |
| CN | 103579530 A | 2/2014 |
| EP | 1202608 A | 5/2002 |
| EP | 2363398 A | 9/2011 |
| EP | 2415769 A | 2/2012 |

(56) References Cited

FOREIGN PATENT DOCUMENTS

| | | |
|---|---|---|
| EP | 2423209 A | 2/2012 |
| EP | 2497811 A | 9/2012 |
| EP | 3460024 A | 3/2019 |
| JP | 2007-189001 A | 7/2007 |
| JP | 2008-053556 A | 3/2008 |
| JP | 2008-288344 A | 11/2008 |
| JP | 2009-298767 A | 12/2009 |
| JP | 2010-182699 A | 8/2010 |
| JP | 2011-201869 A | 10/2011 |
| JP | 2012-186461 A | 9/2012 |
| JP | 2012-195572 A | 10/2012 |
| JP | 2012-195573 A | 10/2012 |
| JP | 2012-227524 A | 11/2012 |
| JP | 2013-510141 | 3/2013 |
| JP | 2013-065842 A | 4/2013 |
| JP | 2013-131743 A | 7/2013 |
| JP | 2013-199473 A | 10/2013 |
| JP | 2013-219347 A | 10/2013 |
| JP | 2013-237662 A | 11/2013 |
| JP | 2013-239704 A | 11/2013 |
| JP | 2014-007156 A | 1/2014 |
| JP | 2014-029971 A | 2/2014 |
| JP | 2014-056814 A | 3/2014 |
| JP | 2014-078703 A | 5/2014 |
| JP | 2014-218499 A | 11/2014 |
| JP | 2016-032108 A | 3/2016 |
| JP | 2017-022378 A | 1/2017 |
| JP | 2017-168800 A | 9/2017 |
| JP | 2017-168803 A | 9/2017 |
| KR | 2011-0099173 A | 9/2011 |
| KR | 2014-0133435 A | 11/2014 |
| TW | 201321374 | 6/2013 |
| TW | I731046 | 6/2021 |
| WO | WO-2011/132683 | 10/2011 |
| WO | WO-2011/132684 | 10/2011 |
| WO | WO-2011/162162 | 12/2011 |
| WO | WO-2012/111579 | 8/2012 |
| WO | WO-2012/137693 | 10/2012 |
| WO | WO-2013/027846 | 2/2013 |
| WO | WO-2013/137089 | 9/2013 |
| WO | WO-2013/157506 | 10/2013 |
| WO | WO-2014/046221 | 3/2014 |
| WO | WO-2016/203350 | 12/2016 |
| WO | WO-2017/006222 | 1/2017 |
| WO | WO-2017/013534 | 1/2017 |
| WO | WO-2017/158475 | 9/2017 |

OTHER PUBLICATIONS

Tokito.S et al., "Improvement in performance by doping", Organic EL Display, Aug. 20, 2004, pp. 67-99, Ohmsha.

Jeon.W et al., "Ideal host and guest system in phosphorescent OLEDs", Organic Electronics, 2009, vol. 10, pp. 240-246, Elsevier.

Su.S et al., "RGB Phosphorescent Organic Light-Emitting Diodes by Using Host Materials with Heterocyclic Cores:Effect of Nitrogen Atom Orientations", Chem. Mater. (Chemistry of Materials), 2011, vol. 23, No. 2, pp. 274-284.

Rausch.A et al., "Matrix Effects on the Triplet State of the OLED Emitter Ir(4,6-dFppy)2(pic)(FIrpic): Investigations by High-Resolution Optical Spectroscopy", Inorg. Chem. (Inorganic Chemistry), 2009, vol. 48, No. 5, pp. 1928-1937.

Gong.X et al., "Phosphorescence from iridium complexes doped into polymer blends", J. Appl. Phys. (Journal of Applied Physics), Feb. 1, 2004, vol. 95, No. 3, pp. 948-953.

Zhao.Q et al., "Synthesis and Photophysical, Electrochemical, and Electrophosphorescent Properties of a Series of Iridium(III) Complexes Based on Quinoline Derivatives and Different β-Diketonate Ligands", Organometallics, Jun. 14, 2006, vol. 25, No. 15, pp. 3631-3638.

Hino.Y et al., "Red Phosphorescent Organic Light-Emitting Diodes Using Mixture System of Small-Molecule and Polymer Host", Jpn. J. Appl. Phys. (Japanese Journal of Applied Physics), Apr. 21, 2005, vol. 44, No. 4B, pp. 2790-2794, The Japan Society of Applied Physics.

Tsuboyama.A et al., "Homoleptic Cyclometalated Iridium Complexes with Highly Efficient Red Phosphorescence and Application to Organic Light-Emitting Diode", J. Am. Chem. Soc. (Journal of the American Chemical Society), 2003, vol. 125, No. 42, p. 12971-12979.

Kondakova.M et al., "High-efficiency, low-voltage phosphorescent organic light-emitting diode devices with mixed host", J. Appl. Phys. (Journal of Applied Physics), Nov. 4, 2008, vol. 104, pp. 094501-1- 094501-17.

Chen.F et al., "Triplet Exciton Confinement in Phosphorescent Polymer Light-Emitting Diodes", Appl. Phys. Lett. (Applied Physics Letters), Feb. 17, 2003, vol. 82, No. 7, pp. 1006-1008.

Lee.J et al., "Stabilizing the efficiency of phosphorescent organic light-emitting diodes", SPIE Newsroom, Apr. 21, 2008, pp. 1-3.

Tokito.S et al., "Confinement of Triplet Energy on Phosphorescent Molecules for Highly-Efficient Organic Blue-Light-Emitting Devices", Appl. Phys. Lett. (Applied Physics Letters), Jul. 21, 2003, vol. 83, No. 3, pp. 569-571.

Endo.A et al., "Efficient Up-Conversion of Triplet Excitons Into a Singlet State and Its Application for Organic Light Emitting Diodes", Appl. Phys. Lett. (Applied Physics Letters), Feb. 24, 2011, vol. 98, No. 8, pp. 083302-1-083302-3.

Itano.K et al., "Exciplex formation at the organic solid-state interface: Yellow emission in organic light-emitting diodes using green-fluorescent tris(8-quinolinolato)aluminum and hole-transporting molecular materials with low ionization potentials", Appl. Phys. Lett. (Applied Physics Letters), Feb. 9, 1998, vol. 72, No. 6, pp. 636-638.

Park.Y et al., "Efficient triplet harvesting by fluorescent molecules through exciplexes for high efficiency organic light-emitting diodes", Appl. Phys. Lett. (Applied Physics Letters), Apr. 18, 2013, vol. 102, No. 15, pp. 153306-1-153306-5.

Chinese Office Action (Application No. 201510443903.1) Dated Mar. 22, 2018.

Wang.H et al., "Current efficiency in organic light-emitting diodes with a hole-injection layer", Appl. Phys. Lett. (Applied Physics Letters), Sep. 1, 2008, vol. 93, No. 9, Pp. 093306-1-093306-3.

Taiwanese Office Action (Application No. 104123410) Dated Nov. 27, 2018.

German Office Action (Application No. 102015213426.1) Dated Apr. 1, 2020.

Chinese Office Action (Application No. 201910360982.8) Dated Nov. 25, 2020.

Taiwanese Office Action (Application No. 110108994) Dated Mar. 18, 2022.

Kim.S et al., "Relationship between host energy levels and device performances of phosphorescent organic light-emitting diodes with triplet mixed host emitting structure", Appl. Phys. Lett. (Applied Physics Letters), Aug. 23, 2007, vol. 91, No. 8, Pp. 083511-1-083511-3.

Effect of exciplex forming co-hosts on the performance of phosphorescent dye doped organic light emitting diodes, Feb. 1, 2013.

Jeon.W et al., "High efficiency red phosphorescent organic light-emitting diodes with single layer structure", Organic Electronics, Oct. 22, 2009, vol. 11, No. 2, pp. 179-183.

Chang.C et al., "A dicarbazole-triazine hybrid bipolar host material for highly efficient green phosphorescent OLEDs", J. Mater. Chem. (Journal of Materials Chemistry), Jan. 23, 2012, vol. 22, No. 9, pp. 3832-3838.

Wei.X et al., "Design of Efficient Exciplex Emitters by Decreasing the Energy Gap Between the Local Excited Triplet (3LE) State of the Acceptor and the Charge Transfer (CT) States of the Exciplex", Frontiers in Chemistry, Apr. 9, 2019, vol. 7, pp. 1-9.

German Office Action (Application No. 102015017428.2) Dated Sep. 4, 2024.

* cited by examiner

LIGHT-EMITTING ELEMENT, LIGHT-EMITTING DEVICE, ELECTRONIC DEVICE, LIGHTING DEVICE, AND ORGANIC COMPOUND

BACKGROUND OF THE INVENTION

This application is a continuation of U.S. application Ser. No. 18/094,154, filed on Jan. 6, 2023 which is a continuation of U.S. application Ser. No. 16/570,062, filed on Sep. 13, 2019 (now U.S. Pat. No. 11,552,256 issued Jan. 10, 2023) which is a continuation of U.S. application Ser. No. 15/988,152, filed on May 24, 2018 (now U.S. Pat. No. 10,418,565 issued Sep. 17, 2019) which is a continuation of U.S. application Ser. No. 14/807,426, filed on Jul. 23, 2015 (now U.S. Pat. No. 9,985,221 issued May 29, 2018) which are all incorporated herein by reference.

FIELD OF THE INVENTION

The present invention relates to an object, a method, or a manufacturing method. The present invention also relates to a process, a machine, manufacture, or a composition of matter. In particular, one embodiment of the present invention relates to a light-emitting element, a light-emitting device, an electronic device, a lighting device, a driving method thereof, or a manufacturing method thereof. One embodiment of the present invention further relates to an organic compound which can be used in a light-emitting element, a light-emitting device, an electronic device, and a lighting device.

DESCRIPTION OF THE RELATED ART

A light-emitting element using an organic compound as a luminous body, which has features such as thinness, lightness, high-speed response, and DC drive at low voltage, is expected to be used in a next-generation flat panel display. In particular, a display device in which light-emitting elements are arranged in a matrix is considered to have advantages in a wide viewing angle and excellent visibility over a conventional liquid crystal display device.

The light emission mechanism of a light-emitting element is said to be as follows: when a voltage is applied between a pair of electrodes with an EL layer including a luminous body provided therebetween, electrons injected from a cathode and holes injected from an anode recombine in the light emission center of the EL layer to form molecular excitons, and energy is released and light is emitted when the molecular excitons return to the ground state. Singlet excitation and triplet excitation are known as excited states, and it is thought that light emission can be achieved through either of the excited states.

In order to improve element characteristics of such a light-emitting element, improvement of an element structure, development of a material, and the like have been actively carried out (see, for example, Patent Document 1).

REFERENCE

Patent Document

[Patent Document 1] Japanese Published Patent Application No. 2010-182699

SUMMARY OF THE INVENTION

When light-emitting elements are developed, one of important points for commercialization is to improve the reliability of the elements. In order to improve the reliability of the elements, an element structure is needed, which can control the carrier balance and improve the recombination probability of carriers in an EL layer of a light-emitting element. Therefore, it is an object to provide a highly reliable light-emitting element in the following way: an EL layer is made to have a desired structure so that carriers are transferred efficiently in a light-emitting layer. A high current efficiency (or a high quantum efficiency) is also important to decrease the amount of current needed for driving the element and to improve the reliability.

In one embodiment of the present invention, a light-emitting element with an improved reliability is provided. In addition, a light-emitting element with a high current efficiency (or a high quantum efficiency) is provided. Furthermore, a novel organic compound that is favorably used in a light-emitting element which is one embodiment of the present invention is provided. In another embodiment of the present invention, a light-emitting element, a light-emitting device, an electronic device, or a lighting device with a high emission efficiency and a high reliability, in which the above organic compound is used as an EL material, is provided. In another embodiment of the present invention, a novel material is provided. In another embodiment of the present invention, a novel light-emitting element and a novel light-emitting device are provided. Note that the descriptions of these objects do not disturb the existence of other objects. In one embodiment of the present invention, there is no need to achieve all the objects. Other objects will be apparent from and can be derived from the descriptions of the specification, the drawings, the claims, and the like.

One embodiment of the present invention is a light-emitting element including an EL layer between an anode and a cathode. The EL layer includes a light-emitting layer; the light-emitting layer contains a first organic compound having an electron-transport property and a hole-transport property, a second organic compound having a hole-transport property, and a light-emitting substance; the combination of the first organic compound and the second organic compound forms an exciplex; the HOMO level of the first organic compound is lower than the HOMO level of the second organic compound; and a difference between the HOMO level of the first organic compound and the HOMO level of the second organic compound is less than or equal to 0.4 eV.

Another embodiment of the present invention is a light-emitting element including an EL layer between an anode and a cathode. The EL layer includes a light-emitting layer; the light-emitting layer contains a first organic compound having an electron-transport property and a hole-transport property, a second organic compound having a hole-transport property, and a light-emitting substance; the combination of the first organic compound and the second organic compound forms an exciplex; the first organic compound includes a 6-membered nitrogen-containing heteroaromatic ring and a carbazole skeleton and does not include a triarylamine skeleton; and the second organic compound includes a triarylamine skeleton.

Another embodiment of the present invention is a light-emitting element including an EL layer between an anode and a cathode. The EL layer includes a light-emitting layer; the light-emitting layer contains a first organic compound having an electron-transport property and a hole-transport property, a second organic compound having a hole-transport property, and a light-emitting substance; the combination of the first organic compound and the second organic compound forms an exciplex; the first organic compound includes a 6-membered nitrogen-containing heteroaromatic ring and a bicarbazole skeleton and does not include a triarylamine skeleton; and the second organic compound includes a triarylamine skeleton.

In the above structure, the bicarbazole skeleton is a 3,3'-bicarbazole skeleton or a 2,3'-bicarbazole skeleton.

In each of the above structures, the light-emitting substance is a phosphorescent compound.

In each of the above structures, the EL layer includes a hole-transport layer; the hole-transport layer is in contact with the light-emitting layer and contains a third organic compound having a hole-transport property; and the HOMO level of the third organic compound is lower than the HOMO level of the second organic compound.

In each of the above structures, the first organic compound is represented by the following general formula (G0).

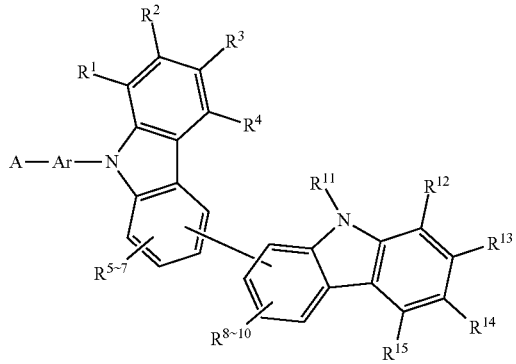

(G0)

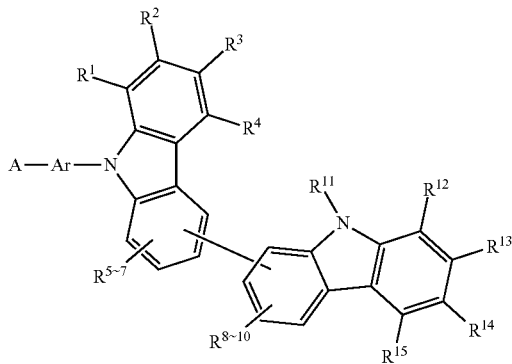

(G0)

In the formula, A represents a dibenzo[f,h]quinoxalinyl group; $R^1$ to $R^{15}$ represent independently hydrogen, a substituted or unsubstituted alkyl group having 1 to 6 carbon atoms, a substituted or unsubstituted cycloalkyl group having 5 to 7 carbon atoms, or a substituted or unsubstituted aryl group having 6 to 13 carbon atoms; and Ar represents a substituted or unsubstituted arylene group having 6 to 25 carbon atoms or a single bond. Preferably, an arylene group in Ar does not include an anthracenylene group.

Another embodiment of the present invention is an organic compound represented by the following general formula (G1).

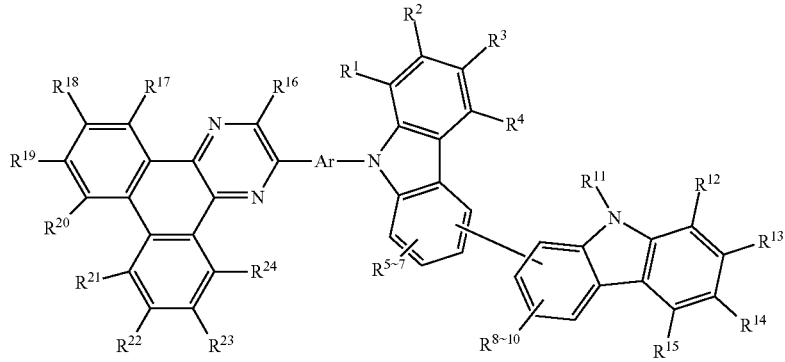

(G1)

In the formula, A represents a dibenzo[f,h]quinoxalinyl group; $R^1$ to $R^{15}$ represent independently hydrogen, a substituted or unsubstituted alkyl group having 1 to 6 carbon atoms, a substituted or unsubstituted cycloalkyl group having 5 to 7 carbon atoms, or a substituted or unsubstituted aryl group having 6 to 13 carbon atoms; and Ar represents a substituted or unsubstituted arylene group having 6 to 25 carbon atoms or a single bond. Preferably, an arylene group in Ar does not include an anthracenylene group.

Another embodiment of the present invention is an organic compound represented by the following general formula (G0).

In the formula, $R^1$ to $R^{24}$ represent independently hydrogen, a substituted or unsubstituted alkyl group having 1 to 6 carbon atoms, a substituted or unsubstituted cycloalkyl group having 5 to 7 carbon atoms, or a substituted or unsubstituted aryl group having 6 to 13 carbon atoms; and Ar represents a substituted or unsubstituted arylene group having 6 to 25 carbon atoms or a single bond. Preferably, an arylene group in Ar does not include an anthracenylene group.

Another embodiment of the present invention is an organic compound represented by the following general formula (G2).

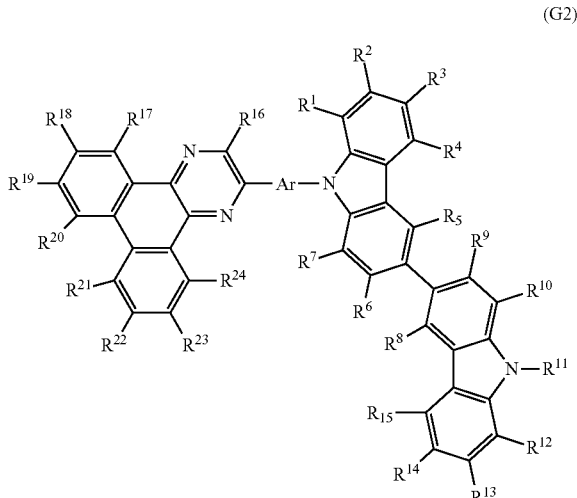

(G2)

In the formula, $R^1$ to $R^{24}$ represent independently hydrogen, a substituted or unsubstituted alkyl group having 1 to 6 carbon atoms, a substituted or unsubstituted cycloalkyl group having 5 to 7 carbon atoms, or a substituted or unsubstituted aryl group having 6 to 13 carbon atoms; and Ar represents a substituted or unsubstituted arylene group having 6 to 25 carbon atoms or a single bond. Preferably, an arylene group in Ar does not include an anthracenylene group.

Another embodiment of the present invention is an organic compound represented by the following general formula (G3).

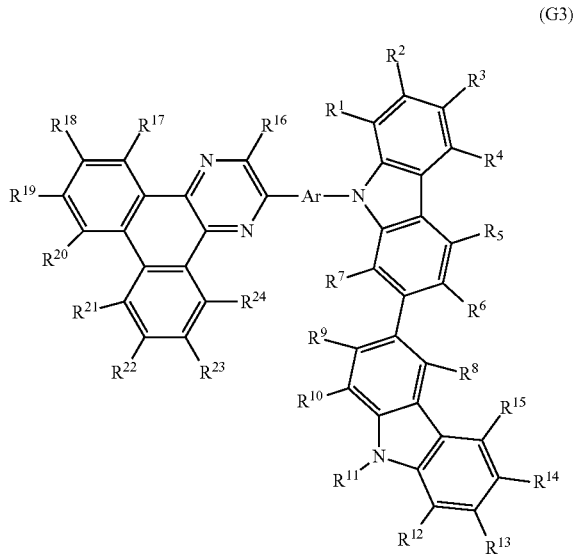

(G3)

In the formula, $R^1$ to $R^{24}$ represent independently hydrogen, a substituted or unsubstituted alkyl group having 1 to 6 carbon atoms, a substituted or unsubstituted cycloalkyl group having 5 to 7 carbon atoms, or a substituted or unsubstituted aryl group having 6 to 13 carbon atoms; and Ar represents a substituted or unsubstituted arylene group having 6 to 25 carbon atoms or a single bond. Preferably, an arylene group in Ar does not include an anthracenylene group.

Examples of the alkyl group having 1 to 6 carbon atoms in each of the above general formula (G0), general formula (G2), and general formula (G3) include a methyl group, an ethyl group, a propyl group, an isopropyl group, a butyl group, an isobutyl group, a sec-butyl group, a tert-butyl group, a pentyl group, an isopentyl group, and a hexyl group. Examples of the cycloalkyl group having 5 to 7 carbon atoms include a cyclopentyl group, a cyclohexyl group, and a cycloheptyl group. Examples of the aryl group having 6 to 13 carbon atoms include a phenyl group, a tolyl group, a xylyl group, a biphenyl group, an indenyl group, a naphthyl group, and a fluorenyl group. Examples of the arylene group having 6 to 25 carbon atoms in Ar include a 1,2-, 1,3-, and 1,4-phenylene groups, a 2,6-, 3,5-, and 2,4-toluylene groups, a 4,6-dimethylbenzene-1,3-diyl group, a 2,4,6-trimethylbenzene-1,3-diyl group, a 2,3,5,6-tetramethylbenzene-1,4-diyl group, a 3,3'-, 3,4'-, and 4,4'-biphenylene groups, a 1,1': 3', 1"-terbenzene-3,3"-diyl group, a 1,1': 4',1"-terbenzene-3,3"-diyl group, a 1,1': 4',1"-terbenzene-4,4"-diyl group, a 1,1': 3',1": 3",1'''-quaterbenzene-3,3'''-diyl group, a 1,1': 3',1": 4",1'''-quaterbenzene-3,4'''-diyl group, a 1,1': 4',1": 4",1'''-quaterbenzene-4,4'''-diyl group, a 1,4-, 1,5-, 2,6-, and 2,7-naphthylene groups, a 2,7-fluorenylene group, a 9,9-dimethyl-2,7-fluorenylene group, a 9,9-diphenyl-2,7-fluorenylene group, a 9,9-dimethyl-1,4-fluorenylene group, a spiro-9,9'-bifluorene-2,7-diyl group, a 9,10-dihydro-2,7-phenanthrenylene group, a 2,7-phenanthrenylene group, a 3,6-phenanthrenylene group, a 9,10-phenanthrenylene group, a 2,7-triphenylenylene group, a 3,6-triphenylenylene group, a 2,8-benzo[a]phenanthrenylene group, a 2,9-benzo[a]phenanthrenylene group, and a 5,8-benzo[c]phenanthrenylene group.

The alkyl group having 1 to 6 carbon atoms, the cycloalkyl group having 5 to 7 carbon atoms, the aryl group having 6 to 13 carbon atoms, and the arylene group having 6 to 25 carbon atoms may each have a substituent. Examples of the substituent preferably include alkyl groups each having 1 to 6 carbon atoms, such as a methyl group, an ethyl group, a propyl group, an isopropyl group, a butyl group, an isobutyl group, a sec-butyl group, a tert-butyl group, a pentyl group, an isopentyl group, and a hexyl group; cycloalkyl groups each having 5 to 7 carbon atoms, such as a cyclopentyl group, a cyclohexyl group, and a cycloheptyl group; and aryl groups each having 6 to 13 carbon atoms, which form a ring, such as a phenyl group, a tolyl group, a xylyl group, a biphenyl group, an indenyl group, a naphthyl group, a fluorenyl group, and a 9,9-dimethylfluorenyl group.

Another embodiment of the present invention is a light-emitting element containing the organic compound represented by any of the above general formulae (G0) to (G3).

Another embodiment of the present invention is a light-emitting device including the light-emitting element having any of the above structures and a housing.

One embodiment of the present invention includes, in its category, in addition to a light-emitting device including a light-emitting element, an electronic device including the light-emitting element or the light-emitting device (specifically, an electronic device including the light-emitting element or the light-emitting device and a connection terminal or an operation key) and a lighting device including the light-emitting element or the light-emitting device (specifically, a lighting device including the light-emitting element or the light-emitting device and a housing). A light-emitting device in this specification refers to an image display device or a light source (e.g., a lighting device). A light-emitting device also includes, in its category, all of a module in which a light-emitting device is connected to a connector such as a flexible printed circuit (FPC) or a tape carrier package (TCP), a module in which a printed wiring board is provided on the tip of a TCP, and a module in which an integrated circuit (IC) is directly mounted on a light-emitting element by a chip on glass (COG) method.

In accordance with one embodiment of the present invention, a novel dibenzo[f,h]quinoxaline derivative can be provided. In accordance with one embodiment of the present invention, a light-emitting element, a light-emitting device, an electronic device, or a lighting device with a high emission efficiency and a high reliability, in which the above dibenzo[f,h]quinoxaline derivative is used as an EL material, can be provided. In accordance with one embodiment of the present invention, a novel material can be provided. In accordance with another embodiment of the present invention, a novel light-emitting element and a novel light-emitting device can be provided. Note that the descriptions of these effects do not disturb the existence of other effects. One embodiment of the present invention does not necessarily achieve all the effects listed above. Other effects will be apparent from and can be derived from the descriptions of the specification, the drawings, the claims, and the like.

DETAILED DESCRIPTION OF THE INVENTION

Hereinafter, embodiments of the present invention will be described in detail with reference to the accompanying drawings. Note that the present invention is not limited to the following description, and the modes and details thereof can be modified in various ways without departing from the spirit and scope of the present invention. Accordingly, the present invention should not be interpreted as being limited to the content of the embodiments below.

Note that the terms "film" and "layer" can be interchanged with each other depending on the case or circumstances. For example, the term "conductive layer" can be changed into the term "conductive film" in some cases. Also, the term "insulating film" can be changed into the term "insulating layer" in some cases.

Embodiment 1

In this embodiment, a light-emitting element which is one embodiment of the present invention will be described.

In a light-emitting element described in this embodiment, an EL layer including a light-emitting layer is provided between a pair of electrodes (a first electrode (anode) and a second electrode (cathode)), and the EL layer includes a hole-injection layer, a hole-transport layer, an electron-transport layer, an electron-injection layer, and the like in addition to the light-emitting layer.

When a voltage is applied to the light-emitting element, holes injected from the first electrode side and electrons injected from the second electrode side recombine in the light-emitting layer; with energy generated by the recombination, a light-emitting substance contained in the light-emitting layer emits light.

Figure 1:
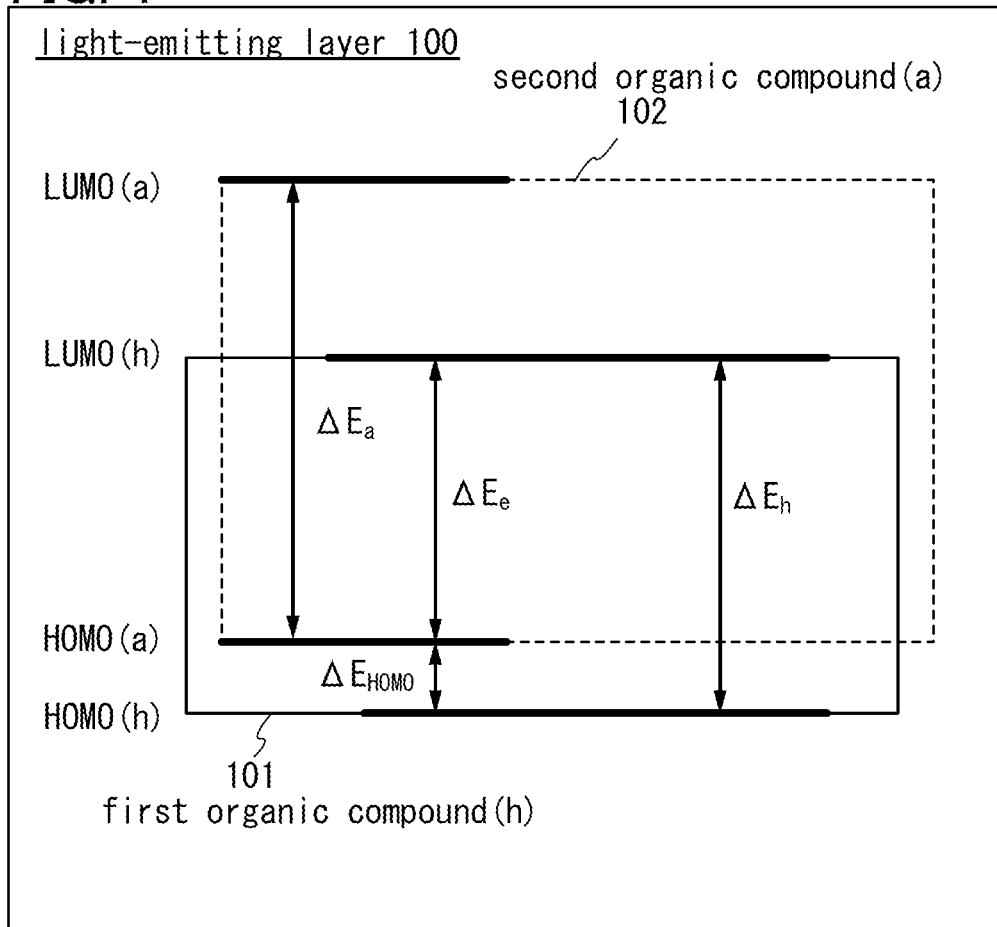
FIG. 1 schematically shows a light-emitting layer of a light-emitting element.

As shown in FIG. 1, a light-emitting layer 100 contains a first organic compound (h) 101 having an electron-transport property and a hole-transport property, a second organic compound (a) 102 having a hole-transport property, and a light-emitting substance (not shown in the drawing). Note that the combination of the first organic compound (h) 101 and the second organic compound (a) 102 forms an excited complex (also referred to as an exciplex). That is, the lowest unoccupied molecular orbital (LUMO) level of the first organic compound (h) 101 is at least lower than the LUMO level of the second organic compound (a) 102, and the highest occupied molecular orbital (HOMO) level of the first organic compound (h) 101 is at least lower than the HOMO level of the second organic compound (a) 102. Accordingly, as shown in the drawing, the excitation energy of the generated exciplex is influenced by an energy difference (i.e., $\Delta E_e$ in the drawing) between the LUMO level of the first organic compound (h) 101 (LUMO (h)) and the HOMO level of the second organic compound (a) 102 (HOMO (a)).

Such a light-emitting layer 100 enables energy transfer utilizing an overlap between the emission spectrum of the exciplex and the absorption spectrum of the light-emitting substance (guest material), leading to a high energy transfer efficiency; thus, a light-emitting element with a high external quantum efficiency can be achieved. Furthermore, in order that the exciplex is electrically excited, electric energy (i.e., voltage) corresponding to $\Delta E_e$ is needed. This energy $\Delta E_e$ is lower than energy $\Delta E_h$ needed for electrically exciting the first organic compound (h) 101 and energy $\Delta E_a$ needed for electrically exciting the second organic compound (a) 102. In other words, with such a light-emitting layer 100, drive voltage (emission start voltage) of the light-emitting element can be reduced.

Without using the first organic compound (h) 101 and the second organic compound (a) 102, one kind of organic compound having a HOMO-LUMO gap corresponding to $\Delta E_e$ may be used for a light-emitting layer, whereby drive voltage (emission start voltage) that is low as in the case of the light-emitting layer 100 can be achieved. However, in the case of using one kind of organic compound, triplet excitation energy is significantly decreased as compared to singlet excitation energy; thus, it is difficult to achieve light emission by transfer of triplet excitation energy to a light-emitting substance (guest material). On the other hand, in the exciplex, singlet excitation energy and triplet excitation energy are located at substantially the same level, which makes it possible to transfer both singlet excitation energy and triplet excitation energy to the light-emitting substance. As a result, as well as the above-described effect of reduction in voltage, a higher efficiency can be achieved in the light-emitting element. A detailed mechanism of the higher efficiency will be described below.

When the light-emitting substance is a phosphorescent compound, singlet excitation energy and triplet excitation energy of the exciplex are both transferred to the triplet excited state of the phosphorescent compound, and light emission from the triplet excited state (i.e., phosphorescence) is achieved; thus, the light-emitting substance is most preferably a phosphorescent compound in order to achieve a higher efficiency.

When the light-emitting substance is a thermally activated delayed fluorescent compound, singlet excitation energy of the exciplex is transferred to the singlet excited state of the light-emitting substance, and light emission from the singlet excited state (i.e., fluorescence) is achieved. In addition, triplet excitation energy of the exciplex is transferred to the triplet excited state of the light-emitting substance; however, reverse intersystem crossing from part of or the entire triplet excited state to the singlet excited state of the light-emitting substance occurs due to thermal activation, from which fluorescence is achieved, leading to a higher efficiency.

When the light-emitting substance is a fluorescent compound, singlet excitation energy of the exciplex is transferred to the singlet excited state of the light-emitting substance, and light emission from the singlet excited state (i.e., fluorescence) is achieved. On the other hand, triplet excitation energy of the exciplex is transferred to the triplet excited state of the light-emitting substance and thermally deactivated; thus, it seems that a higher efficiency cannot be achieved. However, the exciplex that is an energy donor has a small difference between singlet excitation energy and triplet excitation energy and thus emits thermally activated delayed fluorescence from itself. In other words, in the exciplex, reverse intersystem crossing from part of or the entire triplet excited state to the singlet excited state occurs, so that the proportion of singlet excitons is higher than that in the normal situation. The proportion of singlet excitons in the exciplex that is an energy donor is high, and singlet excitation energy of the exciplex is transferred to the singlet excited state of the light-emitting substance, whereby the emission efficiency is high even in the case of using a fluorescent compound as a light-emitting substance. This phenomenon is also one feature of the present invention.

As described above, a light-emitting element in which an exciplex serves as an energy donor in a light-emitting layer is effective in all the cases where a phosphorescent compound, a thermally activated delayed fluorescent compound, and a fluorescent compound are used as a light-emitting substance; however, there is a problem in controlling a light-emitting region.

As already described above, in order to form the exciplex of the first organic compound (h) 101 and the second organic compound (a) 102, the following condition is needed: the LUMO level of the first organic compound (h) 101 (LUMO (h)) is at least lower than the LUMO level of the second organic compound (a) 102 (LUMO(a)), and the HOMO level of the first organic compound (h) 101 (HOMO(h)) is at least lower than the HOMO level of the second organic compound (a) 102 (HOMO(a)). In particular, in a conventional light-emitting element in which an exciplex serves as an energy donor in the light-emitting layer 100, an energy difference $\Delta E_{HOMO}$ between the HOMO level of the first organic compound (h) 101 (HOMO(h)) and the HOMO level of the second organic compound (a) 102 (HOMO(a)) is made very large, thereby forming an exciplex. For example, 2-[3'-(dibenzothiophen-4-yl)biphenyl-3-yl] dibenzo[f,h]quinoxaline (abbreviation: 2mDBTBPDBq-II) is used as the first organic compound (h) 101 and N-(1,1'-biphenyl-4-yl)-9,9-dimethyl-N-[4-(9-phenyl-9H-carbazol-3-yl)phenyl]-9H-fluor en-2-amine (abbreviation: PCBBiF) is used as the second organic compound (a) 102; in that case, the HOMO level of the first organic compound (h) 101 (HOMO(h)) is −6.22 eV, the HOMO level of the second organic compound (a) 102 (HOMO(a)) is −5.36 eV, and $\Delta E_{HOMO}$ is as large as 0.86 eV.

When a difference ($\Delta E_{HOMO}$) between the HOMO level of the first organic compound (h) 101 (HOMO(h)) and the HOMO level of the second organic compound (a) 102 (HOMO(a)) is large as described above, the carrier balance tends to be significantly changed depending on the amount of the second organic compound (a) 102 in the light-emitting layer 100. That is, a too small amount of the second organic compound (a) 102 results in excessive electrons, and a light-emitting region exists mainly on the anode side; on the other hand, the amount of the second organic compound (a) 102, which only slightly exceeds the optimal amount, results in excessive holes, and the holes are transported to the cathode side. In such a device with a narrow margin, even when the first organic compound (h) 101 and the second organic compound (a) 102 are mixed at an optimized ratio, a small change in the carrier balance through long-time driving leads to a reduction in recombination efficiency and a lower luminance. When $\Delta E_{HOMO}$ is large, holes are stored in the second organic compound (a) 102, so that the recombination region in the light-emitting layer 100 is narrowed. In the case where the recombination region in the light-emitting layer 100 is wide, the entire light-emitting layer 100 can be used and the reliability is high.

In the light-emitting element, an electron-injection property is decreased owing to deterioration of an electron-injection electrode (cathode) or the like, which might cause the recombination region to be shifted to the cathode side through long-time driving. In that case, the average distance for transporting holes to the recombination region gets longer; thus, when the light-emitting layer 100 has a poor hole-transport property, the resistance of the light-emitting element is increased. In other words, in the case where the element is driven at constant current, drive voltage is significantly increased over time. When the difference ($\Delta E_{HOMO}$) between the HOMO level of the first organic compound (h) (HOMO(h)) and the HOMO level of the second organic compound (a) (HOMO(a)) is large, holes are transported with difficulty through the light-emitting layer 100; thus, an increase in drive voltage over time is very problematic.

One embodiment of the present invention solves a problem in the above-described light-emitting element in which the exciplex serves as an energy donor in the light-emitting layer 100. That is, a light-emitting element which is one embodiment of the present invention includes an EL layer between an anode and a cathode. The EL layer includes the light-emitting layer 100; the light-emitting layer 100 contains the first organic compound (h) 101 having an electron-transport property and a hole-transport property, the second organic compound (a) 102 having a hole-transport property, and the light-emitting substance; the combination of the first organic compound (h) 101 and the second organic compound (a) 102 forms an exciplex; the HOMO level of the first organic compound (h) (HOMO(h)) is lower than the HOMO level of the second organic compound (a) (HOMO (a)); and a difference between the HOMO level of the first organic compound (h) (HOMO(h)) and the HOMO level of the second organic compound (a) (HOMO(a)) is less than or equal to 0.4 eV.

With such a structure, holes are injected not only into the second organic compound (a) 102 but also partly into the first organic compound (h) 101. As a result, holes are unlikely to be stored in the second organic compound (a) 102; thus, a light-emitting element can be obtained, in which the carrier balance can be easily maintained and the recombination region in the light-emitting layer 100 is wide. In addition, an increase in voltage through long-time driving (driving at constant current) can be suppressed. In the above case, in part of the light-emitting layer 100, recombination is caused in the first organic compound (h) 101, which leads to the formation of an excited state of the first organic compound, but this is rapidly converted into an exciplex; thus, a higher efficiency can be achieved by using the exciplex. Furthermore, since holes are mainly injected into the second organic compound (a) 102, the effect of reducing drive voltage (emission start voltage) can be maintained.

In this way, $\Delta E_{HOMO}$ is set to be less than or equal to 0.4 eV (and greater than 0 eV), and the combination of the first organic compound (h) 101 and the second organic compound (a) 102 forms an exciplex, whereby the above-described problem can be solved. Since holes are injected not only into the second organic compound (a) 102 but also into the first organic compound (h) 101, $\Delta E_{HOMO}$ is preferably less than or equal to 0.3 eV.

Compounds that are suitable to achieve the above concept are as follows. Preferably, the first organic compound (h) 101 includes a 6-membered nitrogen-containing heteroaromatic ring and a carbazole skeleton and does not include a triarylamine skeleton. That is, a compound having an electron-transport property due to including a 6-membered nitrogen-containing heteroaromatic ring and a moderate hole-transport property due to including a carbazole skeleton and not including a triarylamine skeleton is preferably used. The second organic compound (a) 102 has a hole-transport property and preferably includes a triarylamine skeleton so that the HOMO level of the second organic compound (a) 102 is higher than that of the first organic compound (h) 101.

A compound including a triarylamine skeleton has, in many cases, a HOMO level of about −5.5 eV, or higher than or equal to −5.5 eV, on the basis of a cyclic voltammetry (CV) measurement, whereas the HOMO level of a simple 9-phenylcarbazole is −5.88 eV, so that the difference between the HOMO level of the compound including a triarylamine skeleton and that of 9-phenylcarbazole is greater than or equal to 0.4 eV in many cases. Therefore, in one embodiment of the present invention, the first organic compound (h) 101 preferably includes a bicarbazole skeleton as a carbazole skeleton, because the HOMO level of bicarbazole is higher than that of 9-phenylcarbazole. In particular, in one embodiment of the present invention, a 3,3'-bicarbazole skeleton or a 2,3'-bicarbazole skeleton is preferably introduced into the first organic compound (h) 101 because its HOMO level becomes about −5.6 eV to −5.7 eV.

Examples of the 6-membered nitrogen-containing heteroaromatic ring include, as well as pyridine, diazine such as pyrazine, pyrimidine, or pyridazine, triazine, and tetrazine. Such a 6-membered nitrogen-containing heteroaromatic ring may further be condensed with a benzene ring or the like. Examples of the 6-membered nitrogen-containing heteroaromatic ring condensed with a benzene ring include quinoline, isoquinoline, and dibenzo[f,h]quinoline. Furthermore, naphthyridine typified by quinoxaline, quinazoline, and phthalazine, dibenzo[f,h]quinoxaline, dibenzo[f,h]quinazoline, and the like can also be used.

Figure 2:
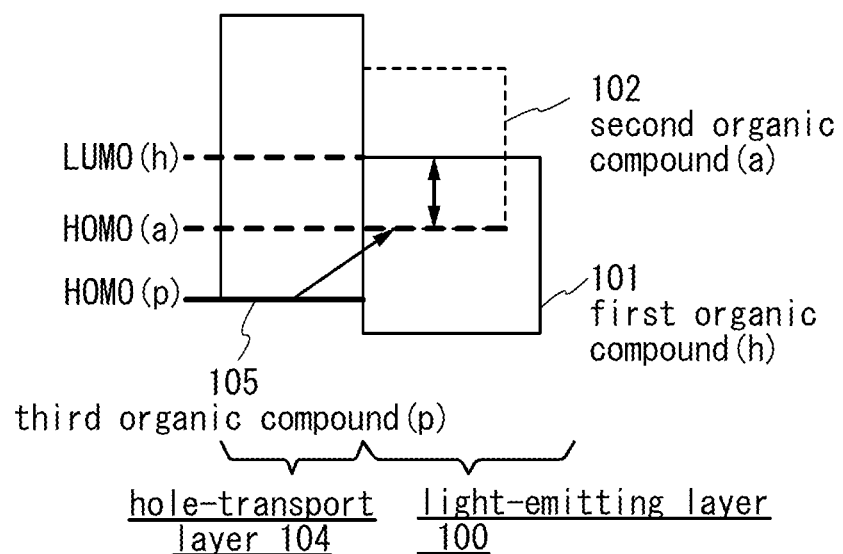
FIG. 2 schematically shows a light-emitting layer of a light-emitting element.

In one embodiment of the present invention, holes are preferably injected and transported not only to the second organic compound (a) 102 but also to the first organic compound (h) 101, as described above. Therefore, in order to improve a hole-injection property with respect to both the first organic compound (h) 101 and the second organic compound (a) 102 in the light-emitting layer 100, preferably, a third organic compound (p) 105 having a hole-transport property is used for a hole-transport layer 104 in contact with the light-emitting layer 100, and the HOMO level of the third organic compound (p) 105 (HOMO(p)) is set to be lower than the HOMO level of the second organic compound (a) 102 (HOMO(a)), as shown in FIG. 2. In particular, the third organic compound (p) 105 is preferably selected so that the HOMO level of the third organic compound (p) 105 (HOMO(p)) can be a level between the HOMO level of the second organic compound (a) 102 (HOMO(a)) and the HOMO level of the first organic compound (h) 101 (HOMO (h)).

Figure 3A:
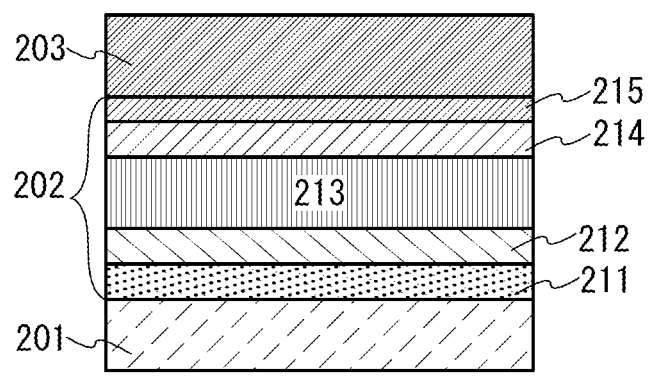
FIGS. 3A and 3B each illustrate the structure of a light-emitting element.

A specific example of a light-emitting element which is one embodiment of the present invention and has the above structure will be described below with reference to FIGS. 3A and 3B.

For a first electrode (anode) 201 and a second electrode (cathode) 203, a metal, an alloy, an electrically conductive compound, a mixture thereof, and the like can be used. Specifically, indium oxide-tin oxide (indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti) can be used. In addition, an element belonging to Group 1 or 2 of the periodic table, for example, an alkali metal such as lithium (Li) or cesium (Cs), an alkaline earth metal such as calcium (Ca) or strontium (Sr), magnesium (Mg), an alloy containing such an element (MgAg, AlLi), a rare earth metal such as europium (Eu) or ytterbium (Yb), an alloy containing such an element, graphene, and the like can be used. The first electrode (anode) 201 and the second electrode (cathode) 203 can be formed by, for example, a sputtering method, an evaporation method (including a vacuum evaporation method), or the like.

A hole-injection layer 211 injects holes into a light-emitting layer 213 through a hole-transport layer 212 having a high hole-transport property and contains a substance having a high hole-transport property (also referred as a hole-transport compound) and an acceptor substance. The hole-injection layer 211 contains a substance having a high hole-transport property and an acceptor substance, so that electrons are extracted from the substance having a high hole-transport property by the acceptor substance to generate holes and the holes are injected into the light-emitting layer 213 through the hole-transport layer 212. The hole-transport layer 212 is formed using a substance having a high hole-transport property.

Examples of the substance having a high hole-transport property which is used for the hole-injection layer 211 and the hole-transport layer 212 include aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4''-tris(carbazol-9-yl)triphenylamine (abbreviation: TCTA), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); and 3-[N-(1-naphthyl)-N-(9-phenylcarbazol-3-yl)amino]-9-phenylcarbazole (abbreviation: PCzPCN1). Alternatively, the following carbazole derivatives and the like can be used: 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthracenyl)phenyl]-9H-Carbazole (abbreviation: CzPA). The substances described here are mainly substances each having a hole mobility of higher than or equal to $1 \times 10^{-6}$ cm$^2$/Vs. Note that other substances may also be used as long as the substances have higher hole-transport properties than electron-transport properties.

Alternatively, high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacryla mide] (abbreviation: PTPDMA), and poly[N,N'-bis(4-butylphenyl)-N,N'-bis(phenyl)benzidine] (abbreviation: Poly-TPD) can be used.

Examples of the acceptor substance that is used for the hole-injection layer 211 include oxides of metals belonging to Groups 4 to 8 of the periodic table. Specifically, molybdenum oxide is particularly preferable.

The light-emitting layer 213 is a layer containing a light-emitting substance. When the light-emitting layer 213 has the structure shown in FIG. 1, the light-emitting layer 213 contains a first organic compound having an electron-transport property and a hole-transport property, which will be described later, a second organic compound having a hole-transport property as described above, and a light-emitting substance. The combination of the first organic compound and the second organic compound forms an exciplex (also referred to as an excited complex) at the time of recombination of carriers (electrons and holes) in the light-emitting layer. When the exciplex is formed in the light-emitting layer, the fluorescence spectrum of the first organic compound and that of the second organic compound are converted into the emission spectrum of the exciplex which is located on a longer wavelength side. Moreover, when the first organic compound and the second organic compound are selected in such a manner that the emission spectrum of the exciplex largely overlaps with the absorption spectrum of a guest material, energy transfer from the singlet excited state can be maximized. Also in the case of the triplet excited state, energy transfer from the exciplex, not a host material, is assumed to occur.

Although the combination of the first organic compound and the second organic compound can be determined such that an exciplex is formed, a combination of a compound which is likely to accept electrons (a compound having an electron-trapping property) and a compound which is likely to accept holes (a compound having a hole-trapping property) is preferably employed. The first organic compound is preferably capable of trapping (or transporting) not only electrons but also holes and thus preferably includes a 6-membered nitrogen-containing heteroaromatic ring and a bicarbazole skeleton and does not include a triarylamine skeleton. For example, a compound represented by the following general formula (G0) is preferably used.

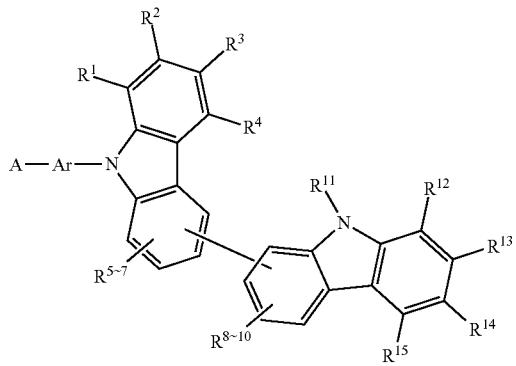

(G0)

In the formula, A represents a dibenzo[f,h]quinoxalinyl group; $R^1$ to $R^{15}$ represent independently hydrogen, a substituted or unsubstituted alkyl group having 1 to 6 carbon atoms, a substituted or unsubstituted cycloalkyl group having 5 to 7 carbon atoms, or a substituted or unsubstituted aryl group having 6 to 13 carbon atoms; and Ar represents a substituted or unsubstituted arylene group having 6 to 25 carbon atoms or a single bond. Preferably, an arylene group in Ar does not include an anthracenylene group.

When Ar includes an anthracenylene group, triplet excitation energy of the compound is largely decreased (to an energy of lower than or equal to 1.7 eV), in which case triplet excitation energy of the exciplex might be quenched. Therefore, preferably, an arylene group in Ar does not include an anthracenylene group.

Specifically, the compounds represented by the general formulae (G1) to (G3) are preferably used. More specifically, 2-{4-[3-(N-phenyl-9H-carbazol-3-yl)-9H-carbazol-9-yl]phenyl}dibenzo[f,h]quinoxaline (abbreviation: 2PCCzPDBq), 2-{3-[3-(N-phenyl-9H-carbazol-3-yl)-9H-carbazol-9-yl]phenyl}dibenzo[f,h]quinoxaline (abbreviation: 2mPCCzPDBq), 2-{4-[2-(N-phenyl-9H-carbazol-3-yl)-9H-carbazol-9-yl]phenyl}dibenzo[f,h]quinoxaline (abbreviation: 2PCCzPDBq-02), and 2-{3-[2-(N-phenyl-9H-carbazol-3-yl)-9H-carbazol-9-yl]phenyl}dibenzo[f,h]quinoxaline (abbreviation: 2mPCCzPDBq-02) can be used.

Examples of the compound which is likely to accept holes include compounds having triarylamine skeletons such as 4-phenyl-4'-(9-phenyl-9H-carbazol-3-yl)triphenylamine (abbreviation: PCBA1BP), 3-[N-(1-naphthyl)-N-(9-phenyl-carbazol-3-yl)amino]-9-phenylcarbazole (abbreviation: PCzPCN1), 4,4',4"-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N-bis(9-phenylcarbazol-3-yl)-N,N-diphenylbenzene-1,3-diamine (abbreviation: PCA2B), N-(9,9-dimethyl-2-N,N-diphenylamino-9H-fluoren-7-yl)diphenylamine (abbreviation: DPNF), N,N,N'-triphenyl-N,N,N'-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N-bis[4-(carbazol-9-yl)phenyl]-N,N-diphenyl-9,9-dimethylfluorene-2,7-diamine (abbreviation: YGA2F), 4,4'-bis[N-(3-methylphenyl)-N-phenylamino]biphenyl (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N'-phenyl-N-(9,9-dimethyl-9H-fl uoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N-(3-methylphenyl)-N-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), and 3,6-bis[N-(9-phenylcarbazol-3-yl)-N-phenylamino]-9-phenylcarbazole (abbreviation: PCzPCA2).

The first organic compound and the second organic compound are not limited to the above examples as long as the combination of the first organic compound and the second organic compound can form an exciplex, the emission spectrum of the exciplex overlaps with the absorption spectrum of the light-emitting substance, and the peak of the emission spectrum of the exciplex has a longer wavelength than the peak of the absorption spectrum of the light-emitting substance.

Note that in the case where the compound which is likely to accept electrons and the compound which is likely to accept holes are used as the first organic compound and the second organic compound, the carrier balance can be controlled by the mixture ratio of the compounds. Specifically, the ratio of the first organic compound to the second organic compound is preferably 1:9 to 9:1.

As the materials that can be used as the light-emitting substance and the emission center substance in the light-emitting layer 213, a light-emitting substance converting singlet excitation energy into light emission, a light-emitting substance converting triplet excitation energy into light emission, and the like can be used alone or in combination. Described below are examples of the light-emitting substance and the emission center substance.

As an example of the light-emitting substance converting singlet excitation energy into light emission, a substance which emits fluorescence (a fluorescent compound) can be given.

Examples of the substance which emits fluorescence include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N,N-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N,N-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N-tetrakis(4-methylphenyl)acenaphtho[1,2-a]fluoranthene-3,10-diamine (abbreviation: p-mPhAFD), {2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), {2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM).

Examples of the light-emitting substance converting triplet excitation energy into light emission include a substance which emits phosphorescence (a phosphorescent compound) and a thermally activated delayed fluorescent (TADF) material which emits thermally activated delayed fluorescence. Note that "delayed fluorescence" exhibited by the TADF material refers to light emission having the same spectrum as normal fluorescence and an extremely long lifetime. The lifetime is $10^{-6}$ seconds or longer, preferably $10^{-3}$ seconds or longer.

Examples of the substance which emits phosphorescence include bis{2-[3',5'-bis(trifluoromethyl)phenyl]pyridinato-N,$C^{2'}$}iridium(III) picolinate (abbreviation: Ir(CF$_3$ppy)$_2$(pic)), bis[2-(4',6'-difluorophenyl)pyridinato-N,$C^{2'}$]iridium(III) acetylacetonate (abbreviation: FIracac), tris(2-phenylpyridinato)iridium(III) (abbreviation: Ir(ppy)$_3$), bis(2-phenylpyridinato)iridium(III) acetylacetonate (abbreviation: Ir(ppy)$_2$(acac)), tris(acetylacetonato) (monophenanthroline)terbium(III) (abbreviation: Tb(acac)$_3$(Phen)), bis(benzo[h]quinolinato)iridium(III) acetylacetonate (abbreviation: Ir(bzq)$_2$(acac)), bis(2,4-diphenyl-1,3-oxazolato-N,$C^{2'}$)iridium(III) acetylacetonate (abbreviation: Ir(dpo)$_2$(acac)), bis{2-[4'-(perfluorophenyl)phenyl]pyridinato-N,$C^{2'}$}iridium(III) acetylacetonate (abbreviation: Ir(p-PF-ph)$_2$(acac)), bis(2-phenylbenzothiazolato-N,$C^{2'}$)iridium(III) acetylacetonate (abbreviation: Ir(bt)$_2$(acac)), bis[2-(2'-benzo[4,5-a]thienyl)pyridinato-N,$C^{3'}$]iridium(III) acetylacetonate (abbreviation: Ir(btp)$_2$(acac)), bis(1-phenylisoquinolinato-N,$C^{2'}$)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(3,5-dimethyl-2-phenylpyrazinato)iridium(III) (abbreviation: [Ir(mppr-Me)$_2$(acac)]), (acetylacetonato)bis(5-isopropyl-3-methyl-2-phenylpyrazinato)iridium(III) (abbreviation: [Ir(mppr-iPr)$_2$(acac)]), (acetylacetonato)bis(2,3,5-triphenylpyrazinato)iridium(III) (abbreviation: Ir(tppr)$_2$(acac)), bis(2,3,5-triphenylpyrazinato) (dipivaloylmethanato)iridium(III) (abbreviation: [Ir(tppr)$_2$(dpm)], (acetylacetonato)bis(6-tert-butyl-4-phenylpyrimidinato)iridium(III) (abbreviation: [Ir(tBuppm)$_2$(acac)]), (acetylacetonato)bis(4,6-diphenylpyrimidinato)iridium(III) (abbreviation: [Ir(dppm)$_2$(acac)]), 2,3,7,8,12,13,17,18-octaethyl-21H,23H-porphyrin platinum (II) (abbreviation: PtOEP), tris(1,3-diphenyl-1,3-propanedionato) (monophenanthroline)europium(III) (abbreviation: Eu(DBM)$_3$(Phen)), and tris[1-(2-thenoyl)-3,3,3-trifluoroacetonato] (monophenanthroline)europium(III) (abbreviation: Eu(TTA)$_3$(Phen)).

Examples of the TADF material include fullerene, a derivative thereof, an acridine derivative such as proflavine, and eosin. Other examples include a metal-containing porphyrin, such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$OEP). Alternatively, a heterocyclic compound including a π-electron rich heteroaromatic ring and a π-electron deficient heteroaromatic ring can be used, such as 2-(biphenyl-4-yl)-4,6-bis(12-phenylindolo[2,3-a]carbazol-11-yl)-1,3,5-triazine (PIC-TRZ). Note that a substance in which the π-electron rich heteroaromatic ring is directly bonded to the π-electron deficient heteroaromatic ring is particularly preferably used because both a donor property of the π-electron rich heteroaromatic ring and an acceptor property of the π-electron deficient heteroaromatic ring are increased and the energy difference between the S$_1$ level and the T$_1$ level becomes small.

Figure 3B:
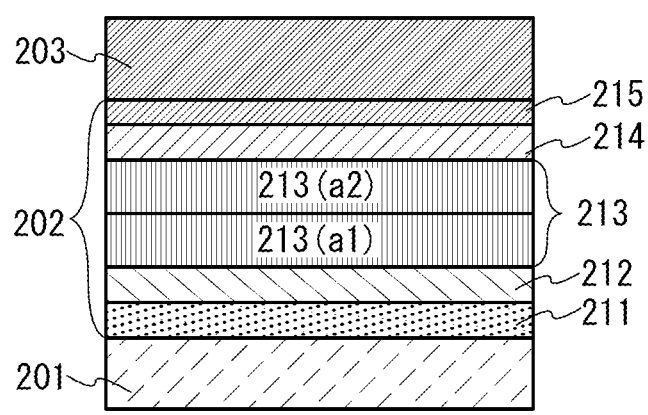

The light-emitting layer 213 may have a stacked structure as illustrated in FIG. 3B. In that case, each layer in the stacked structure emits light. For example, fluorescence is obtained from a first light-emitting layer 213 (a1), and phosphorescence is obtained from a second light-emitting layer 213 (a2) stacked over the first layer. Note that the stacking order may be reversed. It is preferable that light emission due to energy transfer from an exciplex to a dopant be obtained from the layer that emits phosphorescence. In the case where blue light emission is obtained from one of the first and second layers, orange or yellow light emission can be obtained from the other layer. Each layer may also contain plural kinds of dopants.

An electron-transport layer 214 is a layer containing a substance having a high electron-transport property (also referred to as an electron-transport compound). For the electron-transport layer 214, a metal complex such as tris (8-quinolinolato)aluminum(III) (abbreviation: Alq$_3$), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis [2-2(hydroxyphenyl)benzoxazolato]zinc(II) (abbreviation: Zn(BOX)$_2$), or bis[2-(2-hydroxyphenyl)benzothiazolato] zinc(II) (abbreviation: Zn(BTZ)$_2$) can be used. Alternatively, it is possible to use a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4'-tert-butylphenyl)-4-phenyl-5-(4"-biphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl) stilbene (abbreviation: BzOs). Further alternatively, it is possible to use a high molecular compound such as poly(2, 5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy). The substances mentioned here are mainly substances each having an electron mobility of higher than or equal to $1\times10^{-6}$ cm$^2$/Vs. Note that other substances may also be used for the electron-transport layer 214 as long as the substances have higher electron-transport properties than hole-transport properties.

The electron-transport layer 214 is not limited to a single layer and may have a stacked structure including two or more layers containing any of the above substances.

An electron-injection layer 215 is a layer containing a substance having a high electron-injection property. The electron-injection layer 215 can be formed using an alkali metal, an alkaline earth metal, or a compound thereof, such as lithium fluoride (LiF), cesium fluoride (CsF), calcium fluoride (CaF$_2$), or lithium oxide (LiO$_x$). Alternatively, a rare earth metal compound such as erbium fluoride (ErF$_3$) can be used. Alternatively, an electride may be used for the electron-injection layer 215. Examples of the electride include a substance in which electrons are added at high concentration to calcium oxide-aluminum oxide. Any of the substances for forming the electron-transport layer 214, which are given above, can also be used.

The electron-injection layer 215 may also be formed using a composite material in which an organic compound and an electron donor are mixed. The composite material is superior in an electron-injection property and an electron-transport property, because electrons are generated in the organic compound by the electron donor. In that case, as the organic compound, a material that can efficiently transport the produced electrons is preferably used; for example, any of the above-described substances that are used to form the electron-transport layer 214 (e.g., a metal complex or a heteroaromatic compound) can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, ytterbium, and the like can be given. Furthermore, an alkali metal oxide or an alkaline earth metal oxide is preferable, and for example, lithium oxide, calcium oxide, barium oxide, and the like can be given. Alternatively, Lewis base such as magnesium oxide can be used. An organic compound such as tetrathiafulvalene (abbreviation: TTF) can also be used.

Note that the hole-injection layer 211, the hole-transport layer 212, the light-emitting layer 213, the electron-transport layer 214, and the electron-injection layer 215, which are mentioned above, can each be formed by a method, such as an evaporation method (including a vacuum evaporation method), an inkjet method, or a coating method.

In the above-described light-emitting element, holes and electrons are recombined in the EL layer 202, whereby light is emitted. This emitted light is extracted out through the first electrode 201 and/or the second electrode 203. Therefore, the first electrode 201 and/or the second electrode 203 is an electrode having a light-transmitting property.

The light-emitting element described in this embodiment enables energy transfer utilizing an overlap between the emission spectrum of the exciplex and the absorption spectrum of a phosphorescent compound (guest material), leading to a high energy transfer efficiency; thus, a light-emitting element with a high external quantum efficiency can be achieved.

Note that the structure described in this embodiment can be combined as appropriate with any of the structures described in the other embodiments.

Embodiment 2

In this embodiment, a dibenzo[f,h]quinoxaline derivative which can be used in a light-emitting element and is one embodiment of the present invention will be described.

A dibenzo[f,h]quinoxaline derivative which is one embodiment of the present invention is represented by the following general formula (G0).

(G0)

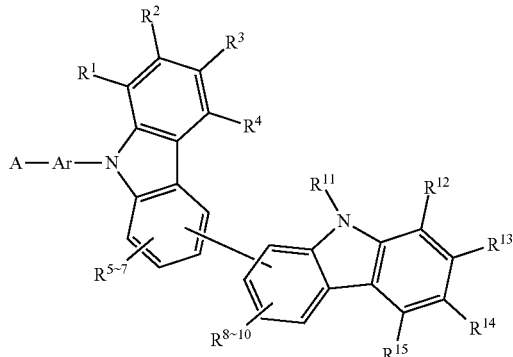

In the formula, A represents a dibenzo[f,h]quinoxalinyl group; $R^1$ to $R^{15}$ represent independently hydrogen, a substituted or unsubstituted alkyl group having 1 to 6 carbon atoms, a substituted or unsubstituted cycloalkyl group having 5 to 7 carbon atoms, or a substituted or unsubstituted aryl group having 6 to 13 carbon atoms; and Ar represents a substituted or unsubstituted arylene group having 6 to 25 carbon atoms or a single bond. Preferably, an arylene group in Ar does not include an anthracenylene group.

The dibenzo[f,h]quinoxaline derivative represented by the general formula (G0) can be synthesized by the following synthesis method. As shown in the following synthesis scheme (a), the dibenzo[f,h]quinoxaline derivative represented by the general formula (G0) can be obtained by reacting a halogen compound (A1) of a dibenzo[f,h]quinoxaline derivative with an arylboronic acid compound (A2) of a bicarbazole derivative.

-continued

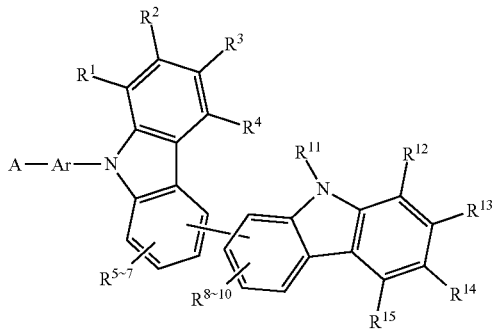

(G0)

In the formula, A represents a dibenzo[f,h]quinoxalinyl group; $R^1$ to $R^{15}$ represent independently hydrogen, a substituted or unsubstituted alkyl group having 1 to 6 carbon atoms, a substituted or unsubstituted cycloalkyl group having 5 to 7 carbon atoms, or a substituted or unsubstituted aryl group having 6 to 13 carbon atoms; and Ar represents a substituted or unsubstituted arylene group having 6 to 25 carbon atoms or a single bond. Preferably, an arylene group in Ar does not include an anthracenylene group. Furthermore, X represents a halogen. When Ar is a substituted or unsubstituted arylene group having 6 to 25 carbon atoms, B represents a boronic acid, a boronic ester, a cyclic-triolborate salt, or the like. As the cyclic-triolborate salt, a lithium salt, a potassium salt, or a sodium salt may be used. When Ar is a single bond, B represents hydrogen.

In addition, as shown in the following synthesis scheme (b), the dibenzo[f,h]quinoxaline derivative represented by the general formula (G0) can be obtained in such a manner that an intermediate (B2) is obtained through a reaction of a halogen compound (A1) of a dibenzo[f,h]quinoxaline derivative with a halogen-substituted arylboronic acid (B1) and then made to react with a bicarbazole derivative (B3).

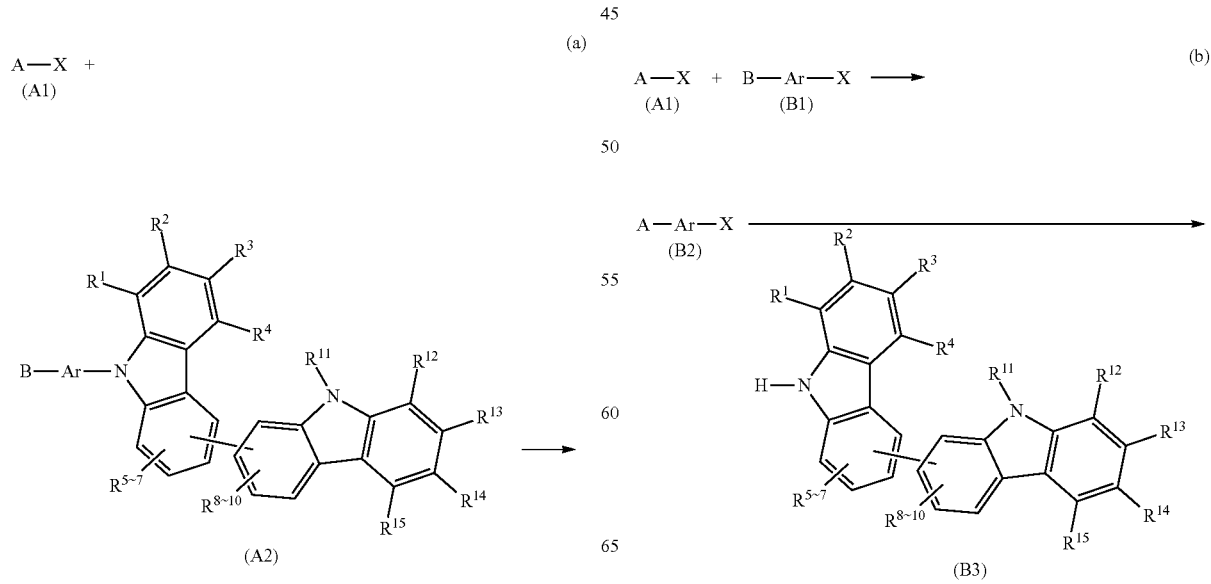

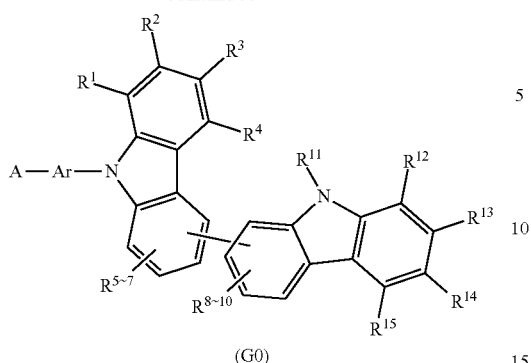

(G0)

In the formula, A represents a dibenzo[f,h]quinoxalinyl group; $R^1$ to $R^{15}$ represent independently hydrogen, a substituted or unsubstituted alkyl group having 1 to 6 carbon atoms, a substituted or unsubstituted cycloalkyl group having 5 to 7 carbon atoms, or a substituted or unsubstituted aryl group having 6 to 13 carbon atoms; and Ar represents a substituted or unsubstituted arylene group having 6 to 25 carbon atoms or a single bond. Preferably, an arylene group in Ar does not include an anthracenylene group. Furthermore, X represents a halogen. B represents a boronic acid, a boronic ester, a cyclic-triolborate salt, or the like.

When Ar in the general formula (G0) is a single bond, a halogen compound (A1) of a dibenzo[f,h]quinoxaline derivative is directly reacted with a bicarbazole derivative (B3).

A dibenzo[f,h]quinoxaline derivative which is one embodiment of the present invention and can be synthesized by any of the above synthesis methods is preferably a compound represented by any of the above general formulae (G1) to (G3). Specific structural formulae of dibenzo[f,h]quinoxaline derivatives which are embodiments of the present invention and represented by the general formulae (G0) to (G3) are shown below (the following structural formulae (100) to (131)). Note that the present invention is not limited thereto.

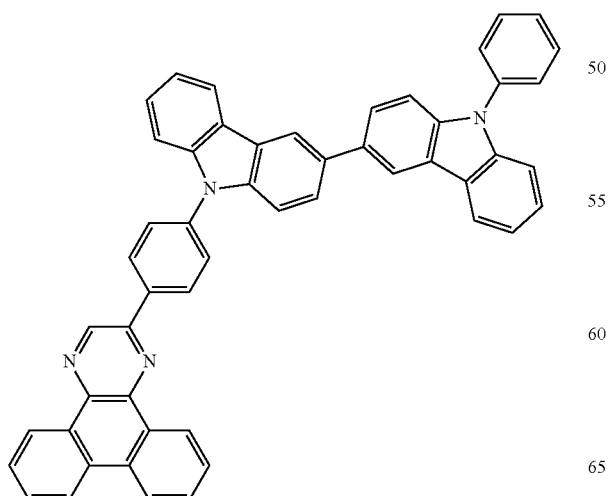

(100)

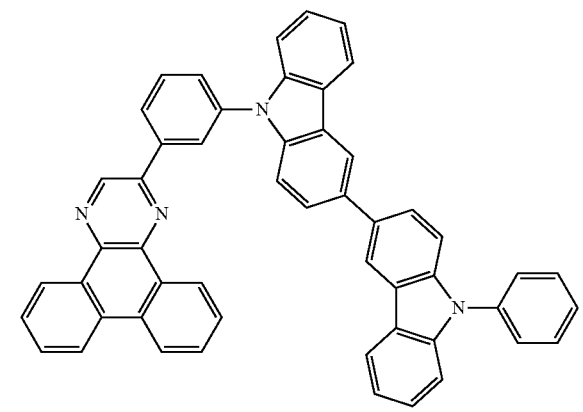

(101)

(102)

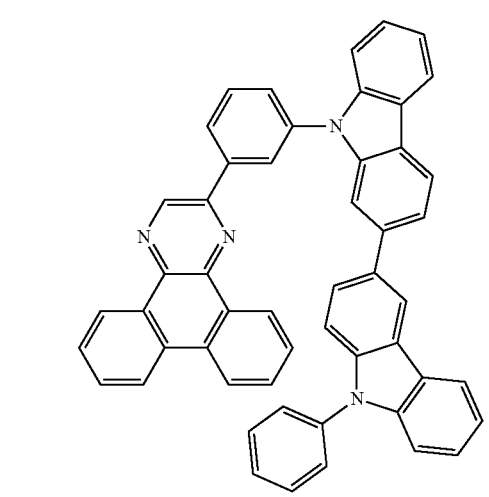

(103)

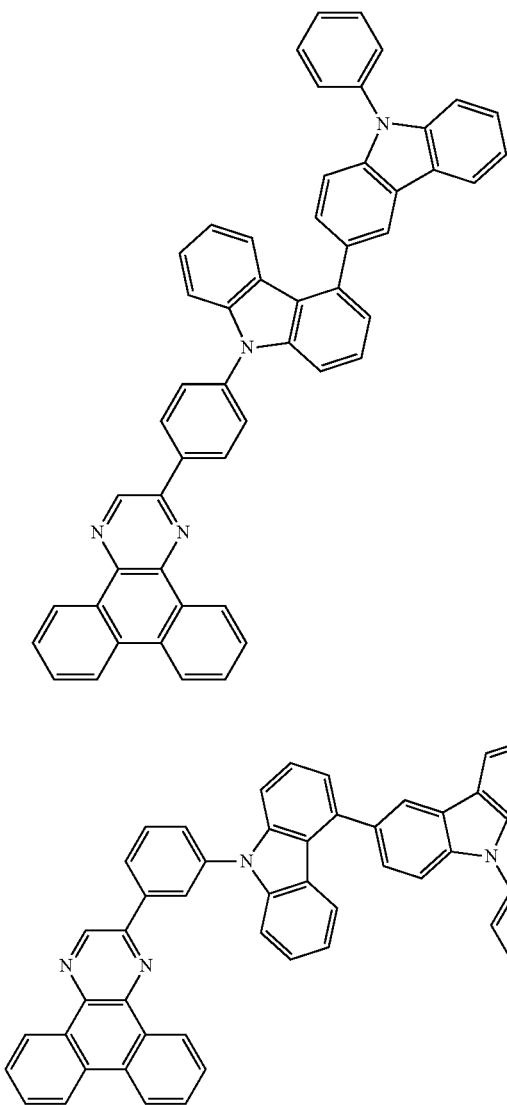
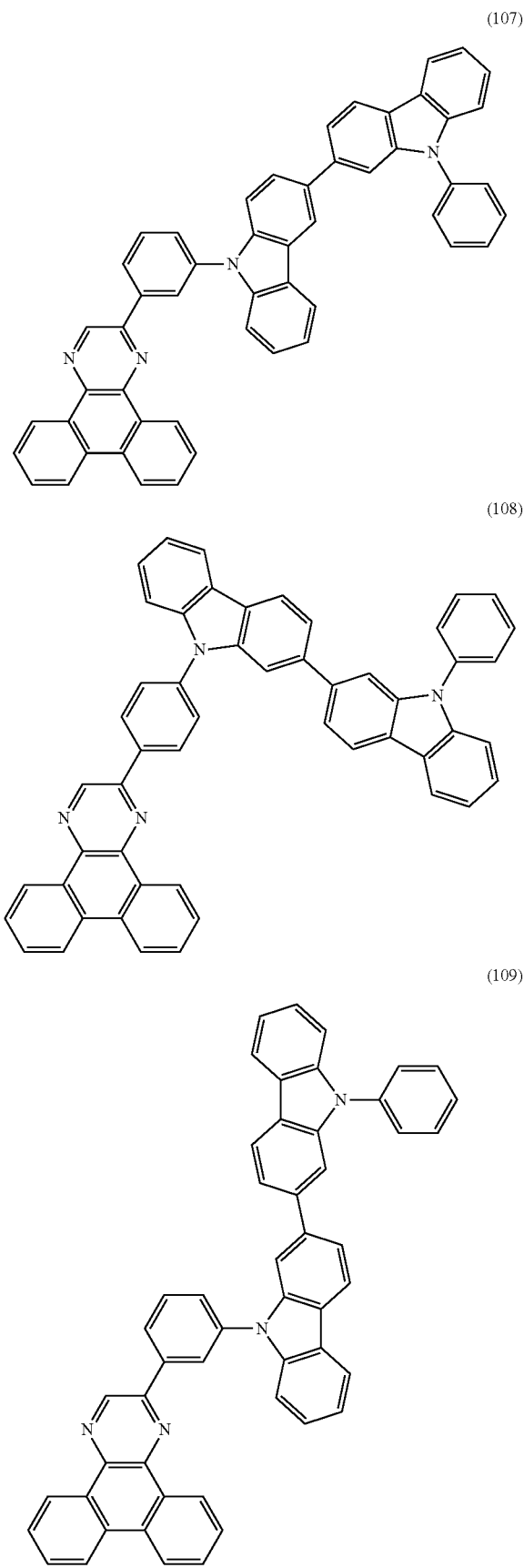

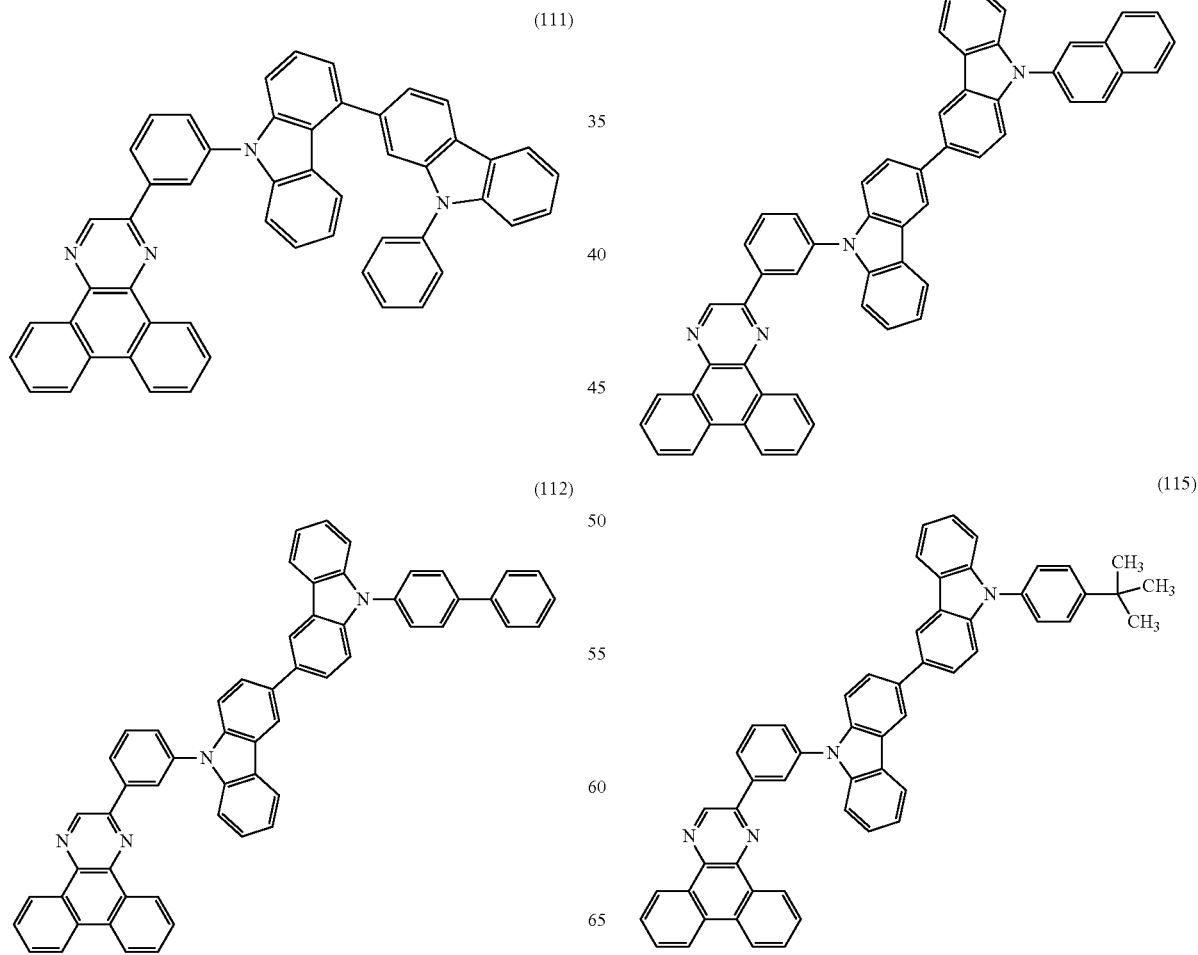

(116)
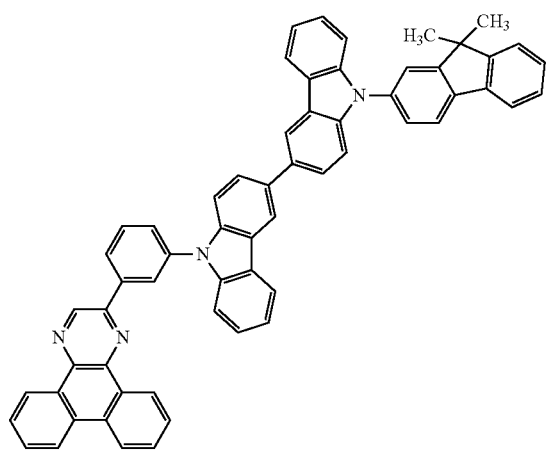
(119)
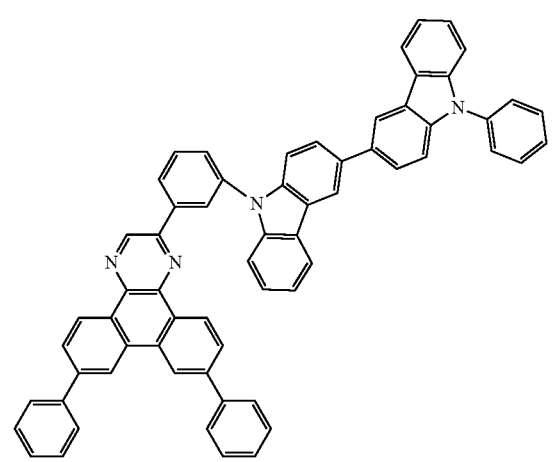
(117)
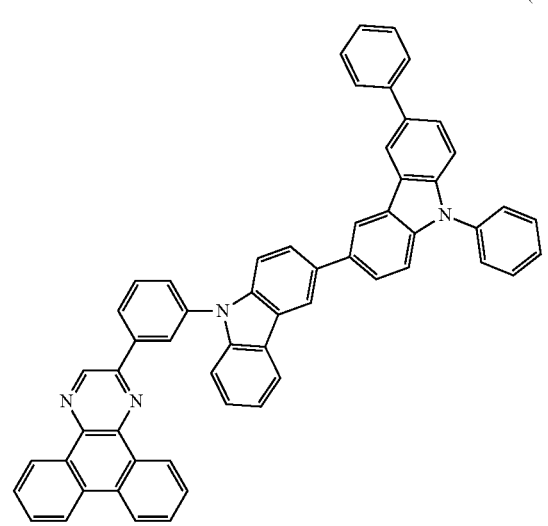
(120)
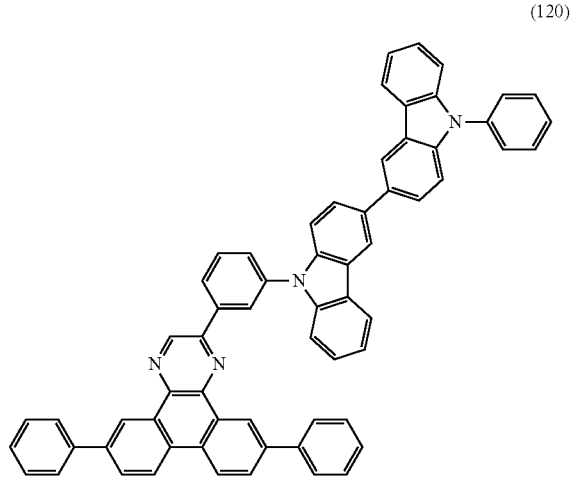
(118)
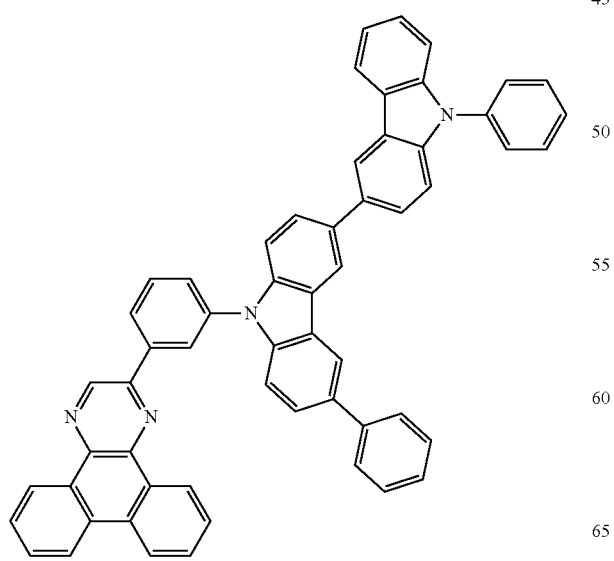
(121)
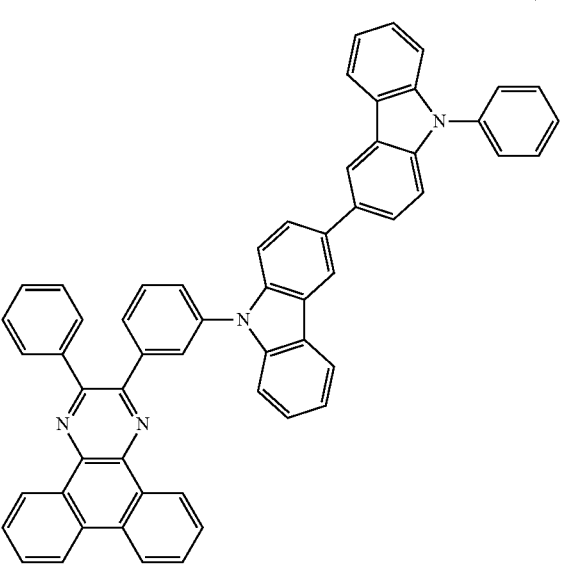

-continued
(122)
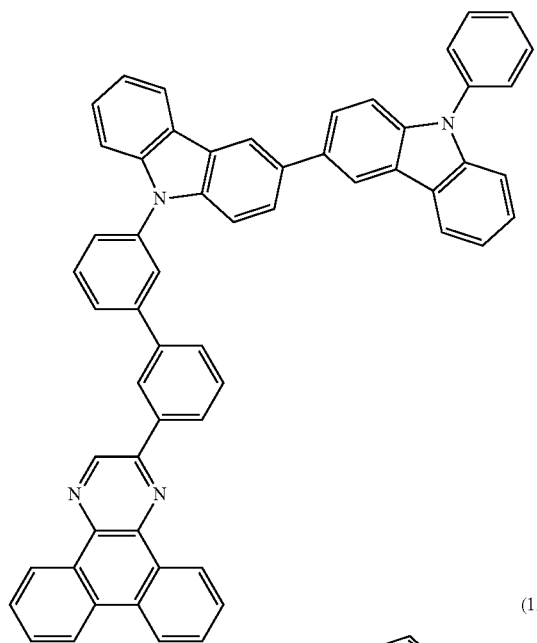
(123)
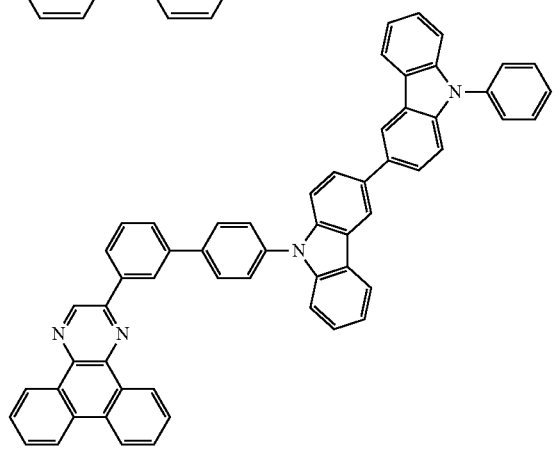
(124)
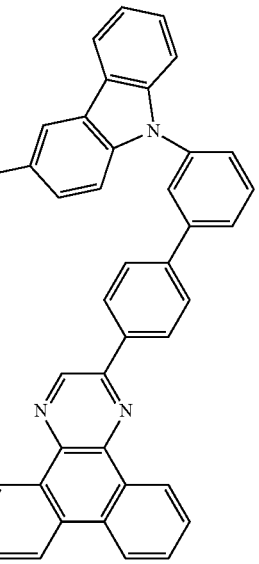
-continued
(125)
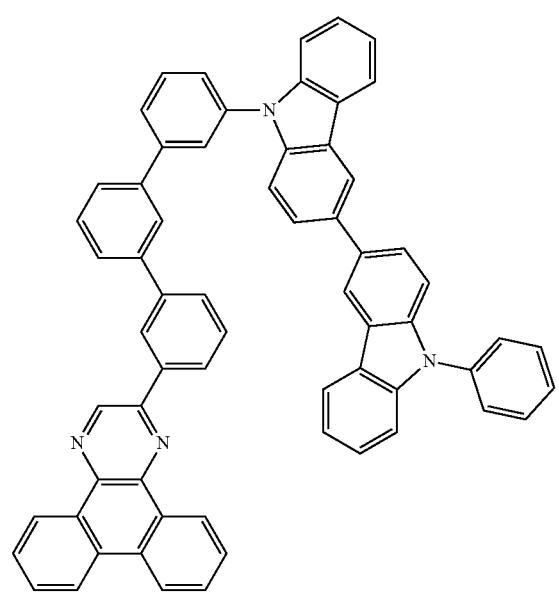
(126)
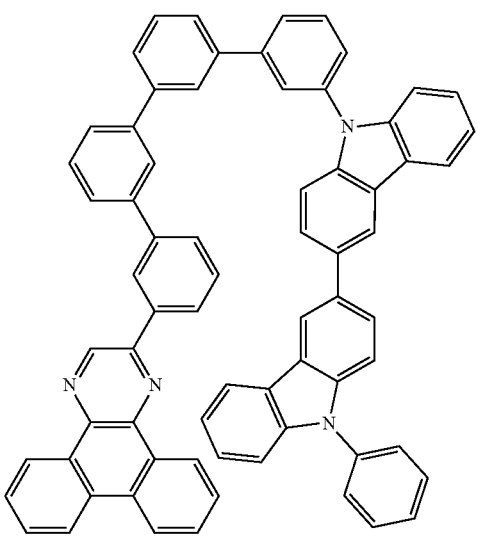
(127)
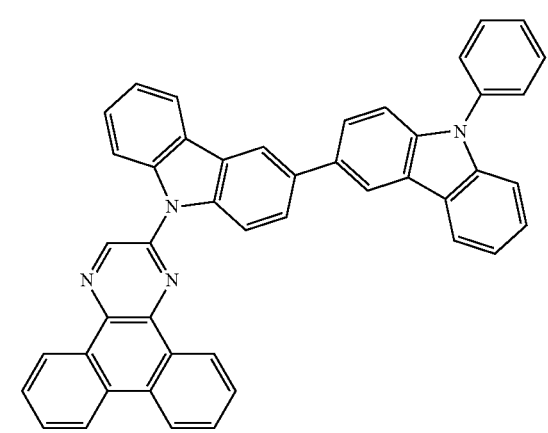

(128)
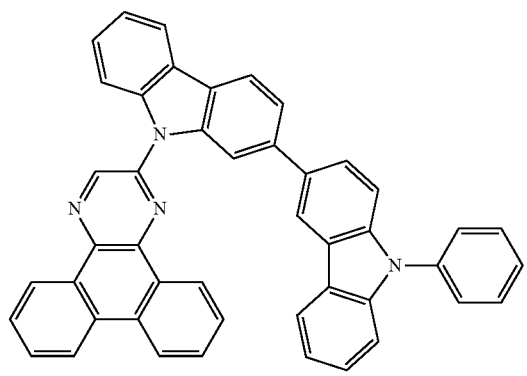

(129)
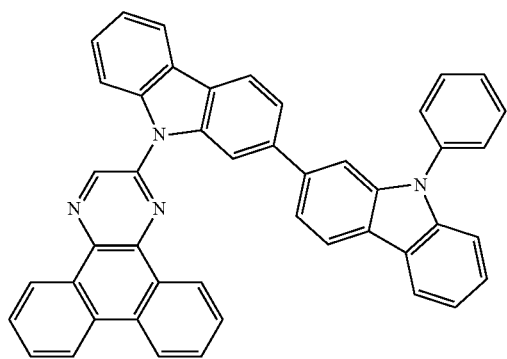

(130)
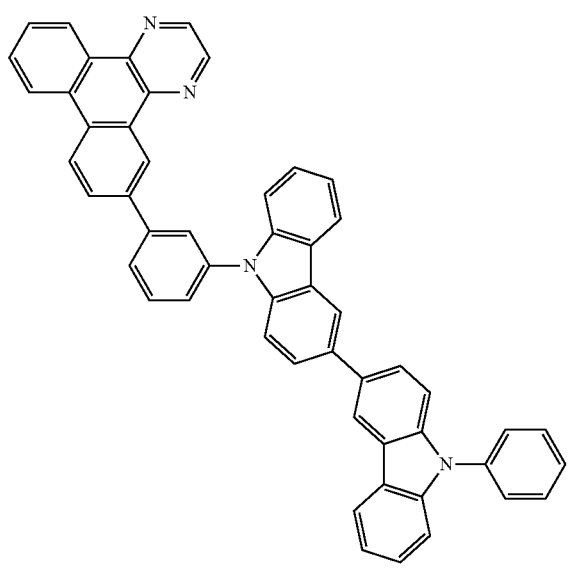

(131)
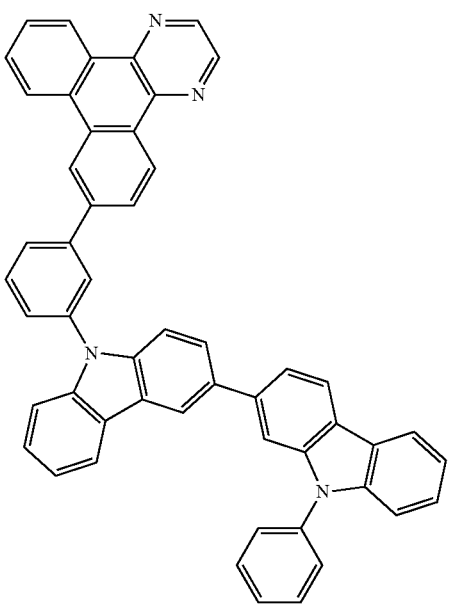

A dibenzo[f,h]quinoxaline derivative which is one embodiment of the present invention is used in a light-emitting element of one embodiment of the present invention, whereby a light-emitting element, a light-emitting device, an electronic device, or a lighting device with a high emission efficiency and a high reliability can be obtained. It is also possible to achieve a light-emitting element, a light-emitting device, an electronic device, or a lighting device with low power consumption.

The dibenzo[f,h]quinoxaline derivative represented by any of the general formulae (G0) to (G3) has an electron-transport property and a hole-transport property and thus can be used as a host material of a light-emitting layer or used for an electron-transport layer or a hole-transport layer. Furthermore, the dibenzo[f,h]quinoxaline derivative represented by any of the general formulae (G0) to (G3) emits fluorescence and thus can be used as a light-emitting substance of a light-emitting element. As described above, the dibenzo[f,h]quinoxaline derivative represented by any of the general formulae (G0) to (G3) is a useful novel compound which can be used as various materials in a light-emitting element; thus, a light-emitting element containing the dibenzo[f,h]quinoxaline derivative represented by any of the general formulae (G0) to (G3) is a light-emitting element which is one embodiment of the present invention.

Note that the structure described in this embodiment can be combined as appropriate with any of the structures described in the other embodiments.

Embodiment 3

Figure 4A:
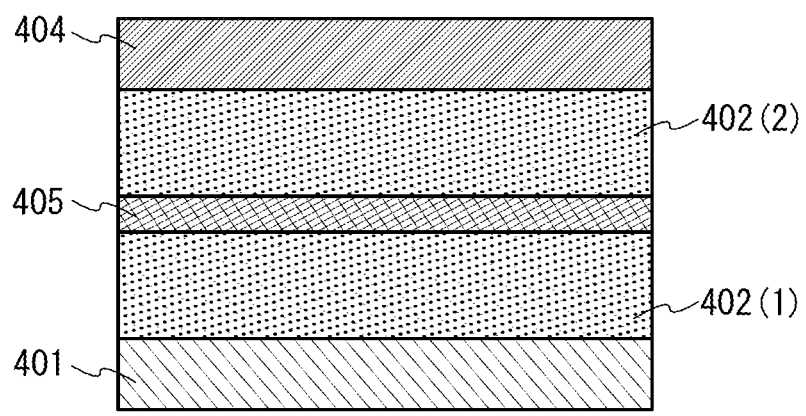
FIGS. 4A and 4B each illustrate the structure of a light-emitting element.

In this embodiment, as a light-emitting element which is one embodiment of the present invention, a light-emitting element (hereinafter referred to as a tandem light-emitting element) that includes a plurality of EL layers with a charge-generation layer provided therebetween will be described. As illustrated in FIG. 4A, the tandem light-emitting element includes a plurality of EL layers (a first EL layer 402(1) and a second EL layer 402(2)) between a pair of electrodes (a first electrode 401 and a second electrode 404).

In this embodiment, the first electrode 401 functions as an anode, and the second electrode 404 functions as a cathode. The first electrode 401 and the second electrode 404 can have structures similar to those described in Embodiment 1. All or any of the plurality of EL layers (the first EL layer 402(1) and the second EL layer 402(2)) may have structures similar to those described in Embodiment 1. In other words, the structures of the first EL layer 402(1) and the second EL layer 402(2) may be the same or different from each other and can be similar to those described in Embodiment 1. The dibenzo[f,h]quinoxaline derivative described in Embodiment 2 can be used for any of the plurality of EL layers (the first EL layer 402(1) and the second EL layer 402(2)).

A charge-generation layer 405 is provided between the plurality of EL layers (the first EL layer 402(1) and the second EL layer 402(2)). The charge-generation layer 405 has a function of injecting electrons into one of the EL layers and injecting holes into the other of the EL layers when a voltage is applied between the first electrode 401 and the second electrode 404. In this embodiment, when a voltage is applied such that the potential of the first electrode 401 is higher than that of the second electrode 404, the charge-generation layer 405 injects electrons into the first EL layer 402(1) and injects holes into the second EL layer 402(2).

In terms of light extraction efficiency, the charge-generation layer 405 preferably has a light-transmitting property with respect to visible light (specifically, the charge-generation layer 405 has a visible light transmittance of higher than or equal to 40%). Furthermore, the charge-generation layer 405 functions even if it has lower conductivity than the first electrode 401 or the second electrode 404.

The charge-generation layer 405 may have either a structure in which an electron acceptor is added to an organic compound having a high hole-transport property or a structure in which an electron donor is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances described here are mainly substances each having a hole mobility of higher than or equal to $1\times10^{-6}$ cm$^2$/Vs. Note that other substances may also be used as long as the substances have higher hole-transport properties than electron-transport properties.

As the electron acceptor, 7,7,8,8-tetracyano-2,3,5,6-tetrafluoroquinodimethane (abbreviation: F$_4$-TCNQ), chloranil, and the like can be given. In addition, transition metal oxides can be given. Moreover, oxides of metals belonging to Groups 4 to 8 of the periodic table can be given. Specifically, it is preferable to use vanadium oxide, niobium oxide, tantalum oxide, chromium oxide, molybdenum oxide, tungsten oxide, manganese oxide, and rhenium oxide because of their high electron accepting properties. In particular, molybdenum oxide is preferable because of its stability in the air, a low hygroscopic property, and easiness of handling.

On the other hand, in the case of the structure in which an electron donor is added to an organic compound having a high electron-transport property, as the organic compound having a high electron-transport property, for example, a metal complex having a quinoline skeleton or a benzoquinoline skeleton, such as Alq$_3$, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$ can be used. Alternatively, in addition to such a metal complex, PBD, OXD-7, TAZ, BPhen, BCP, or the like can be used. The substances described here are mainly substances each having an electron mobility of higher than or equal to $1\times10^{-6}$ cm$^2$/Vs. Note that other substances may also be used as long as the substances have higher electron-transport properties than hole-transport properties.

As the electron donor, it is possible to use an alkali metal, an alkaline earth metal, a rare earth metal, a metal belonging to Group 2 or 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that forming the charge-generation layer 405 by using any of the above materials can suppress an increase in drive voltage caused by the stack of the EL layers.

Figure 4B:
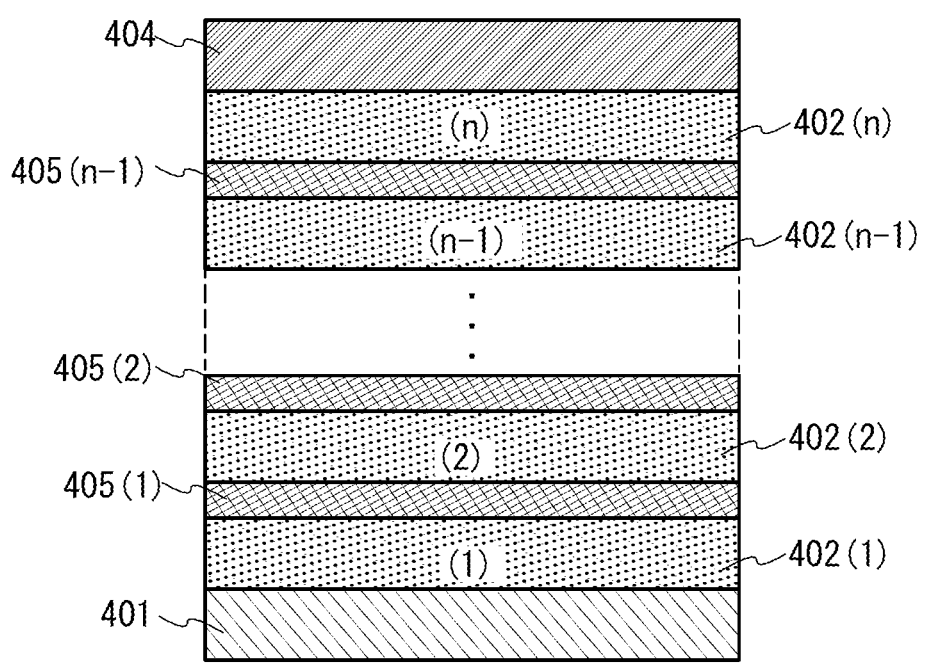

Although the light-emitting element including two EL layers is described in this embodiment, the present invention can be similarly applied to a light-emitting element in which n EL layers (402(1) to 402(n)) (n is three or more) are stacked as illustrated in FIG. 4B. In the case where a plurality of EL layers are included between a pair of electrodes as in the light-emitting element of this embodiment, by providing charge-generation layers (405(1) to 405(n-1)) between the EL layers, light emission in a high luminance region can be obtained with current density kept low. Since the current density can be kept low, the element can have a long lifetime. In addition, when the light-emitting element is applied to a light-emitting device, an electronic device, a lighting device, and the like each having a large light-emitting area, voltage drop due to resistance of an electrode material can be reduced, thereby achieving homogeneous light emission in a large area.

When the EL layers have different emission colors, a desired emission color can be obtained from the whole light-emitting element. For example, in the light-emitting element including two EL layers, when an emission color of a first EL layer and an emission color of a second EL layer are made to be complementary colors, a light-emitting element emitting white light as a whole light-emitting element can be obtained. Note that "complementary color" means a relation between colors which becomes an achromatic color when they are mixed. In other words, when lights which are complementary to each other are mixed, white light emission can be obtained. Specifically, a combination in which blue light emission is obtained from the first EL layer and yellow (or orange) light emission is obtained from the second EL layer is given as an example. In that case, it is not necessary that blue light emission and yellow (or orange) light emission are both fluorescence or both phosphorescence. For example, a combination in which blue light emission is fluorescence and yellow (or orange) light emission is phosphorescence or a combination in which blue light emission is phosphorescence and yellow (or orange) light emission is fluorescence may be employed. Moreover, a stacked structure suitable for adjustment of an optical path length of the light-emitting element (e.g., a structure in which a first light-emitting layer exhibits yellow light emission and a second light-emitting layer exhibits blue light emission) is preferably employed, in which case the element characteristics can be further improved.

Also in a light-emitting element including three EL layers, for example, white light emission can be similarly obtained from a whole light-emitting element when an emission color of a first EL layer is red, an emission color of a second EL layer is green, and an emission color of a third EL layer is blue.

Note that the structure described in this embodiment can be combined as appropriate with any of the structures described in the other embodiments.

Embodiment 4

In this embodiment, one embodiment of a light-emitting device in which the light-emitting element described in Embodiment 1 is combined with a coloring layer (a color filter or the like) will be described. In this embodiment, the structure of a pixel portion of the light-emitting device will be described with reference to FIG. 5.

Figure 5:
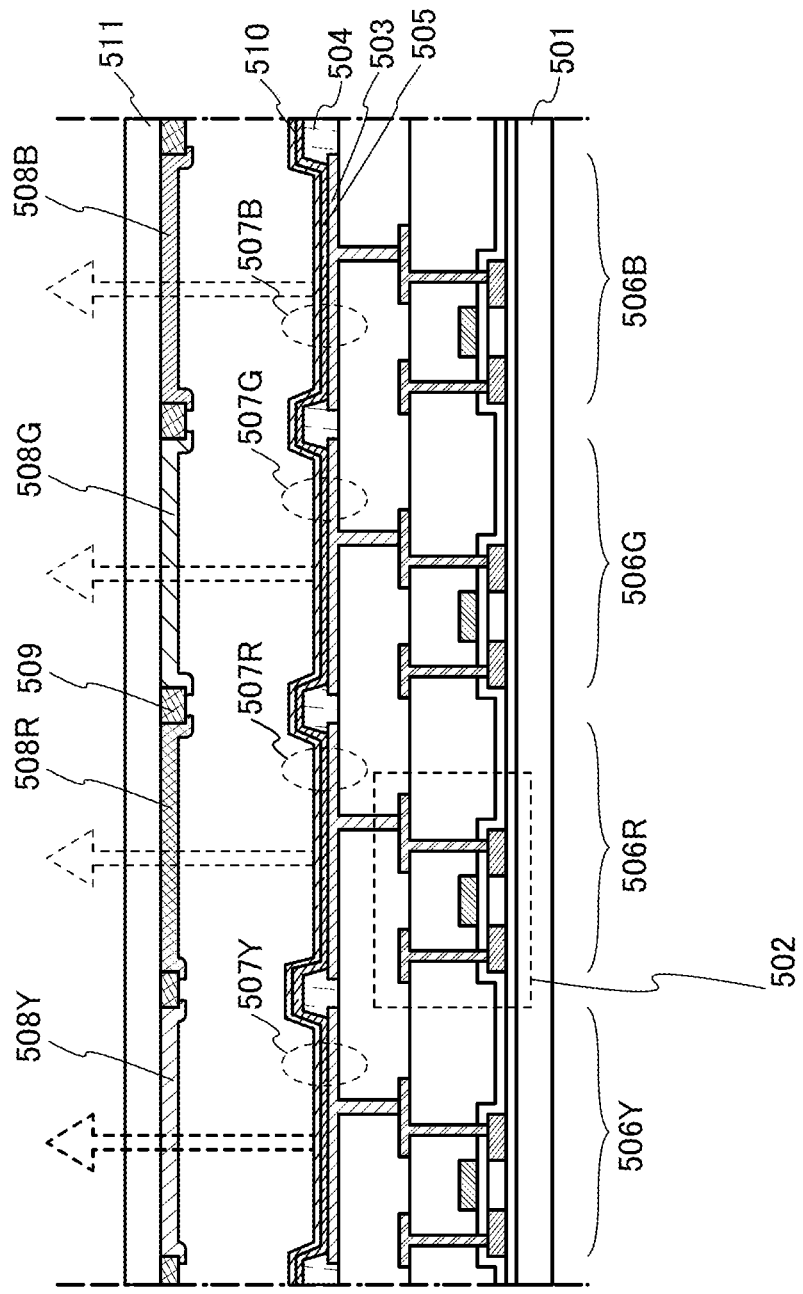
FIG. 5 illustrates a light-emitting device.

In FIG. 5, a plurality of FETs (transistors) 502 are formed over a substrate 501. Each of the FETs 502 is electrically connected to a light-emitting element (507R, 507G, 507B, or 507Y). Specifically, each of the FETs 502 is electrically connected to a first electrode 503 that is a pixel electrode of the light-emitting element. A partition wall 504 is provided to cover end portions of the adjacent first electrodes 503.

The first electrode 503 in this embodiment has a function of a reflective electrode. An EL layer 505 is formed over the first electrode 503, and a second electrode 510 is formed over the EL layer 505. The EL layer 505 includes a plurality of light-emitting layers each emitting monochromatic light. The second electrode 510 has a function of a semi-transmissive and semi-reflective electrode.

The light-emitting elements (507R, 507G, 507B, and 507Y) emit light of different colors. Specifically, the light-emitting element 507R is optically adjusted to emit red light, and in a region indicated by 506R, red light is emitted through a coloring layer 508R in the direction indicated by an arrow. The light-emitting element 507G is optically adjusted to emit green light, and in a region indicated by 506G, green light is emitted through a coloring layer 508G in the direction indicated by an arrow. The light-emitting element 507B is optically adjusted to emit blue light, and in a region indicated by 506B, blue light is emitted through a coloring layer 508B in the direction indicated by an arrow. The light-emitting element 507Y is optically adjusted to emit yellow light, and in a region indicated by 506Y, yellow light is emitted through a coloring layer 508Y in the direction indicated by an arrow.

As illustrated in FIG. 5, each of the coloring layers (508R, 508G, 508B, and 508Y) is provided on a transparent sealing substrate 511 that is provided above the substrate 501 over which the light emitting elements (507R, 507G, 507B, and 507Y) are formed. Note that the coloring layers (508R, 508G, 508B, and 508Y) are provided in positions overlapping with the corresponding light-emitting elements (507R, 507G, 507B, and 507Y) which exhibit different emission colors.

A black layer (black matrix) 509 is provided to overlap with end portions of the adjacent coloring layers (508R, 508G, 508B, and 508Y). Note that the coloring layers (508R, 508G, 508B, and 508Y) and the black layer 509 may be covered with an overcoat layer that is formed using a transparent material.

The above-described light-emitting device has a structure in which light is extracted from the sealing substrate 511 side (a top emission structure), but may have a structure in which light is extracted from the substrate 501 side where the FETs are formed (a bottom emission structure). Note that in the light-emitting device having a top emission structure described in this embodiment, a light-blocking substrate or a light-transmitting substrate can be used as the substrate 501, whereas in a light-emitting device having a bottom emission structure, a light-transmitting substrate needs to be used as the substrate 501.

In this specification and the like, a transistor or a light-emitting element can be formed using any of a variety of substrates, for example. The type of a substrate is not limited to a certain type. As the substrate, a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, a base material film, or the like can be used, for example. Examples of a glass substrate include a barium borosilicate glass substrate, an aluminoborosilicate glass substrate, and a soda lime glass substrate. Examples of the flexible substrate, the attachment film, the base material film, and the like include plastics typified by polyethylene terephthalate (PET), polyethylene naphthalate (PEN), polyether sulfone (PES), and polytetrafluoroethylene (PTFE), a synthetic resin such as acrylic, films formed of polypropylene, polyester, polyvinyl fluoride, and polyvinyl chloride, films formed of polyamide, polyimide, aramid, and epoxy, an inorganic film formed by evaporation, and paper. Specifically, when a transistor is fabricated using a semiconductor substrate, a single crystal substrate, an SOI substrate, or the like, a transistor with few variations in characteristics, size, shape, or the like, high current supply capability, and a small size can be fabricated. A circuit using such a transistor achieves lower power consumption or higher integration.

Alternatively, a flexible substrate may be used as the substrate, and the transistor or the light-emitting element may be provided directly over the flexible substrate. Further alternatively, a separation layer may be provided between a substrate and the transistor or the like. The separation layer can be used when part of or the entire semiconductor device formed over the separation layer is separated from the substrate and transferred onto another substrate. In such a case, the transistor or the like can be transferred to a substrate having low heat resistance or a flexible substrate as well. For the above separation layer, a stack including inorganic films, a tungsten film and a silicon oxide film, or an organic resin film of polyimide or the like formed over a substrate can be used, for example.

In other words, after the transistor or the light-emitting element is formed using one substrate, the transistor or the light-emitting element may be transferred to another substrate. Examples of a substrate to which the transistor or the light-emitting element is transferred include, in addition to the above-described substrates over which a transistor or the like can be formed, a paper substrate, a cellophane substrate, an aramid film substrate, a polyimide film substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, and a rubber substrate. When such a substrate is used, a transistor or the like with excellent properties or low power consumption can be formed, a device with high durability and high heat resistance can be provided, or a reduction in weight or thickness can be achieved.

Note that the structure described in this embodiment can be combined as appropriate with any of the structures described in the other embodiments.

Embodiment 5

In this embodiment, a light-emitting device including a light-emitting element in which a dibenzo[f,h]quinoxaline derivative which is one embodiment of the present invention is used for an EL layer will be described.

The light-emitting device may be either a passive matrix light-emitting device or an active matrix light-emitting device. Note that any of the light-emitting elements described in the other embodiments can be applied to a light-emitting device described in this embodiment.

In this embodiment, an active matrix light-emitting device will be described with reference to FIGS. 6A and 6B.

Figure 6A:
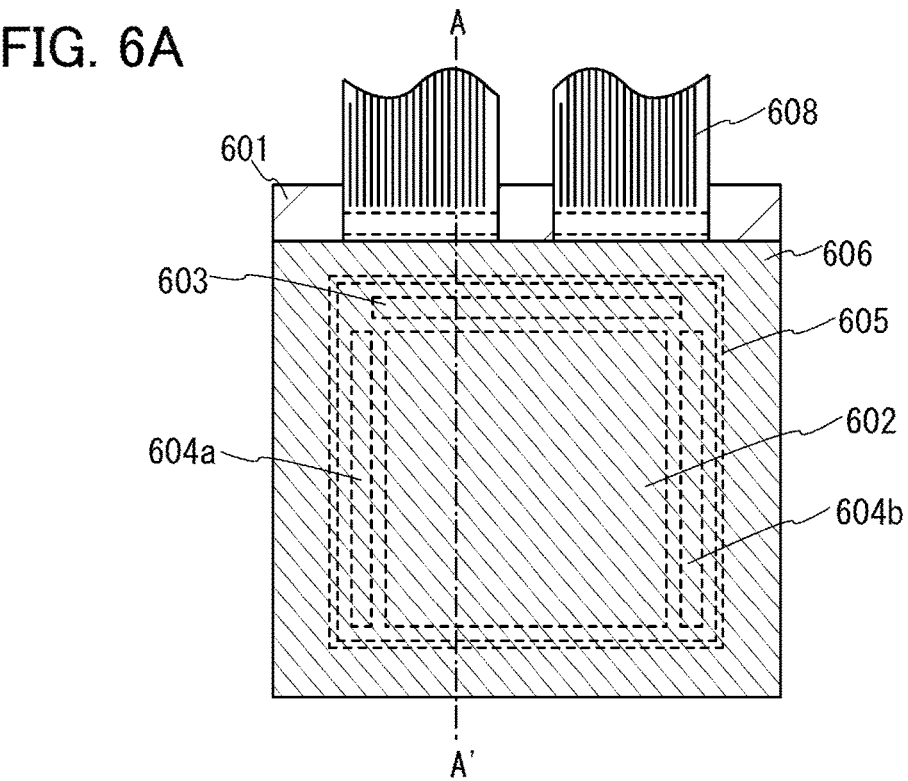
FIGS. 6A and 6B illustrate a light-emitting device.
Figure 6B:
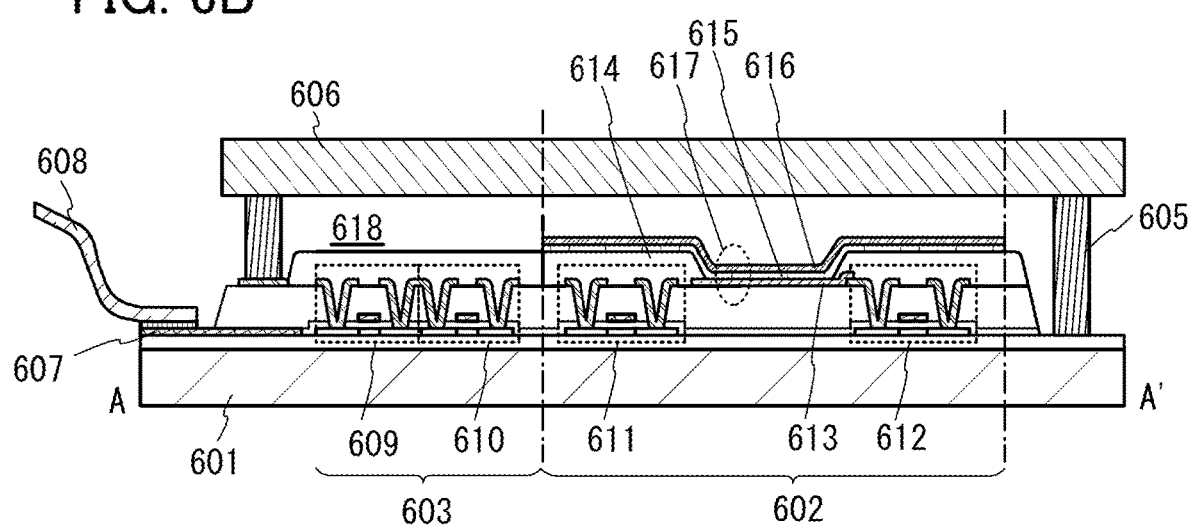

FIG. 6A is a top view illustrating the light-emitting device, and FIG. 6B is a cross-sectional view taken along the dashed-dotted line A-A' in FIG. 6A. The active matrix light-emitting device of this embodiment includes a pixel portion 602 provided over an element substrate 601, a driver circuit portion (a source line driver circuit) 603, and driver circuit portions (gate line driver circuits) 604a and 604b. The pixel portion 602, the driver circuit portion 603, and the driver circuit portions 604a and 604b are sealed with a sealant 605 between the element substrate 601 and a sealing substrate 606.

In addition, over the element substrate 601, a lead wiring 607 for connecting an external input terminal, through which a signal (e.g., a video signal, a clock signal, a start signal, a reset signal, or the like) or potential is transmitted from the outside to the driver circuit portion 603 and the driver circuit portions 604a and 604b, is provided. Here, an example is described in which a flexible printed circuit (FPC) 608 is provided as the external input terminal. Although only the FPC is illustrated here, the FPC may be provided with a printed wiring board (PWB). The light-emitting device in this specification includes, in its category, not only the light-emitting device itself but also the light-emitting device provided with an FPC or a PWB.

Next, a cross-sectional structure will be described with reference to FIG. 6B. The driver circuit portions and the pixel portion are formed over the element substrate 601; here are illustrated the driver circuit portion 603 which is the source line driver circuit and the pixel portion 602.

In the driver circuit portion 603, an FET 609 and an FET 610 are combined as an example. Note that the driver circuit portion 603 may be formed with a circuit including transistors having the same conductivity type (either n-channel transistors or p-channel transistors) or a CMOS circuit including an n-channel transistor and a p-channel transistor. In this embodiment, a driver-integrated type in which a driver circuit is formed over a substrate is shown; however, the driver circuit can also be formed outside the substrate.

The pixel portion 602 includes a plurality of pixels each including a switching FET 611, a current control FET 612, and a first electrode (anode) 613 electrically connected to a wiring (a source electrode or a drain electrode) of the current control FET 612. In this embodiment, the pixel portion 602 includes two FETs, the switching FET 611 and the current control FET 612, but one embodiment of the present invention is not limited thereto. The pixel portion 602 may include, for example, three or more FETs and a capacitor in combination.

As the FETs 609, 610, 611, and 612, for example, a staggered transistor or an inverted staggered transistor can be used. Examples of a semiconductor material that can be used for the FETs 609, 610, 611, and 612 include Group 13 semiconductors (e.g., gallium), Group 14 semiconductors (e.g., silicon), compound semiconductors, oxide semiconductors, and organic semiconductors. In addition, there is no particular limitation on the crystallinity of the semiconductor material, and an amorphous semiconductor film or a crystalline semiconductor film can be used, for example. An oxide semiconductor is preferably used for the FETs 609, 610, 611, and 612. Examples of the oxide semiconductor include an In—Ga oxide and an In-M-Zn oxide (M is Al, Ga, Y, Zr, La, Ce, or Nd). For example, an oxide semiconductor material that has an energy gap of 2 eV or more, preferably 2.5 eV or more, more preferably 3 eV or more is used for the FETs 609, 610, 611, and 612, so that the off-state current of the transistors can be reduced.

An insulator 614 is formed to cover an end portion of the first electrode 613. In this embodiment, the insulator 614 is formed using a positive photosensitive acrylic resin. The first electrode 613 is used as an anode in this embodiment.

The insulator 614 preferably has a curved surface with curvature at its upper end portion or lower end portion. This enables the coverage with a film to be formed over the insulator 614 to be favorable. The insulator 614 can be formed using, for example, either a negative photosensitive resin or a positive photosensitive resin. The material of the insulator 614 is not limited to an organic compound, and an inorganic compound such as silicon oxide, silicon oxynitride, or silicon nitride can also be used.

An EL layer 615 and a second electrode (cathode) 616 are stacked over the first electrode (anode) 613. At least a light-emitting layer is provided in the EL layer 615. Furthermore, in the EL layer 615, a hole-injection layer, a hole-transport layer, an electron-transport layer, an electron-injection layer, a charge-generation layer, and the like can be provided as appropriate in addition to the light-emitting layer.

A light-emitting element 617 is formed of a stacked structure of the first electrode (anode) 613, the EL layer 615, and the second electrode (cathode) 616. For the first electrode (anode) 613, the EL layer 615, and the second electrode (cathode) 616, the materials described in Embodiment 2 can be used. Although not illustrated here, the second electrode (cathode) 616 is electrically connected to the FPC 608 which is an external input terminal.

Although the cross-sectional view in FIG. 6B illustrates only one light-emitting element 617, a plurality of light-emitting elements are arranged in a matrix in the pixel portion 602. Light-emitting elements which emit light of three kinds of colors (R, G, and B) are selectively formed in the pixel portion 602, whereby a light-emitting device capable of full color display can be formed. In addition to the light-emitting elements that emit light of three kinds of colors (R, G, and B), for example, light-emitting elements that emit light of white (W), yellow (Y), magenta (M), cyan (C), and the like may be formed. For example, the light-emitting elements that emit light of a plurality of kinds of colors are used in combination with the light-emitting elements that emit light of three kinds of colors (R, G, and B), whereby effects such as an improvement in color purity and a reduction in power consumption can be obtained. Alternatively, a light-emitting device which is capable of full color display may be fabricated by a combination with color filters. Furthermore, the light-emitting device may have an improved emission efficiency and a reduced power consumption by combination with quantum dots.

The sealing substrate 606 is attached to the element substrate 601 with the sealant 605, so that the light-emitting element 617 is provided in a space 618 surrounded by the element substrate 601, the sealing substrate 606, and the sealant 605. The space 618 may be filled with an inert gas (such as nitrogen or argon) or the sealant 605.

An epoxy-based resin or glass frit is preferably used for the sealant 605. It is preferable that such a material do not transmit moisture or oxygen as much as possible. As the element substrate 601 and the sealing substrate 606, a glass substrate, a quartz substrate, or a plastic substrate formed of fiber reinforced plastics (FRP), poly(vinyl fluoride) (PVF), polyester, acrylic, or the like can be used. In the case where glass frit is used as the sealant, the element substrate 601 and the sealing substrate 606 are preferably glass substrates for high adhesion.

In the above manner, an active matrix light-emitting device can be obtained.

Note that the structure described in this embodiment can be combined as appropriate with any of the structures described in the other embodiments.

Embodiment 6

In this embodiment, various examples of an electronic device manufactured using a light-emitting device which is one embodiment of the present invention will be described with reference to FIGS. 7A to 7D.

Examples of an electronic device to which a light-emitting device is applied include television devices (also referred to as TV or television receivers), monitors for computers and the like, cameras such as digital cameras and digital video cameras, digital photo frames, mobile phones (also referred to as cellular phones or portable telephone devices), portable game machines, portable information terminals, audio playback devices, and large game machines such as pin-ball machines. Specific examples of these electronic devices are illustrated in FIGS. 7A to 7D.

Figure 7A:
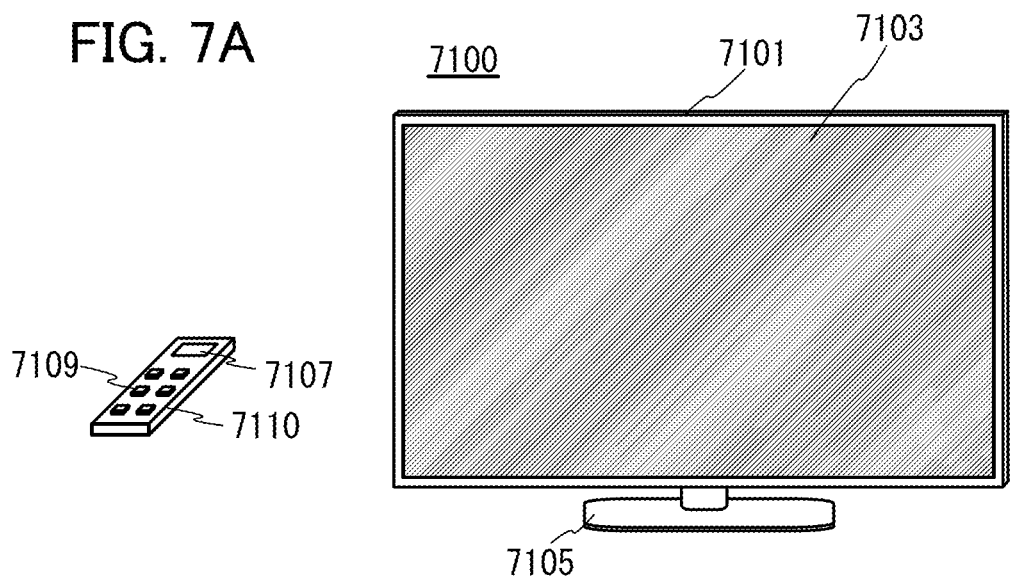
FIGS. 7A, 7B, 7C, 7D, 7D' 1 and 7D'2 each illustrate an electronic device.

FIG. 7A illustrates an example of a television device. In a television device 7100, a display portion 7103 is incorporated in a housing 7101. The display portion 7103 can display images and may be a touch panel (an input/output device) including a touch sensor (an input device). Note that the light-emitting device which is one embodiment of the present invention can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying information output from the remote controller 7110.

Note that the television device 7100 is provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) information communication can be performed.

Figure 7B:
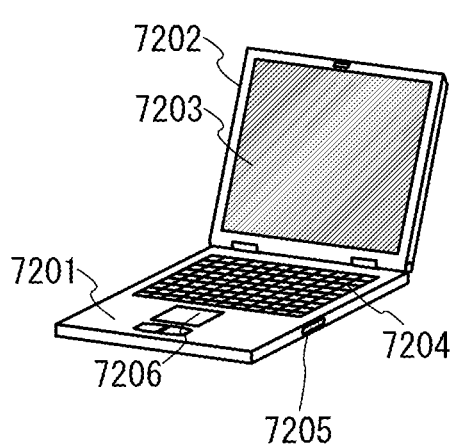

FIG. 7B illustrates a computer, which includes a main body 7201, a housing 7202, a display portion 7203, a keyboard 7204, an external connecting port 7205, a pointing device 7206, and the like. Note that this computer can be manufactured using the light-emitting device which is one embodiment of the present invention for the display portion 7203. The display portion 7203 may be a touch panel (an input/output device) including a touch sensor (an input device).

Figure 7C:
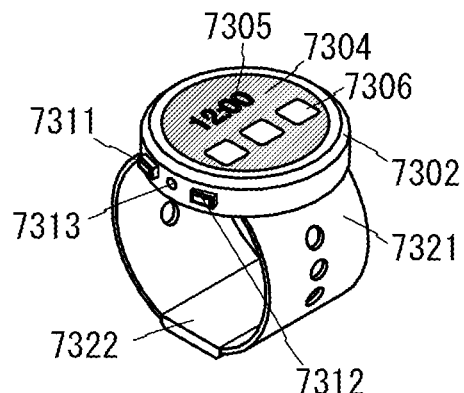

FIG. 7C illustrates a smart watch, which includes a housing 7302, a display panel 7304, operation buttons 7311 and 7312, a connection terminal 7313, a band 7321, a clasp 7322, and the like.

The display panel 7304 mounted in the housing 7302 serving as a bezel includes a non-rectangular display region. The display panel 7304 can display an icon 7305 indicating time, another icon 7306, and the like. The display panel 7304 may be a touch panel (an input/output device) including a touch sensor (an input device).

The smart watch illustrated in FIG. 7C can have a variety of functions, for example, a function of displaying a variety of information (e.g., a still image, a moving image, and a text image) on a display portion, a touch panel function, a function of displaying a calendar, date, time, and the like, a function of controlling processing with a variety of software (programs), a wireless communication function, a function of being connected to a variety of computer networks with a wireless communication function, a function of transmitting and receiving a variety of data with a wireless communication function, and a function of reading a program or data stored in a recording medium and displaying the program or data on a display portion.

The housing 7302 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like. Note that the smart watch can be manufactured using the light-emitting device for the display panel 7304.

Figure 7D:
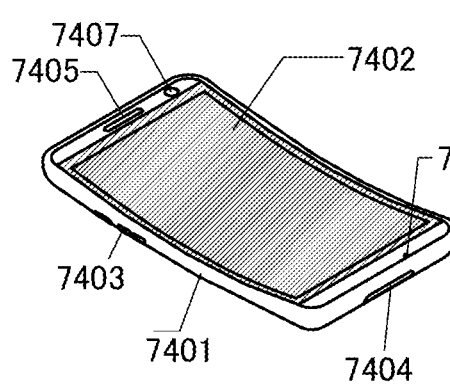
Figure 7D:
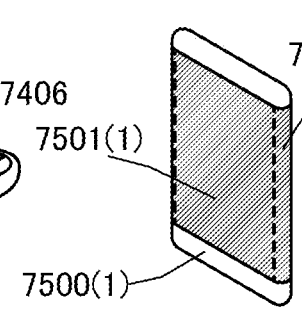
Figure 7D:
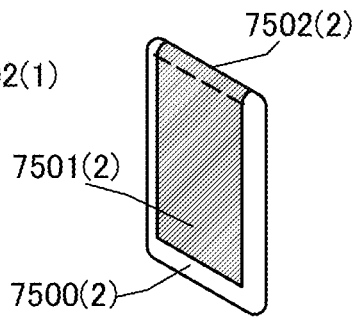

FIG. 7D illustrates an example of a mobile phone (e.g., smartphone). A mobile phone 7400 includes a housing 7401 provided with a display portion 7402, a microphone 7406, a speaker 7405, a camera 7407, an external connection portion 7404, an operation button 7403, and the like. In the case where a light-emitting device is manufactured by forming the light-emitting element of one embodiment of the present invention over a flexible substrate, the light-emitting device can be used for the display portion 7402 with a curved surface as illustrated in FIG. 7D.

When the display portion 7402 of the mobile phone 7400 illustrated in FIG. 7D is touched with a finger or the like, information can be input into the mobile phone. Furthermore, operations such as making a call and creating an e-mail can be performed by touching the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are combined.

For example, in the case of making a call or creating an e-mail, a character input mode mainly for inputting characters is selected for the display portion 7402 so that characters displayed on the screen can be input. In this case, it is preferable to display a keyboard or number buttons on almost the entire screen of the display portion 7402.

When a detection device such as a gyroscope or an acceleration sensor is provided inside the mobile phone 7400, display on the screen of the display portion 7402 can be automatically changed by determining the orientation of the mobile phone 7400 (whether the mobile phone is placed horizontally or vertically for a landscape mode or a portrait mode).

The screen modes are changed by touch on the display portion 7402 or operation with the operation button 7403 of the housing 7401. The screen modes can also be changed depending on the kind of images displayed on the display portion 7402. For example, when a signal of an image displayed on the display portion is a signal of moving image data, the screen mode is changed to the display mode. When the signal is a signal of text data, the screen mode is changed to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by touch on the display portion 7402 with the palm or the finger, whereby personal authentication can be performed. Furthermore, when a backlight or a sensing light source which emits near-infrared light is provided in the display portion, an image of a finger vein, a palm vein, or the like can be taken.

Furthermore, the light-emitting device can also be used for a mobile phone having a structure illustrated in FIG. 7D'1 or FIG. 7D'2, which is another structure of the mobile phone (e.g., smartphone).

In the case of the structure illustrated in FIG. 7D'1 or FIG. 7D'2, character information, image information, or the like can be displayed on second screens 7502(1) and 7502(2) of housings 7500(1) and 7500(2) as well as first screens 7501(1) and 7501(2). Such a structure enables a user to easily see character information, image information, or the like displayed on the second screens 7502(1) and 7502(2) while the mobile phone is placed in user's breast pocket.

Figure 8A:
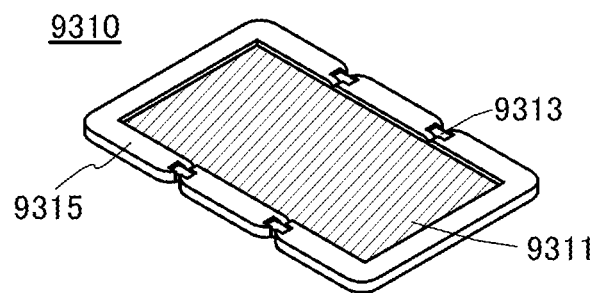
FIGS. 8A to 8C illustrate an electronic device.
Figure 8B:
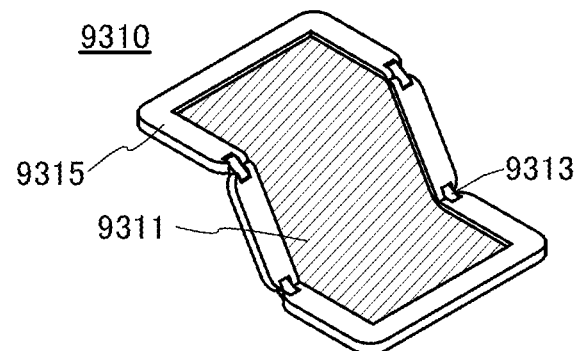
Figure 8C:
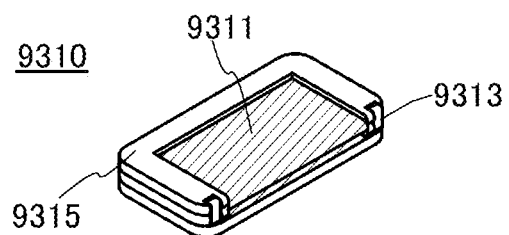

FIGS. 8A to 8C illustrate a foldable portable information terminal 9310. FIG. 8A illustrates the portable information terminal 9310 that is opened. FIG. 8B illustrates the portable information terminal 9310 that is being opened or being folded. FIG. 8C illustrates the portable information terminal 9310 that is folded. The portable information terminal 9310 is highly portable when folded. When the portable information terminal 9310 is opened, a seamless large display region is highly browsable.

A display panel 9311 is supported by three housings 9315 joined together by hinges 9313. The display panel 9311 may be a touch panel (an input/output device) including a touch sensor (an input device). By bending the display panel 9311 at a connection portion between two housings 9315 with the use of the hinges 9313, the portable information terminal 9310 can be reversibly changed in shape from an opened state to a folded state. The light-emitting device of one embodiment of the present invention can be used for the display panel 9311. A display region in the display panel 9311 includes a display region that is positioned at a side surface of the portable information terminal 9310 that is folded. On this display region, information icons, frequently-used applications, file shortcuts to programs, and the like can be displayed, and confirmation of information and start of application can be smoothly performed.

As described above, the electronic devices can be obtained by using the light-emitting device of one embodiment of the present invention. Note that the light-emitting device can be used for electronic devices in a variety of fields without being limited to the electronic devices described in this embodiment.

Note that the structure described in this embodiment can be combined as appropriate with any of the structures described in the other embodiments.

Embodiment 7

In this embodiment, examples of a lighting device to which a light-emitting device which is one embodiment of the present invention is applied, will be described with reference to FIG. 9.

Figure 9:
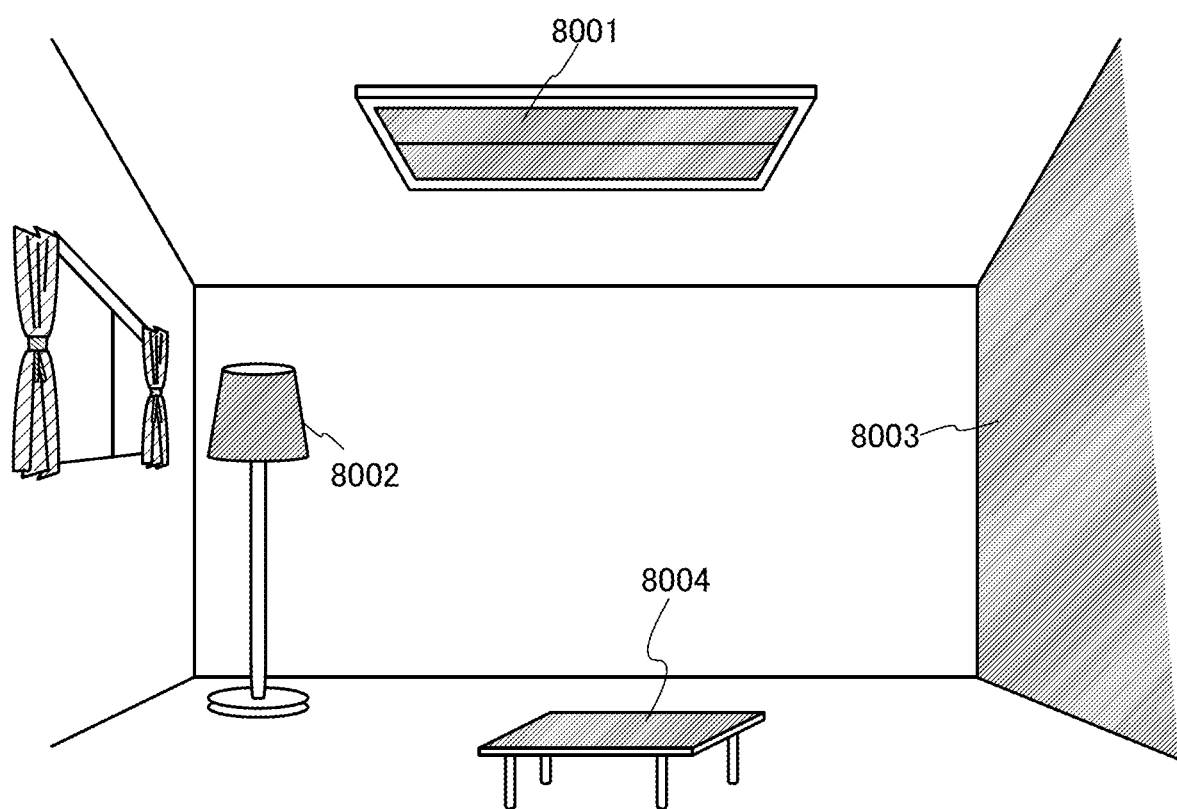
FIG. 9 illustrates lighting devices.

FIG. 9 illustrates an example in which the light-emitting device is used as an indoor lighting device 8001. Since the area of the light-emitting device can be increased, a lighting device having a large area can be formed. In addition, with the use of a housing with a curved surface, a lighting device 8002 which includes the housing, a cover, or a support and in which a light-emitting region has a curved surface can be obtained. A light-emitting element included in the light-emitting device described in this embodiment is in a thin film form, which allows the housing to be designed more freely. Therefore, the lighting device can be elaborately designed in a variety of ways. Furthermore, a wall of the room may be provided with a large-sized lighting device 8003.

Moreover, when the light-emitting device is used for a table by being used as a surface of the table, a lighting device 8004 which has a function as a table can be obtained. When the light-emitting device is used as part of other furniture, a lighting device which has a function as the furniture can be obtained.

In this manner, a variety of lighting devices to which the light-emitting device is applied can be obtained. Note that such lighting devices are also embodiments of the present invention.

Note that the structure described in this embodiment can be combined as appropriate with any of the structures described in the other embodiments.

Example 1

Synthesis Example 1

In this example, as a synthesis method of one embodiment of the present invention, a synthesis method of 2-{4-[3-(N-phenyl-9H-carbazol-3-yl)-9H-carbazol-9-yl]phenyl}dibenzo[f,h]quinoxaline (abbreviation:

2PCCzPDBq, represented by the structural formula (100)) will be described. The structure of 2PCCzPDBq is shown below.

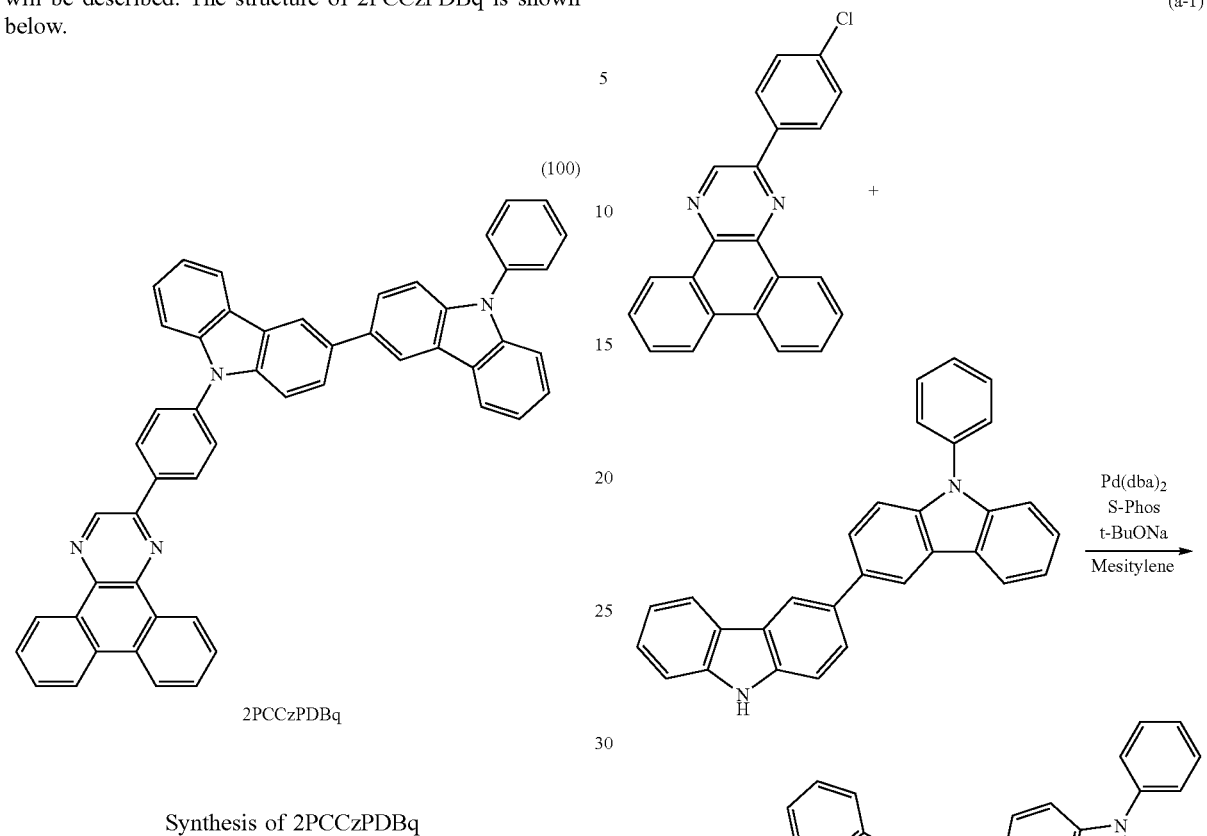

Synthesis of 2PCCzPDBq

First, 1.0 g (2.8 mmol) of 2-(4-chlorophenyl)dibenzo[f,h]quinoxaline, 1.1 g (2.8 mmol) of 3-(9-phenyl-9H-carbazol-3-yl)-9H-carbazole, 0.54 g (5.6 mmol) of sodium-tert-butoxide, and 23 mg (0.10 mmol) of 2-dicyclohexylphosphino-2',6'-dimethoxybiphenyl (abbreviation: S-Phos) were put in a 200-mL three-neck flask and mixed, and the air in the flask was replaced with nitrogen. To this mixture was added 14 mL of mesitylene, and the resulting mixture was degassed by being stirred while the pressure in the flask was reduced.

Then, 16 mg (0.028 mmol) of bis(dibenzylideneacetone) palladium(0) (abbreviation: Pd(dba)$_2$) was added to the mixture. This mixture was stirred at 150° C. for 5 hours under a nitrogen stream, so that a solid was precipitated. The precipitated solid was collected by suction filtration. The collected solid was dissolved in approximately 400 mL of hot toluene, and this solution was suction-filtered through a stack of Celite and alumina. The resulting filtrate was concentrated to give a solid. The solid was recrystallized with toluene to give 1.6 g of a yellow powder, which was the target substance, in a yield of 80%.

By a train sublimation method, 1.4 g of the obtained yellow powdered solid, which was the target substance, was purified. The sublimation purification was carried out at 380° C. under a pressure of 3.8 Pa with a flow rate of an argon gas at 10 mL/min. After the sublimation purification, 1.1 g of a yellow glassy solid of 2PCCzPDBq was obtained at a collection rate of 79%. The synthesis scheme of this step is shown in the following scheme (a-1).

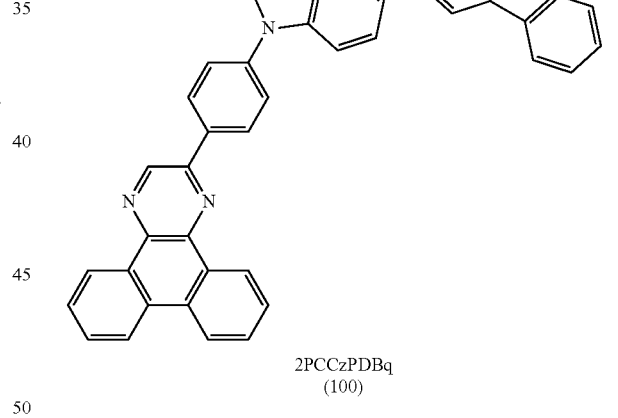

Figure 10A:
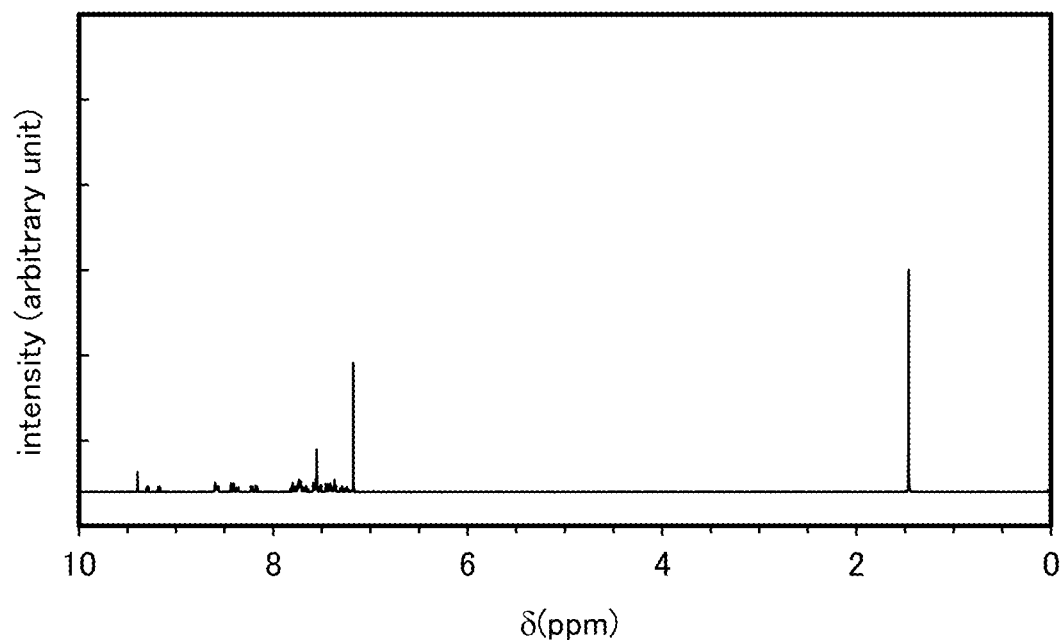
FIGS. 10A and 10B are $^1$H-NMR charts of a dibenzo[f,h]quinoxaline derivative represented by the structural formula (100).
Figure 10B:
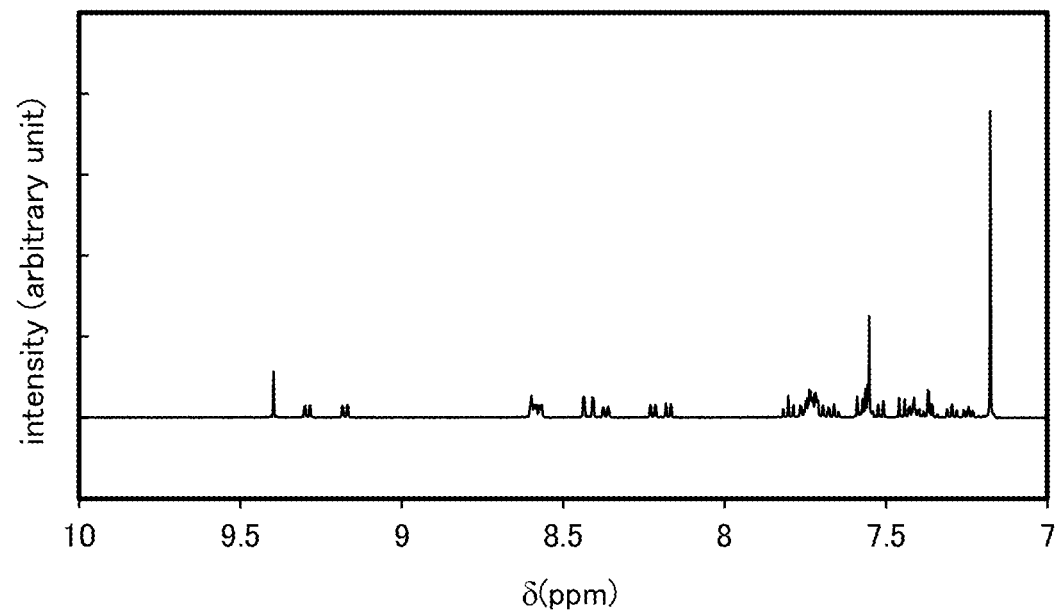

Analysis results by nuclear magnetic resonance spectroscopy ($^1$H-NMR) of the yellow powdered solid obtained in the above step will be described below. $^1$H-NMR charts are shown in FIGS. 10A and 10B. FIG. 10B is a chart in which the range from 7.0 (ppm) to 10 (ppm) on the horizontal axis (δ) in FIG. 10A is enlarged. These results show that 2PCCzPDBq (represented by the structural formula (100)) was obtained in the above step.

δ=7.32 (t, J=5.7 Hz, 1H), 7.37 (t, J=8.0 Hz, 1H), 7.43-7.53 (m, 5H), 7.58-7.66 (m, 6H), 7.72-7.89 (m, 8H), 8.25 (d, J=7.4 Hz, 1H), 8.30 (d, J=8.1 Hz, 1H), 8.44 (d, J=7.5 Hz, 1H), 8.50 (d, J=5.4 Hz, 2H), 8.64-8.67 (m, 3H), 9.25 (d, J=8.0 Hz, 1H), 9.37 (d, J=6.3 Hz, 1H), 9.47 (s, 1H).

Figure 11:
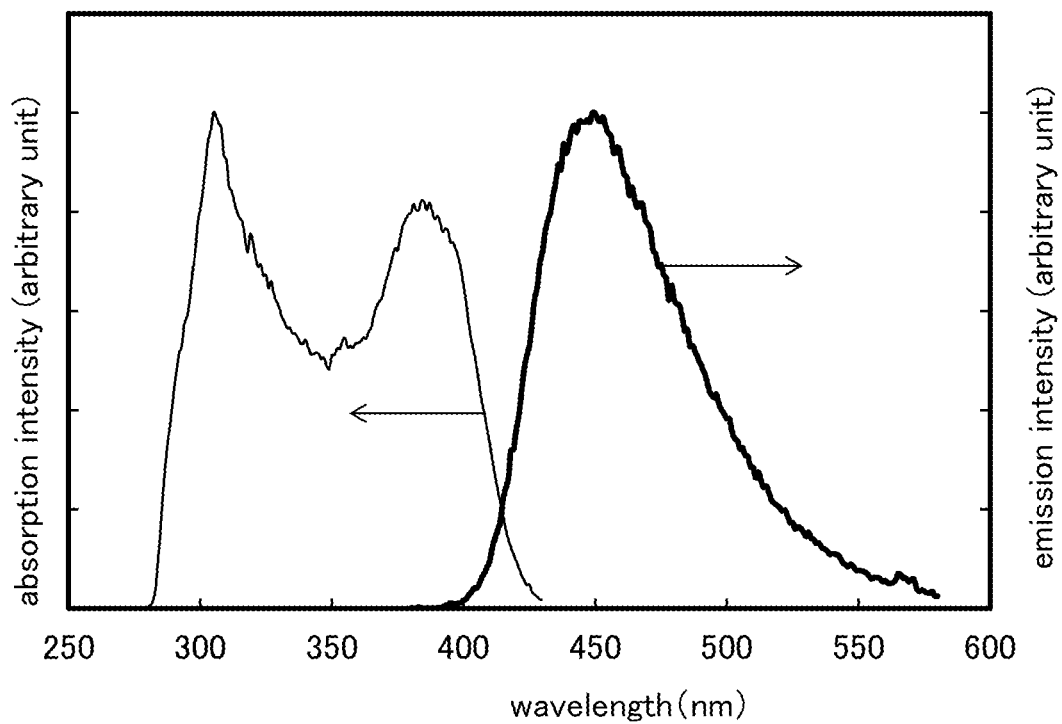
FIG. 11 shows the ultraviolet-visible absorption spectrum and the emission spectrum of the dibenzo[f,h]quinoxaline derivative represented by the structural formula (100).
Figure 12:
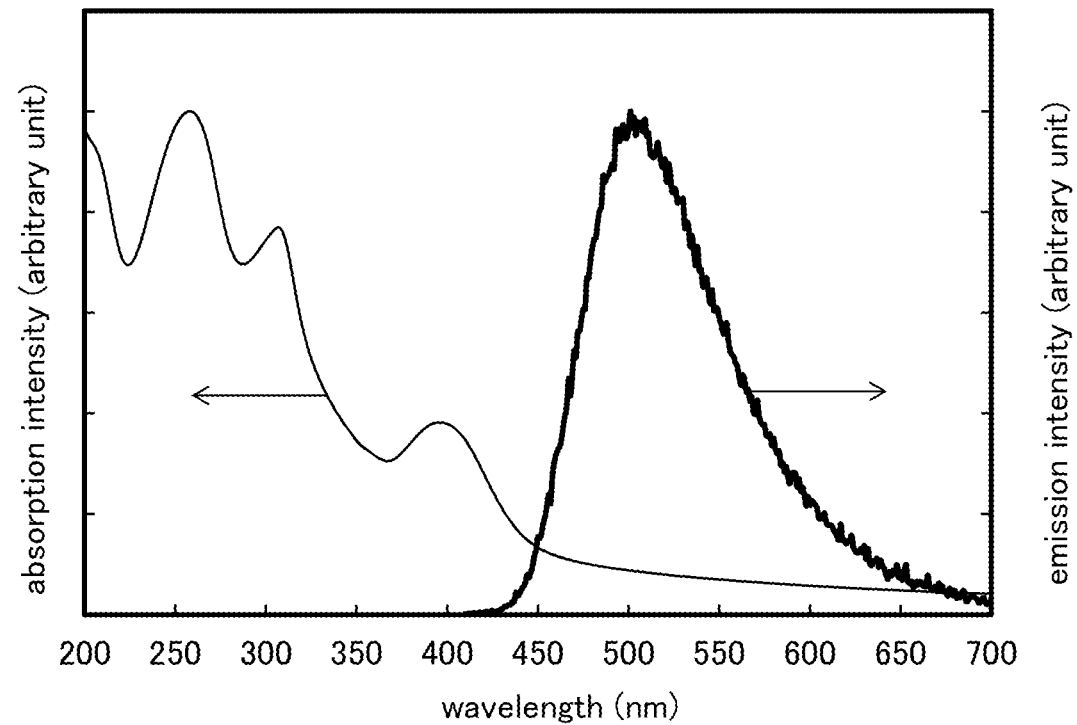
FIG. 12 shows the ultraviolet-visible absorption spectrum and the emission spectrum of the dibenzo[f,h]quinoxaline derivative represented by the structural formula (100).

Then, FIG. 11 shows the absorption spectrum and the emission spectrum of 2PCCzPDBq in a toluene solution of 2PCCzPDBq, and FIG. 12 shows the absorption spectrum and the emission spectrum of 2PCCzPDBq in a thin film of 2PCCzPDBq. The spectra were measured with a UV-visible spectrophotometer (V550, produced by JASCO Corporation). The spectra of 2PCCzPDBq in the toluene solution of 2PCCzPDBq were measured with the toluene solution of 2PCCzPDBq put in a quartz cell. The spectra of 2PCCzPDBq in the thin film of 2PCCzPDBq were measured with a sample fabricated by deposition of 2PCCzPDBq on a quartz substrate by evaporation. Note that in the case of the absorption spectrum of 2PCCzPDBq in the toluene solution of 2PCCzPDBq, the absorption spectrum obtained by subtraction of the absorption spectra of the quartz cell and toluene from the measured spectrum is shown, and in the case of the absorption spectrum of 2PCCzPDBq in the thin film of 2PCCzPDBq, the absorption spectrum obtained by subtraction of the absorption spectrum of the quartz substrate from the measured spectrum is shown.

As shown in FIG. 11, in the case of 2PCCzPDBq in the toluene solution of 2PCCzPDBq, the absorption peaks were observed at approximately 305 nm and 385 nm, and the emission wavelength peak was observed at 450 nm (excitation wavelength: 305 nm). As shown in FIG. 12, in the case of 2PCCzPDBq in the thin film of 2PCCzPDBq, the absorption peaks were observed at approximately 209 nm, 258 nm, 307 nm, 336 nm, and 396 nm, and the emission wavelength peak was observed at 502 nm (excitation wavelength: 396 nm).

Example 2

Synthesis Example 2>>

In this example, as a synthesis method of one embodiment of the present invention, a synthesis method of 2-{3-[3-(N-phenyl-9H-carbazol-3-yl)-9H-carbazol-9-yl]phenyl}dibenzo[f,h]quinoxaline (abbreviation: 2mPCCzPDBq, represented by the structural formula (101)) will be described. The structure of 2mPCCzPDBq is shown below.

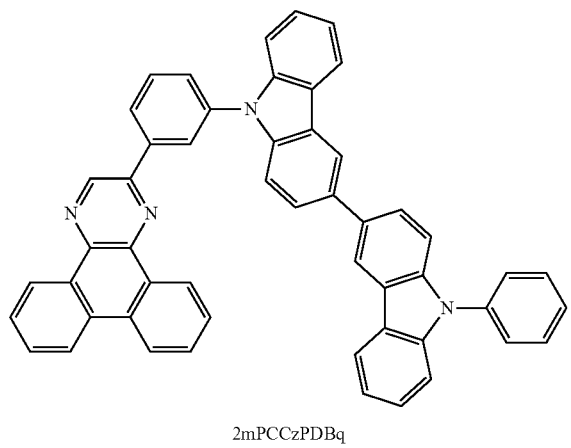

(101)

2mPCCzPDBq

Synthesis of 2mPCCzPDBq

First, 1.7 g (5.0 mmol) of 2-(3-chlorophenyl)dibenzo[f,h]quinoxaline, 2.0 g (5.0 mmol) of 3-(9-phenyl-9H-carbazol-3-yl)-9H-carbazole, 0.96 g (10 mmol) of sodium-tert-butoxide, and 41 mg (0.10 mmol) of 2-dicyclohexylphosphino-2',6'-dimethoxybiphenyl (abbreviation: S-Phos) were put in a 200-mL three-neck flask and mixed, and the air in the flask was replaced with nitrogen. To this mixture was added 25 mL of mesitylene, and the resulting mixture was degassed by being stirred while the pressure in the flask was reduced.

Then, 29 mg (0.050 mmol) of bis(dibenzylideneacetone)palladium(0) (abbreviation: Pd(dba)$_2$) was added to the mixture. This mixture was stirred at 150° C. for 5 hours under a nitrogen stream, so that a solid was precipitated. The precipitated solid was collected by suction filtration. The collected solid was dissolved in approximately 400 mL of hot toluene, and this solution was suction-filtered through a stack of Celite and alumina. The resulting filtrate was concentrated to give a solid. The solid was recrystallized with toluene to give 2.8 g of a yellow powder, which was the target substance, in a yield of 79%.

By a train sublimation method, 2.2 g of the obtained yellow powdered solid, which was the target substance, was purified. The sublimation purification was carried out at 360° C. under a pressure of 2.5 Pa with a flow rate of an argon gas at 10 mL/min. After the sublimation purification, 1.2 g of a yellow glassy solid of 2mPCCzPDBq was obtained at a collection rate of 55%. The synthesis scheme of this step is shown in the following scheme (b-1).

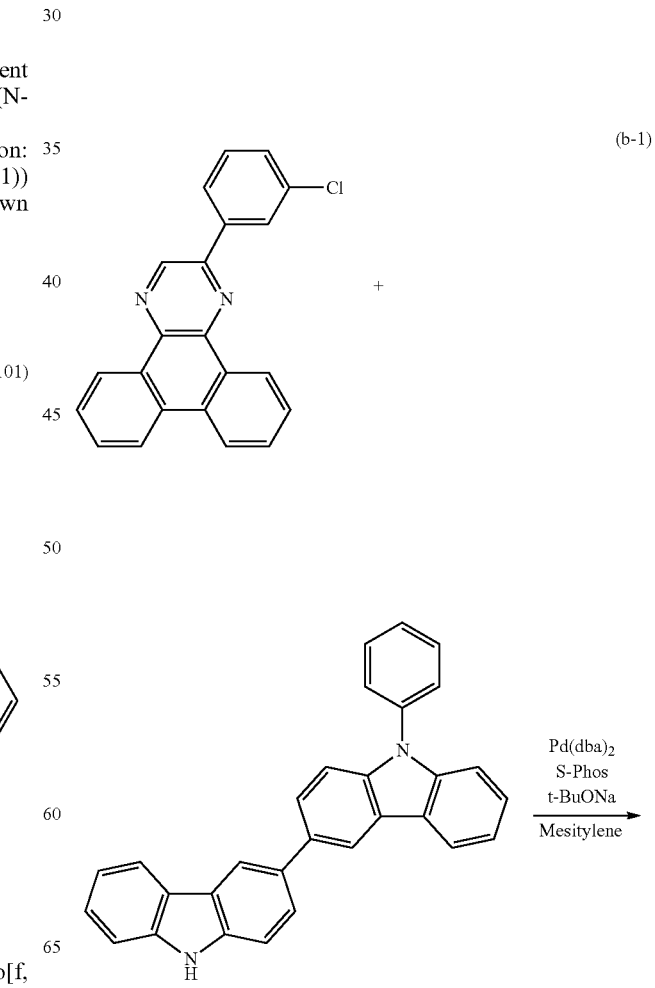

(b-1)

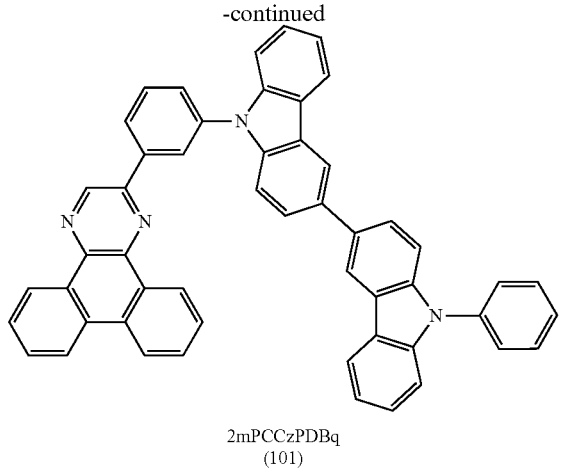

2mPCCzPDBq
(101)

Figure 13A:
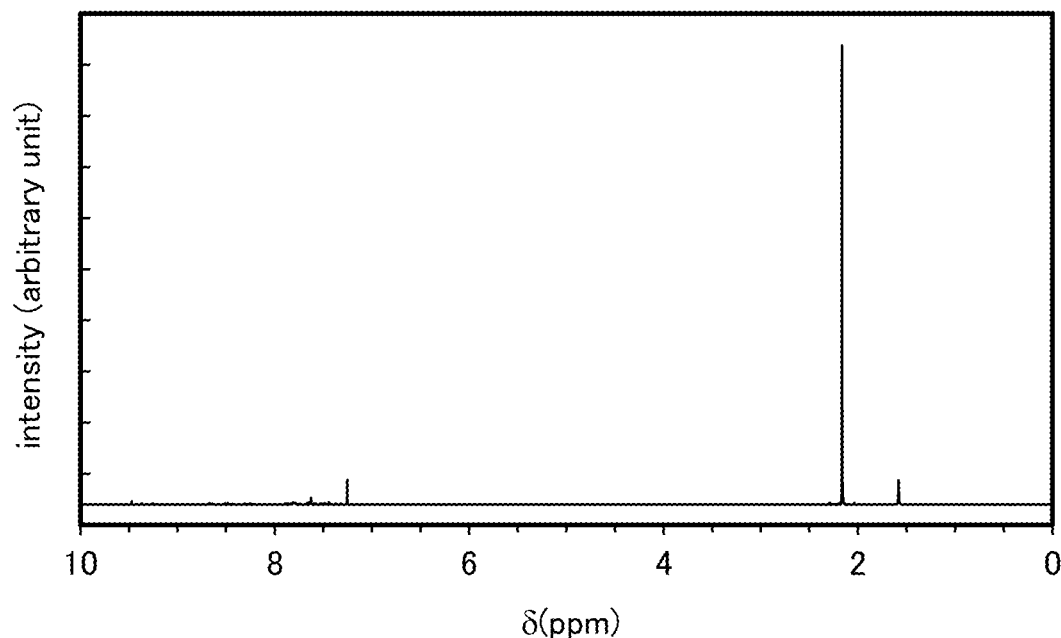
FIGS. 13A and 13B are $^1$H-NMR charts of a dibenzo[f,h]quinoxaline derivative represented by the structural formula (101).
Figure 13B:
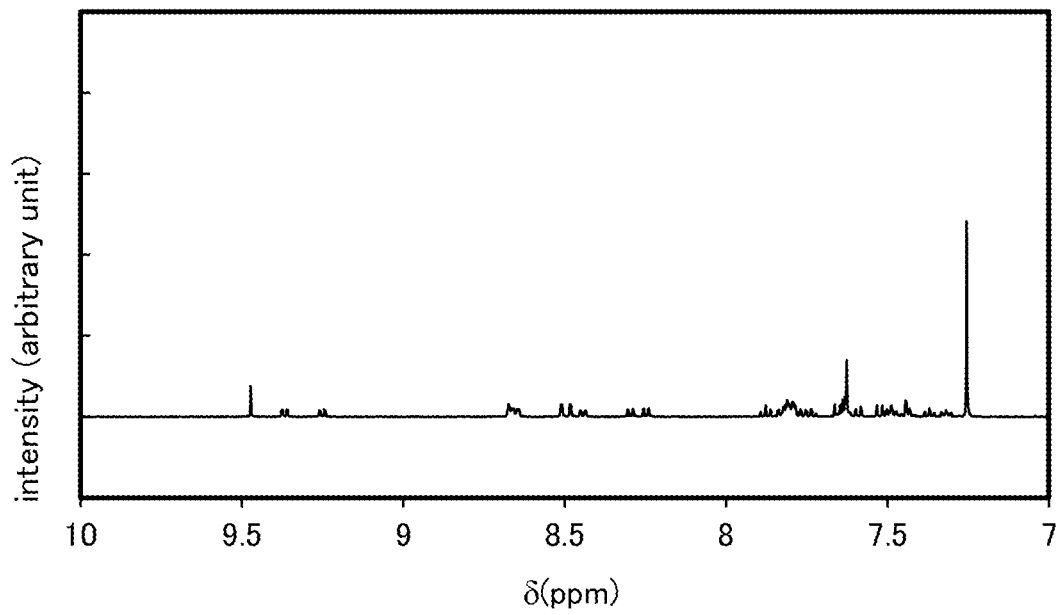

Analysis results by nuclear magnetic resonance spectroscopy ($^1$H-NMR) of the yellow powdered solid obtained in the above step will be described below. $^1$H-NMR charts are shown in FIGS. 13A and 13B. FIG. 13B is a chart in which the range from 7.0 (ppm) to 10 (ppm) on the horizontal axis (δ) in FIG. 13A is enlarged. These results show that 2-{3-[3-(N-phenyl-9H-carbazol-3-yl)-9H-carbazol-9-yl]phenyl}dibenzo[f,h]quinoxaline (abbreviation: 2mPCCzPDBq, represented by the structural formula (101)) was obtained in the above step.

$^1$H-NMR (CDCl$_3$, 500 MHz): δ (ppm)=7.31-7.54 (m, 7H), 7.58-7.67 (m, 6H), 7.73-7.90 (m, 8H), 8.25 (d, J=8.0 Hz, 1H), 8.30 (d, J=8.1 Hz, 1H), 8.45 (d, J=6.3 Hz, 1H), 8.49 (d, J=3.7 Hz, 2H), 8.65-8.68 (m, 3H), 9.25 (d, J=2.0 Hz, 1H), 9.37 (d, J=6.9 Hz, 1H), 9.48 (s, 1H).

Figure 14:
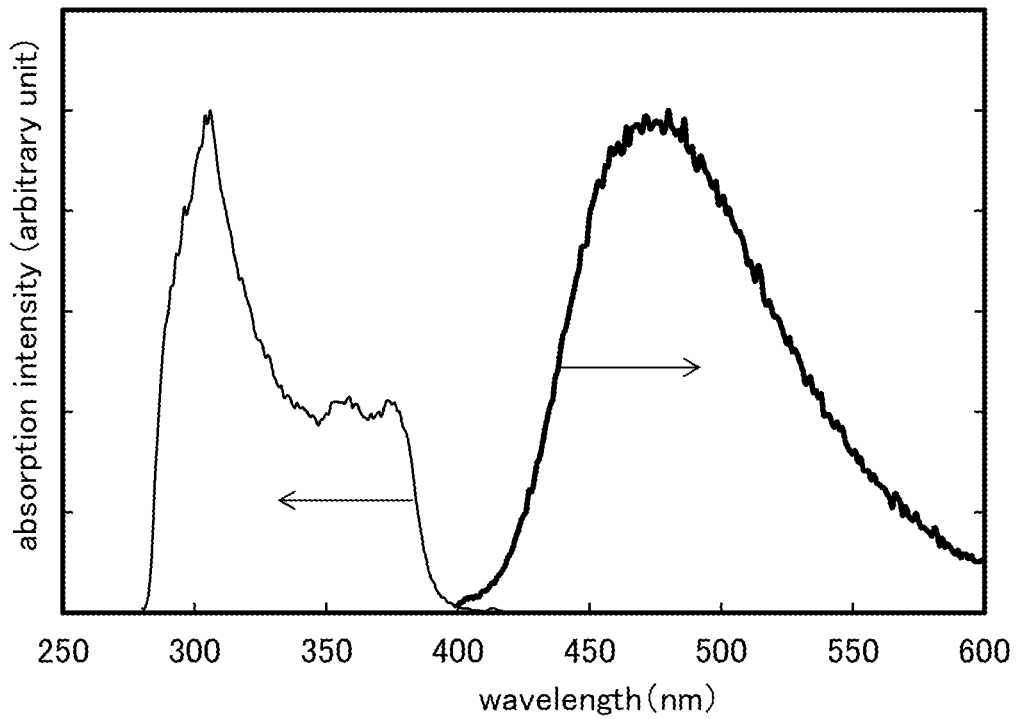
FIG. 14 shows the ultraviolet-visible absorption spectrum and the emission spectrum of the dibenzo[f,h]quinoxaline derivative represented by the structural formula (101).
Figure 15:
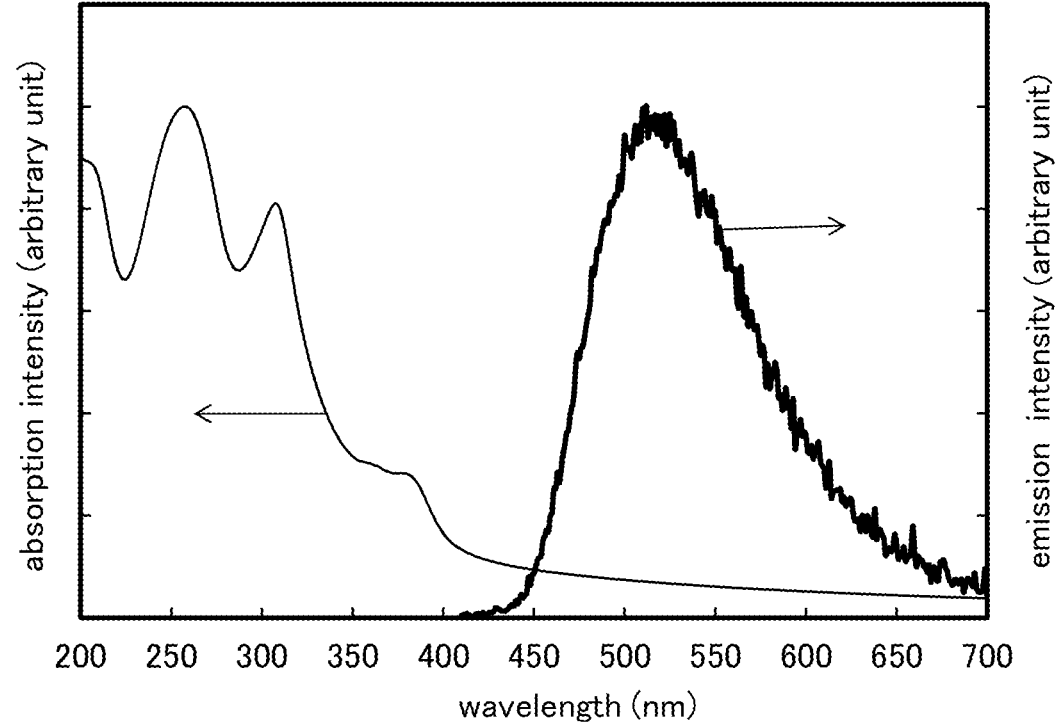
FIG. 15 shows the ultraviolet-visible absorption spectrum and the emission spectrum of the dibenzo[f,h]quinoxaline derivative represented by the structural formula (101).

Then, FIG. 14 shows the absorption spectrum and the emission spectrum of 2mPCCzPDBq in a toluene solution of 2mPCCzPDBq, and FIG. 15 shows the absorption spectrum and the emission spectrum of 2mPCCzPDBq in a thin film of 2mPCCzPDBq. The spectra were measured with a UV-visible spectrophotometer (V550, produced by JASCO Corporation). The spectra of 2mPCCzPDBq in the toluene solution of 2mPCCzPDBq were measured with the toluene solution of 2mPCCzPDBq put in a quartz cell. The spectra of 2mPCCzPDBq in the thin film of 2mPCCzPDBq were measured with a sample fabricated by deposition of 2mPCCzPDBq on a quartz substrate by evaporation. Note that in the case of the absorption spectrum of 2mPCCzPDBq in the toluene solution of 2mPCCzPDBq, the absorption spectrum obtained by subtraction of the absorption spectra of the quartz cell and toluene from the measured spectrum is shown, and in the case of the absorption spectrum of 2mPCCzPDBq in the thin film of 2mPCCzPDBq, the absorption spectrum obtained by subtraction of the absorption spectrum of the quartz substrate from the measured spectrum is shown.

As shown in FIG. 14, in the case of 2mPCCzPDBq in the toluene solution of 2mPCCzPDBq, the absorption peaks were observed at approximately 305 nm and 374 nm, and the emission wavelength peak was observed at 480 nm (excitation wavelength: 305 nm). As shown in FIG. 15, in the case of 2mPCCzPDBq in the thin film of 2mPCCzPDBq, the absorption peaks were observed at approximately 208 nm, 257 nm, 308 nm, 361 nm, and 379 nm, and the emission wavelength peak was observed at 515 nm (excitation wavelength: 380 nm).

Example 3

Synthesis Example 3

In this example, as a synthesis method of one embodiment of the present invention, a synthesis method of 2-{4-[2-(N-phenyl-9H-carbazol-3-yl)-9H-carbazol-9-yl]phenyl}dibenzo[f,h]quinoxaline (abbreviation: 2PCCzPDBq-02, represented by the structural formula (102)) will be described. The structure of 2PCCzPDBq-02 is shown below.

(102)

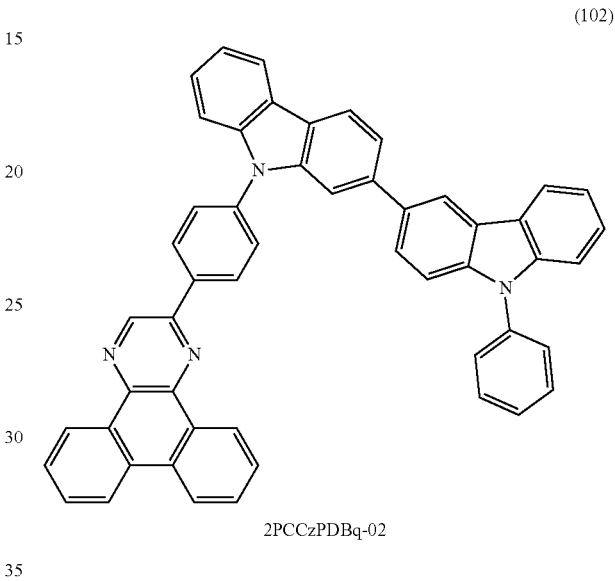

2PCCzPDBq-02

Synthesis of 2PCCzPDBq-02

First, 1.4 g (4.2 mmol) of 2-(4-chlorophenyl)dibenzo[f,h]quinoxaline, 1.7 g (4.2 mmol) of 2-(9-phenyl-9H-carbazol-3-yl)-9H-carbazole, 0.81 g (8.4 mmol) of sodium-tert-butoxide, and 34 mg (0.10 mmol) of 2-dicyclohexylphosphino-2',6'-dimethoxybiphenyl (abbreviation: S-Phos) were put in a 200-mL three-neck flask and mixed, and the air in the flask was replaced with nitrogen. To this mixture was added 21 mL of mesitylene, and the resulting mixture was degassed by being stirred while the pressure in the flask was reduced.

Then, 24 mg (0.042 mmol) of bis(dibenzylideneacetone)palladium(0) (abbreviation: Pd(dba)$_2$) was added to the mixture. This mixture was stirred at 150° C. for 5 hours under a nitrogen stream, so that a solid was precipitated. The precipitated solid was collected by suction filtration. The collected solid was dissolved in approximately 400 mL of hot toluene, and this solution was suction-filtered through a stack of Celite and alumina. The resulting filtrate was concentrated to give a solid. The solid was recrystallized with toluene to give 2.5 g of a yellow powder, which was the target substance, in a yield of 84%.

By a train sublimation method, 2.0 g of the obtained yellow powdered solid, which was the target substance, was purified. The sublimation purification was carried out at 390° C. under a pressure of 3.7 Pa with a flow rate of an argon gas at 10 mL/min. After the sublimation purification, 1.7 g of a yellow glassy solid of 2PCCzPDBq-02 was obtained at a collection rate of 85%. The synthesis scheme of this step is shown in the following scheme (c-1).

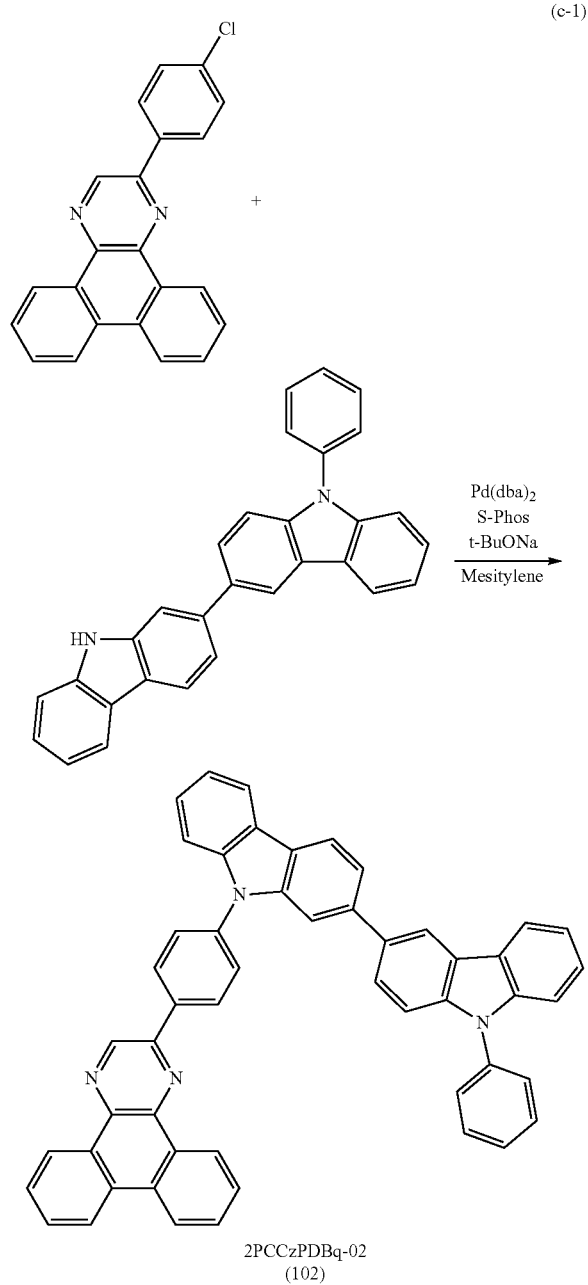

2PCCzPDBq-02
(102)

Figure 16A:
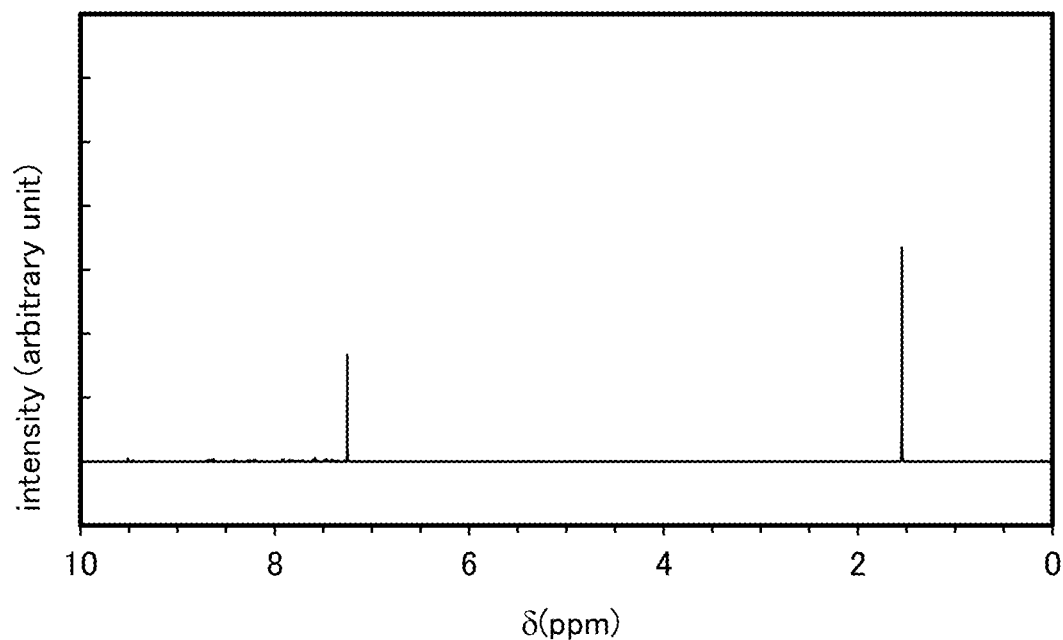
FIGS. 16A and 16B are $^1$H-NMR charts of a dibenzo[f,h]quinoxaline derivative represented by the structural formula (102).
Figure 16B:
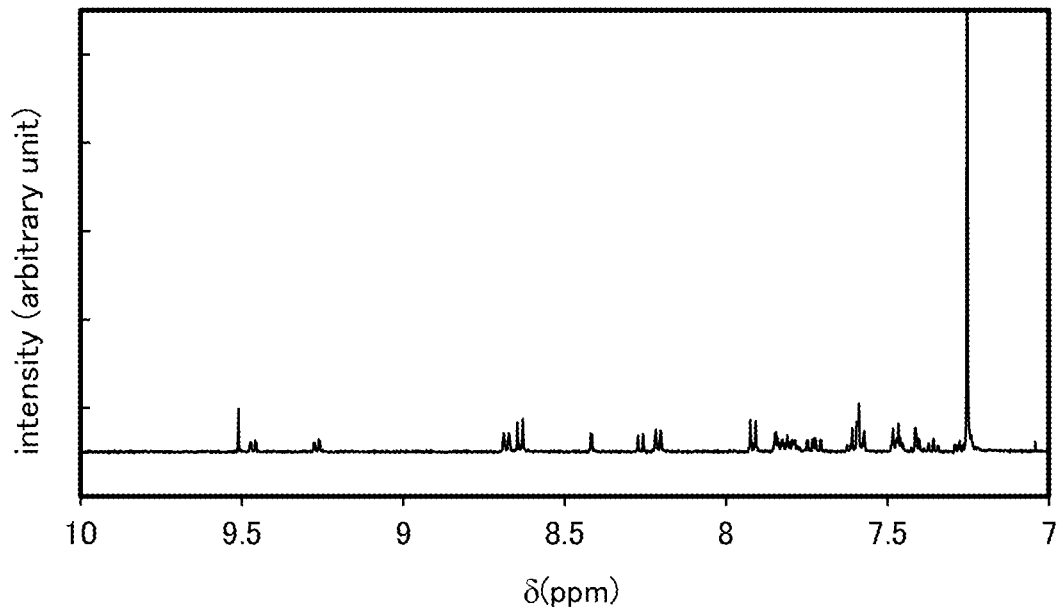

Analysis results by nuclear magnetic resonance spectroscopy ($^1$H-NMR) of the yellow powdered solid obtained in the above step will be described below. $^1$H-NMR charts are shown in FIGS. 16A and 16B. FIG. 16B is a chart in which the range from 7.0 (ppm) to 10 (ppm) on the horizontal axis (δ) in FIG. 16A is enlarged. These results show that 2-{4-[2-(N-phenyl-9H-carbazol-3-yl)-9H-carbazol-9-yl]phenyl}dibenzo[f,h]quinoxaline (abbreviation: 2PCCzPDBq-02, represented by the structural formula (102)) was obtained in the above step.

δ=7.25-7.48 (m, 7H), 7.71-7.75 (m, 2H), 7.71-7.75 (m, 5H), 7.91 (d, J=8.6 Hz, 2H), 8.21 (d, J=7.4 Hz, 1H), 8.26 (d, J=8.0 Hz, 2H), 8.42 (sd, J=1.7 Hz, 2H), 8.63-8.69 (m, 4H), 9.27 (d, J=8.0 Hz, 1H), 9.46 (d, J=6.3 Hz, 1H), 9.51 (s, 1H).

Figure 17:
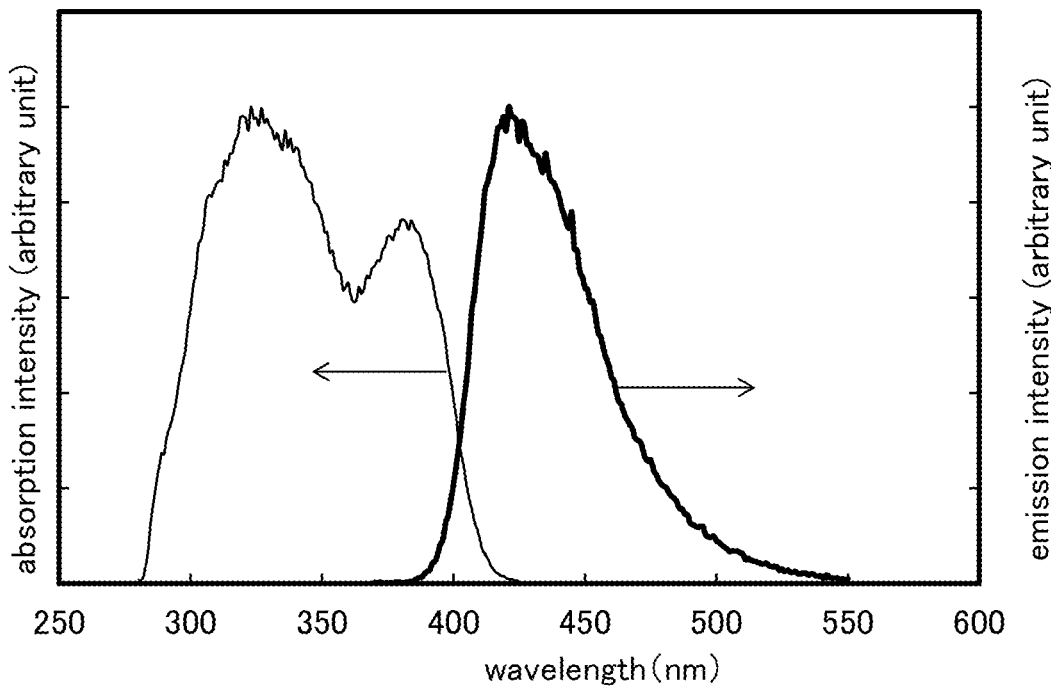
FIG. 17 shows the ultraviolet-visible absorption spectrum and the emission spectrum of the dibenzo[f,h]quinoxaline derivative represented by the structural formula (102).
Figure 18:
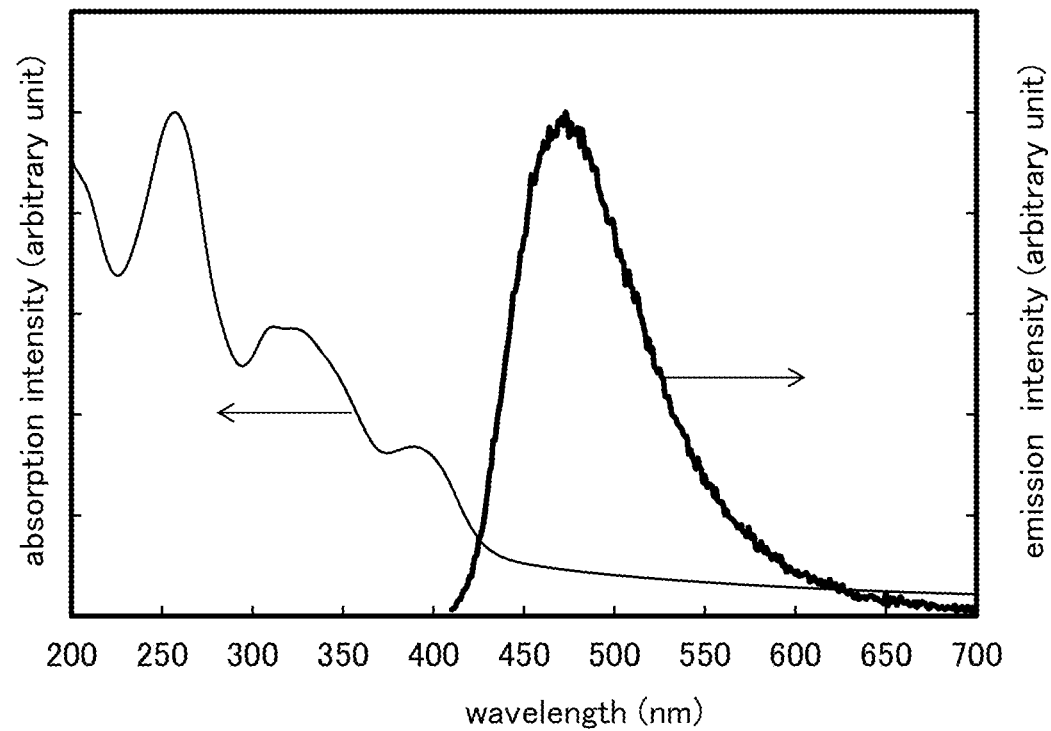
FIG. 18 shows the ultraviolet-visible absorption spectrum and the emission spectrum of the dibenzo[f,h]quinoxaline derivative represented by the structural formula (102).

Then, FIG. 17 shows the absorption spectrum and the emission spectrum of 2PCCzPDBq-02 in a toluene solution of 2PCCzPDBq-02, and FIG. 18 shows the absorption spectrum and the emission spectrum of 2PCCzPDBq-02 in a thin film of 2PCCzPDBq-02. The spectra were measured with a UV-visible spectrophotometer (V550, produced by JASCO Corporation). The spectra of 2PCCzPDBq-02 in the toluene solution of 2PCCzPDBq-02 were measured with the toluene solution of 2PCCzPDBq-02 put in a quartz cell. The spectra of 2PCCzPDBq-02 in the thin film of 2PCCzPDBq-02 were measured with a sample fabricated by deposition of 2PCCzPDBq-02 on a quartz substrate by evaporation. Note that in the case of the absorption spectrum of 2PCCzPDBq-02 in the toluene solution of 2PCCzPDBq-02, the absorption spectrum obtained by subtraction of the absorption spectra of the quartz cell and toluene from the measured spectrum is shown, and in the case of the absorption spectrum of 2PCCzPDBq-02 in the thin film of 2PCCzPDBq-02, the absorption spectrum obtained by subtraction of the absorption spectrum of the quartz substrate from the measured spectrum is shown.

As shown in FIG. 17, in the case of 2PCCzPDBq-02 in the toluene solution of 2PCCzPDBq-02, the absorption peaks were observed at approximately 323 nm and 381 nm, and the emission wavelength peak was observed at 421 nm (excitation wavelength: 320 nm). As shown in FIG. 18, in the case of 2PCCzPDBq-02 in the thin film of 2PCCzPDBq-02, the absorption peaks were observed at approximately 209 nm, 257 nm, 311 nm, 326 nm, 351 nm, and 389 nm, and the emission wavelength peak was observed at 473 nm (excitation wavelength: 396 nm).

Example 4

Synthesis Example 4

In this example, as a synthesis method of one embodiment of the present invention, a synthesis method of 2-{3-[2-(N-phenyl-9H-carbazol-3-yl)-9H-carbazol-9-yl]phenyl}dibenzo[f,h]quinoxaline (abbreviation: 2mPCCzPDBq-02, represented by the structural formula (103)) will be described. The structure of 2mPCCzPDBq-02 is shown below.

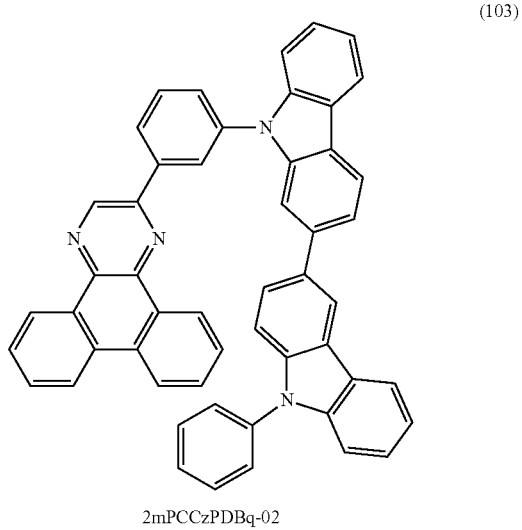 [SMILES: c1ccc(-n2c3ccccc3c3cc(-c4ccc5c6ccccc6n(-c6cccc(-c7cnc8c9ccccc9c9ccccc9c8n7)c6)c5c4)ccc32)cc1]

2mPCCzPDBq-02

Synthesis of 2mPCCzPDBq-02

First, 1.7 g (5.0 mmol) of 2-(3-chlorophenyl)dibenzo[f,h]quinoxaline, 2.0 g (5.0 mmol) of 2-(9-phenyl-9H-carbazol-3-yl)-9H-carbazole, 0.96 g (10 mmol) of sodium-tert-butoxide, and 41 mg (0.10 mmol) of 2-dicyclohexylphosphino-2',6'-dimethoxybiphenyl (abbreviation: S-Phos) were put in a 200-mL three-neck flask and mixed, and the air in the flask was replaced with nitrogen. To this mixture was added 25 mL of mesitylene, and the resulting mixture was degassed by being stirred while the pressure in the flask was reduced.

Then, 29 mg (0.050 mmol) of bis(dibenzylideneacetone)palladium(0) (abbreviation: Pd(dba)$_2$) was added to the mixture. This mixture was stirred at 150° C. for 4 hours under a nitrogen stream, so that a solid was precipitated. The precipitated solid was collected by suction filtration. The collected solid was dissolved in approximately 400 mL of hot toluene, and this solution was suction-filtered through a stack of Celite, alumina, and Florisil. The resulting filtrate was concentrated to give a solid. The solid was recrystallized with toluene to give 3.1 g of a white powder, which was the target substance, in a yield of 87%.

By a train sublimation method, 3.0 g of the obtained white powdered solid, which was the target substance, was purified. The sublimation purification was carried out at 360° C. under a pressure of 10 Pa with a flow rate of an argon gas at 5.0 mL/min. After the sublimation purification, 2.0 g of a yellow glassy solid of 2mPCCzPDBq-02 was obtained at a collection rate of 65%. The synthesis scheme of this step is shown in the following scheme (d-1).

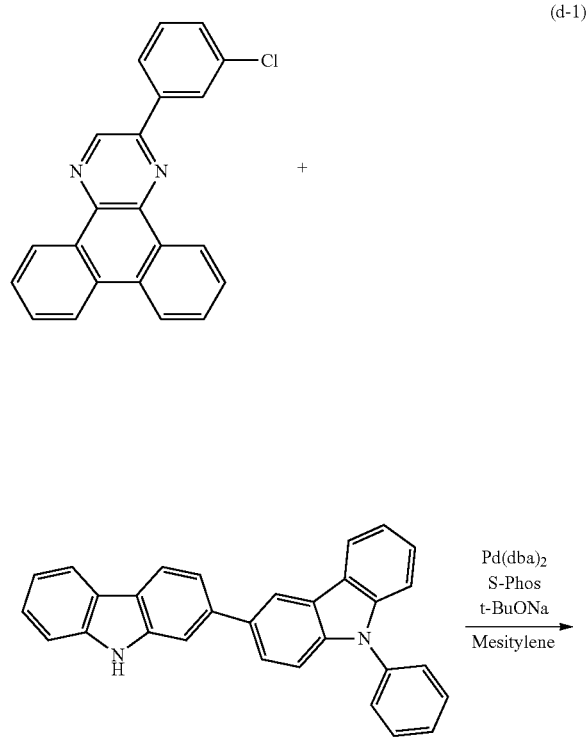

(d-1)

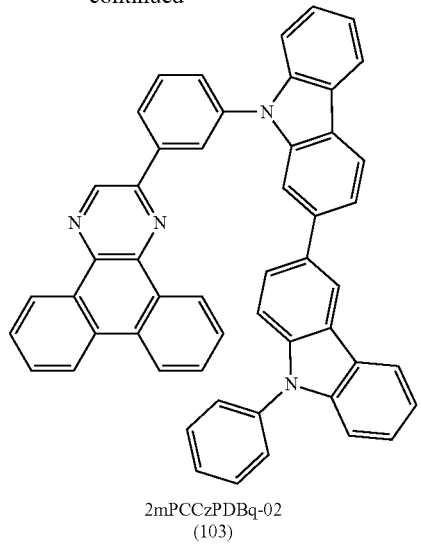

2mPCCzPDBq-02
(103)

Figure 19A:
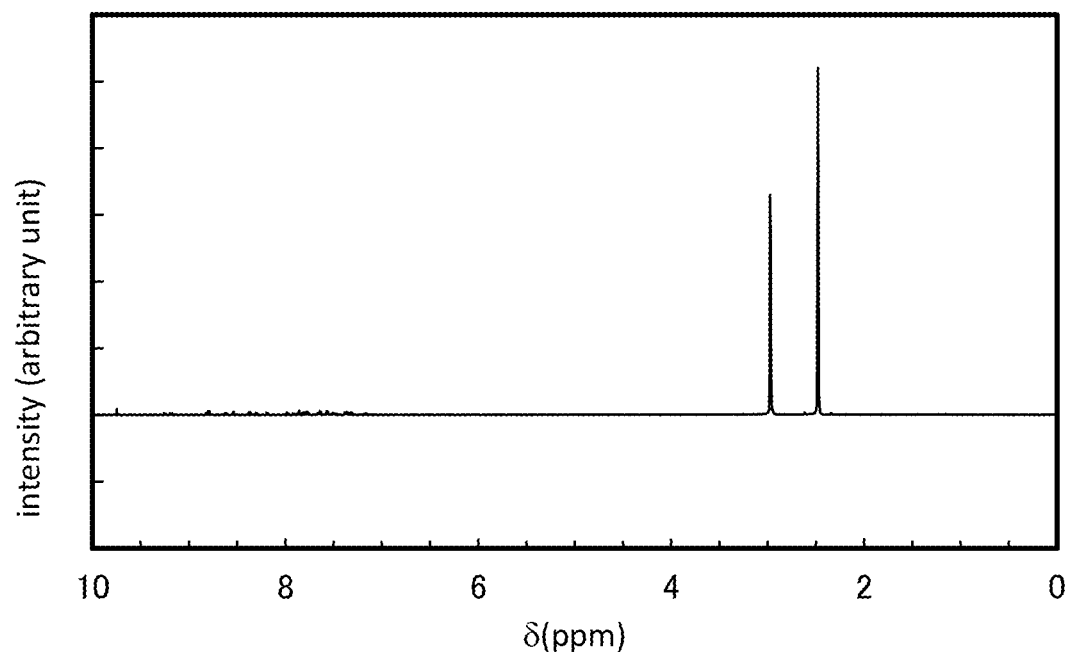
FIGS. 19A and 19B are $^1$H-NMR charts of a dibenzo[f,h]quinoxaline derivative represented by the structural formula (103).
Figure 19B:
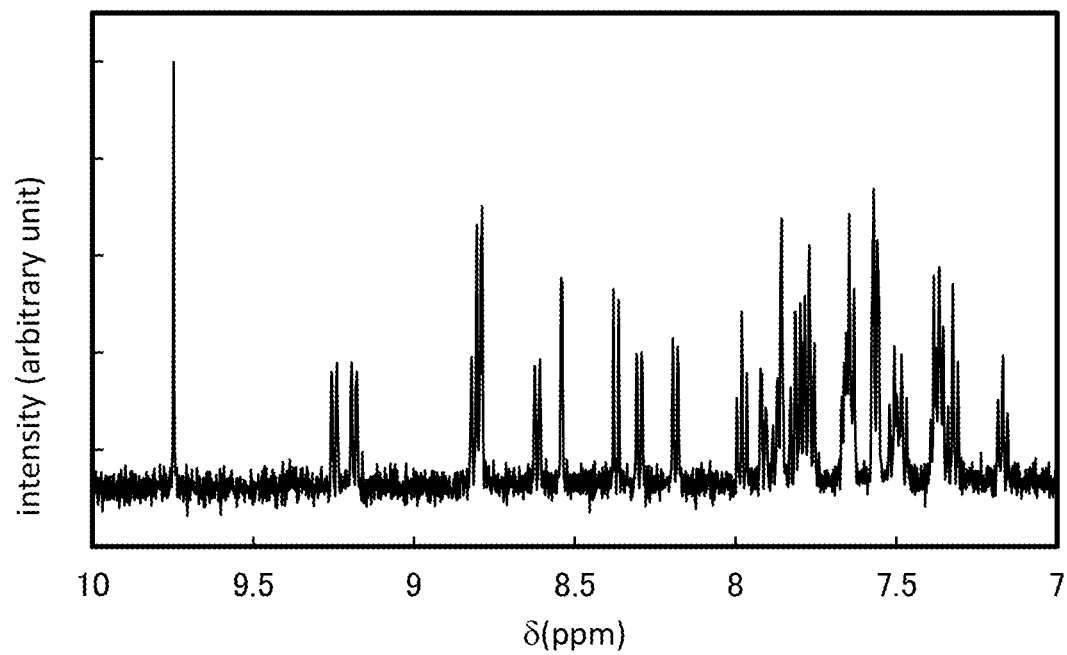

Analysis results by nuclear magnetic resonance spectroscopy ($^1$H-NMR) of the white powdered solid obtained in the above step will be described below. $^1$H-NMR charts are shown in FIGS. 19A and 19B. FIG. 19B is a chart in which the range from 7.0 (ppm) to 10 (ppm) on the horizontal axis (δ) in FIG. 19A is enlarged. These results show that 2mPCCzPDBq-02 (represented by the structural formula (103)) was obtained in the above step.

$^1$H-NMR (DMSO-d$^6$, 500 MHz): δ(ppm)=7.17 (t, J1=7.5 Hz, 1H), 7.31-7.39 (m, 4H), 7.47-7.52 (m, 2H), 7.56-7.57 (m, 3H), 7.63-7.66 (m, 3H), 7.75-7.92 (m, 7H), 7.98 (t, J1=2.5 Hz, 1H), 8.19 (d, J1=7.5 Hz, 1H), 8.30 (d, J1=7.5 Hz, 1H), 8.37 (d, J1=8.0 Hz, 1H), 8.54 (sd, J1=1.5 Hz, 1H), 8.62 (d, J1=8.0 Hz, 1H), 8.79-8.82 (m, 3H), 9.19 (d, J1=8.0 Hz, 1H), 9.25 (d, J1=9.0 Hz, 1H), 9.75 (s, 1H).

Figure 20:
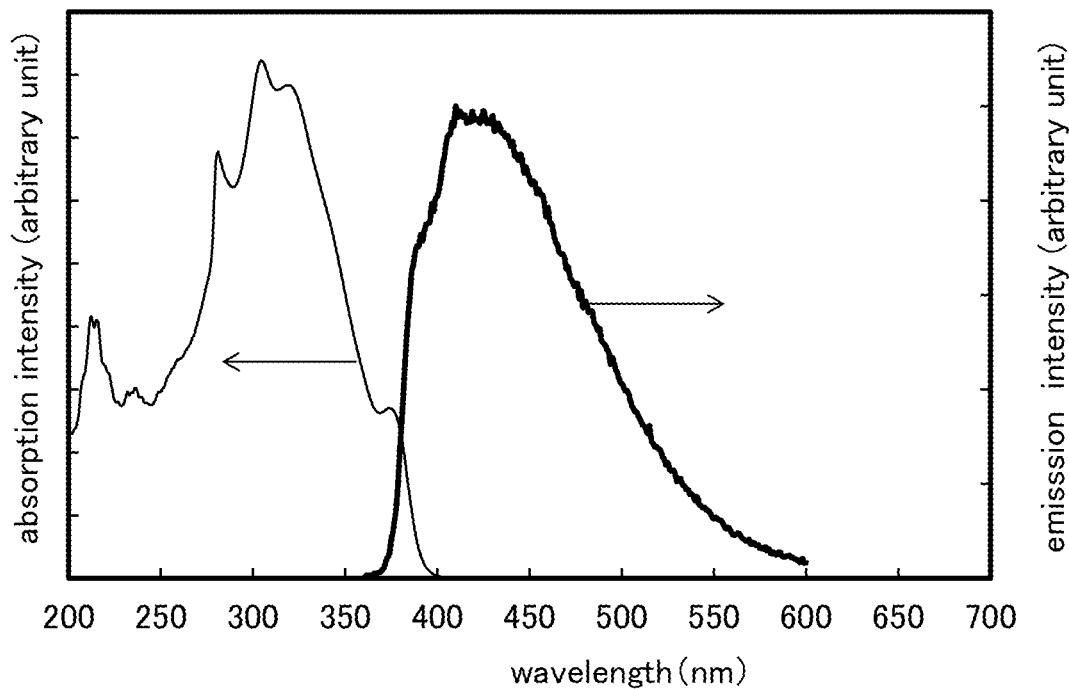
FIG. 20 shows the ultraviolet-visible absorption spectrum and the emission spectrum of the dibenzo[f,h]quinoxaline derivative represented by the structural formula (103).
Figure 21:
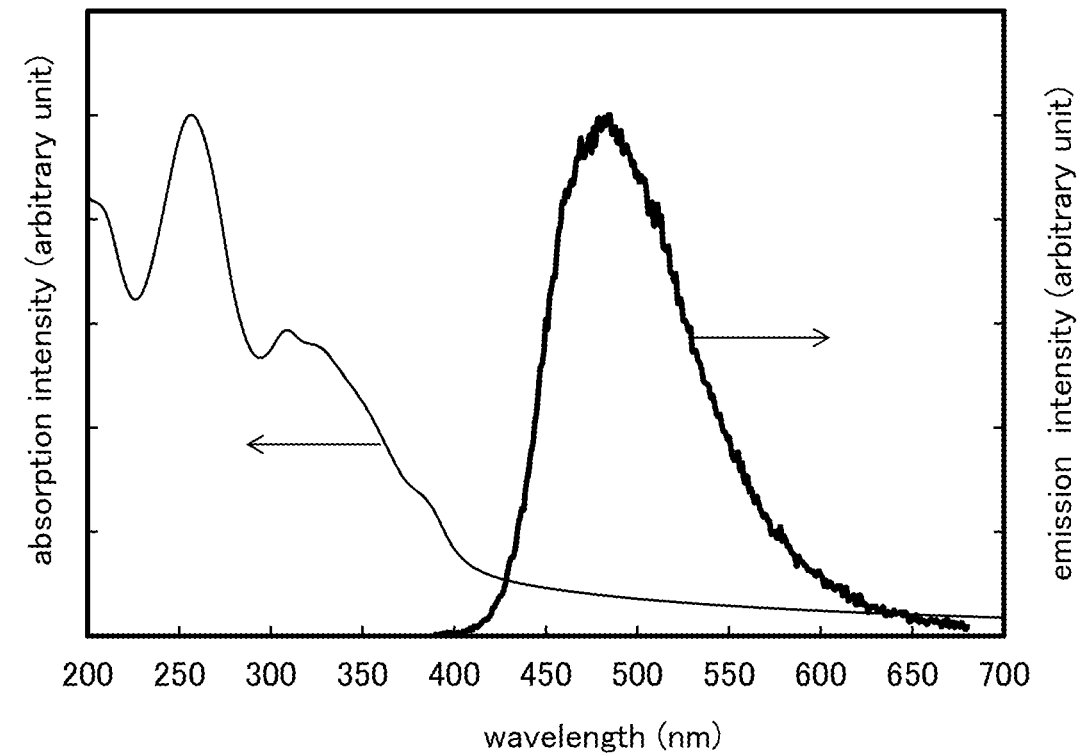
FIG. 21 shows the ultraviolet-visible absorption spectrum and the emission spectrum of the dibenzo[f,h]quinoxaline derivative represented by the structural formula (103).

Then, FIG. 20 shows the absorption spectrum and the emission spectrum of 2mPCCzPDBq-02 in a toluene solution of 2mPCCzPDBq-02, and FIG. 21 shows the absorption spectrum and the emission spectrum of 2mPCCzPDBq-02 in a thin film of 2mPCCzPDBq-02. The spectra were measured with a UV-visible spectrophotometer (V550, produced by JASCO Corporation). The spectra of 2mPCCzPDBq-02 in the toluene solution of 2mPCCzPDBq-02 were measured with the toluene solution of 2mPCCzPDBq-02 put in a quartz cell. The spectra of 2mPCCzPDBq-02 in the thin film of 2mPCCzPDBq-02 were measured with a sample fabricated by deposition of 2mPCCzPDBq-02 on a quartz substrate by evaporation. Note that in the case of the absorption spectrum of 2mPCCzPDBq-02 in the toluene solution of 2mPCCzPDBq-02, the absorption spectrum obtained by subtraction of the absorption spectra of the quartz cell and toluene from the measured spectrum is shown, and in the case of the absorption spectrum of 2mPCCzPDBq-02 in the thin film of 2mPCCzPDBq-02, the absorption spectrum obtained by subtraction of the absorption spectrum of the quartz substrate from the measured spectrum is shown.

As shown in FIG. 20, in the case of 2mPCCzPDBq-02 in the toluene solution of 2mPCCzPDBq-02, the absorption peaks were observed at approximately 281 nm, 305 nm, 319 nm, and 374 nm, and the emission wavelength peaks were observed at 389 nm and 410 nm. As shown in FIG. 21, in the case of 2mPCCzPDBq-02 in the thin film of 2mPCCzPDBq-02, the absorption peaks were observed at approximately 209 nm, 257 nm, 309 nm, 327 nm, 354 nm, and 386 nm, and the emission wavelength peak was observed at 484 nm (excitation wavelength: 381 nm).

Example 5

Figure 22:
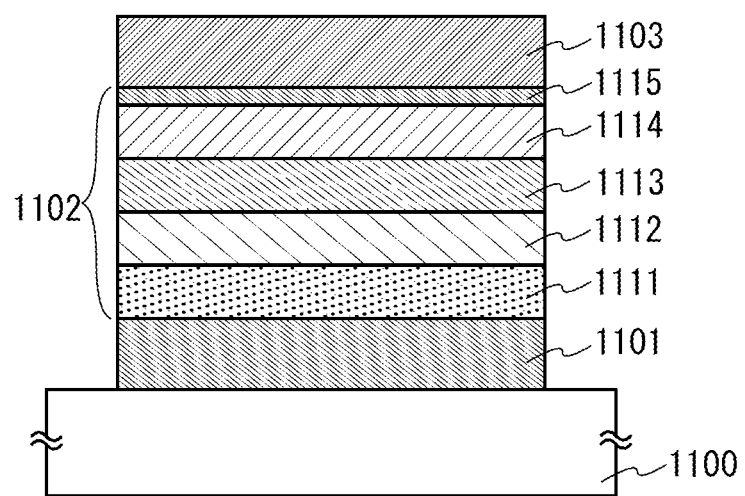
FIG. 22 illustrates the structure of each of a light-emitting element 1, a light-emitting element 2, and a comparative light-emitting element 3.
Figure 23:
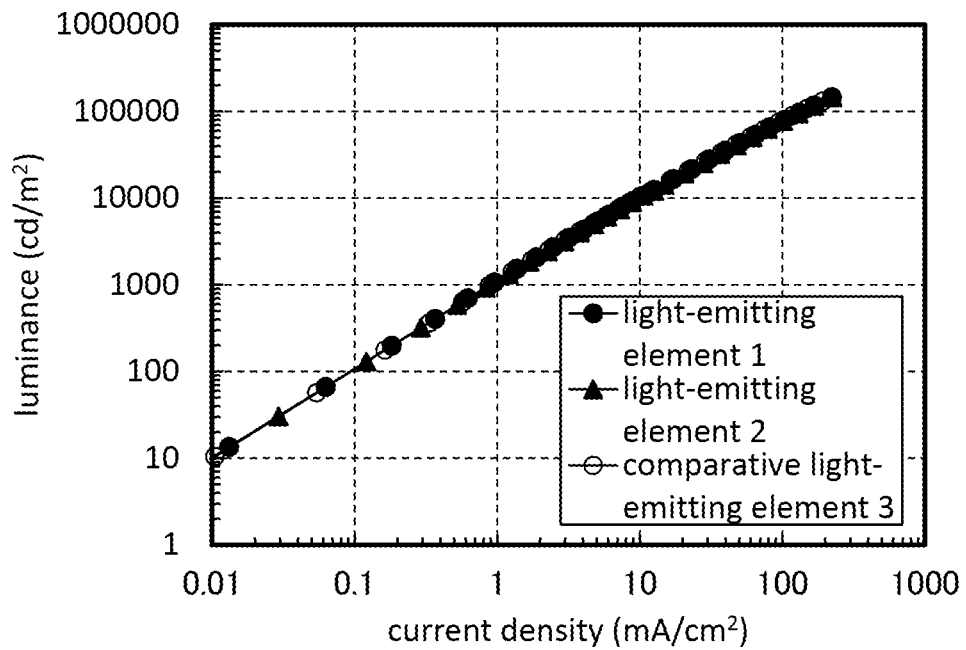
FIG. 23 shows current density-luminance characteristics of the light-emitting element 1, the light-emitting element 2, and the comparative light-emitting element 3.
Figure 24:
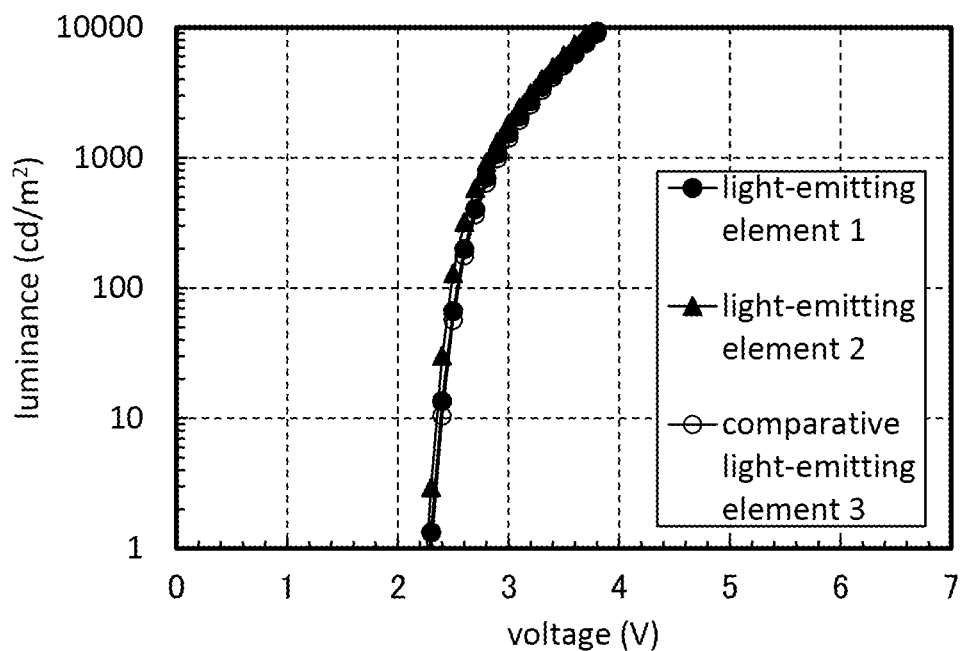
FIG. 24 shows voltage-luminance characteristics of the light-emitting element 1, the light-emitting element 2, and the comparative light-emitting element 3.
Figure 25:
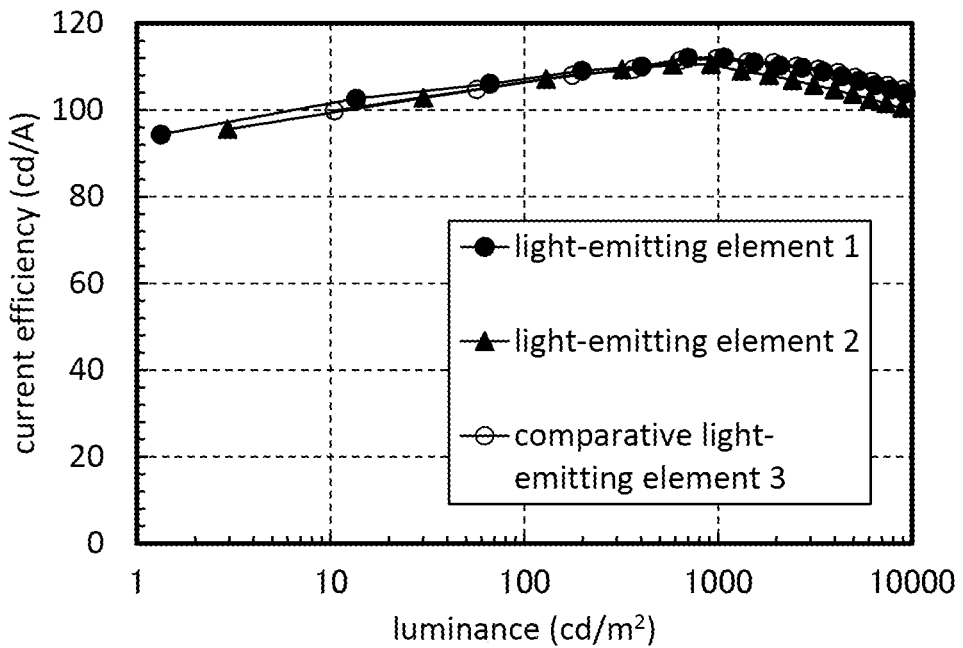
FIG. 25 shows luminance-current efficiency characteristics of the light-emitting element 1, the light-emitting element 2, and the comparative light-emitting element 3.
Figure 26:
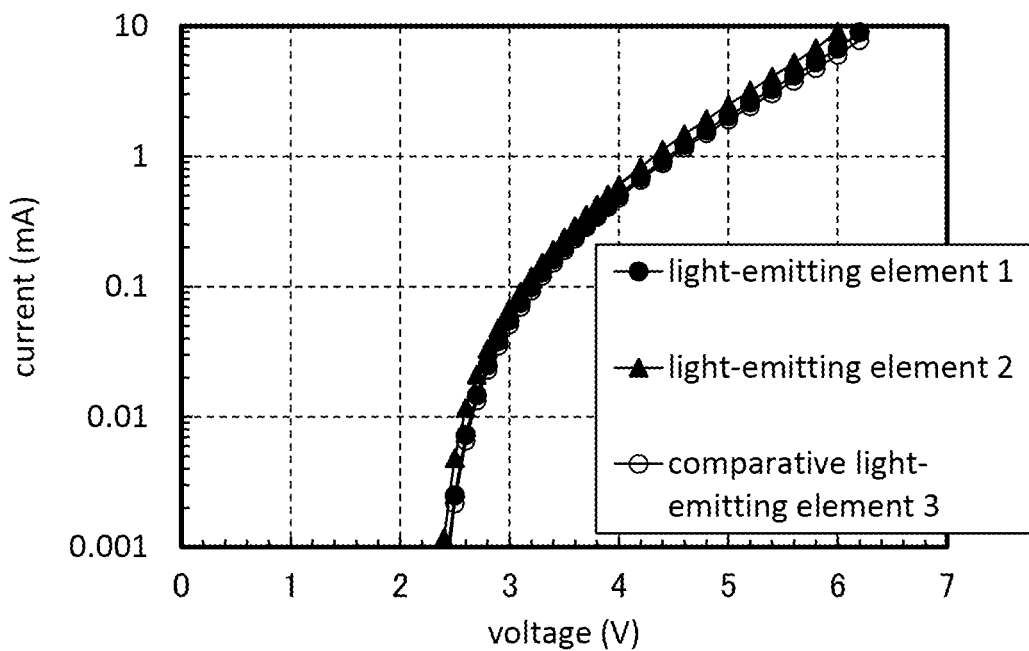
FIG. 26 shows voltage-current characteristics of the light-emitting element 1, the light-emitting element 2, and the comparative light-emitting element 3.

In this example, a light-emitting element 1 and a light-emitting element 2 each containing a dibenzo[f,h]quinoxaline derivative which is one embodiment of the present invention and a comparative light-emitting element 3 were fabricated. The structure of each light-emitting element will be described with reference to FIG. 22. Chemical formulae of materials used in this example are shown below.

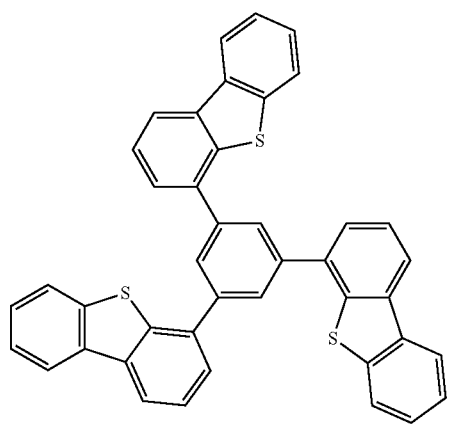

DBT3P-II

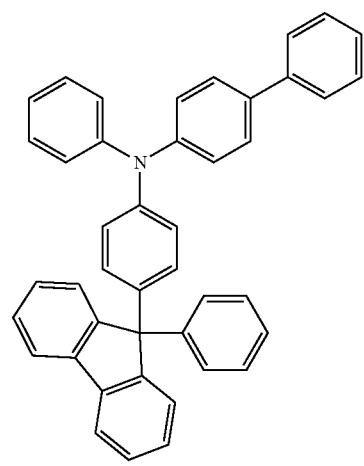

BPAFLP

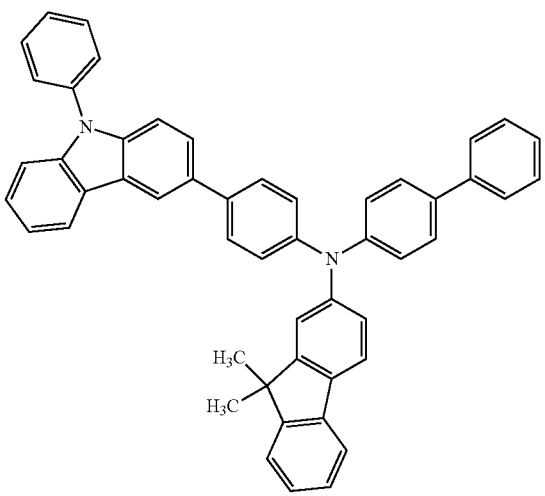

PCBBiF

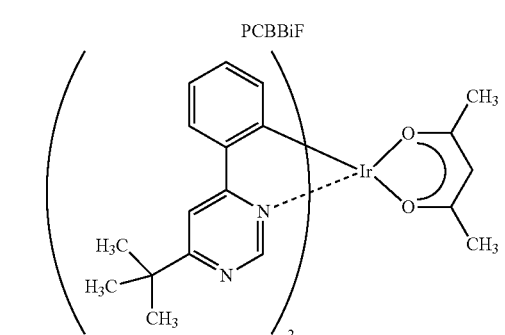

[Ir(tBuppm)$_2$(acac)]

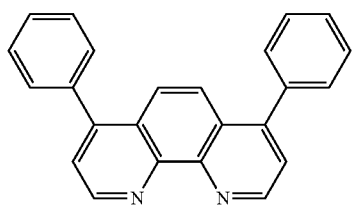

Bphen

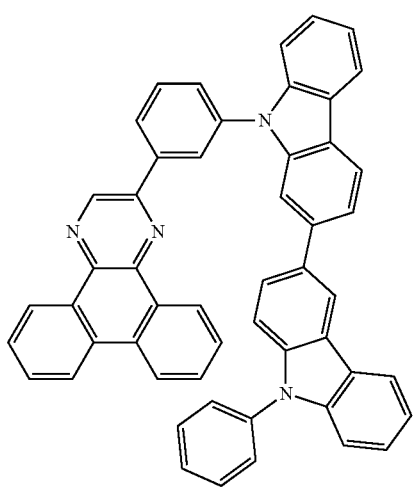

(103)

2mPCCzPDBq-02

-continued

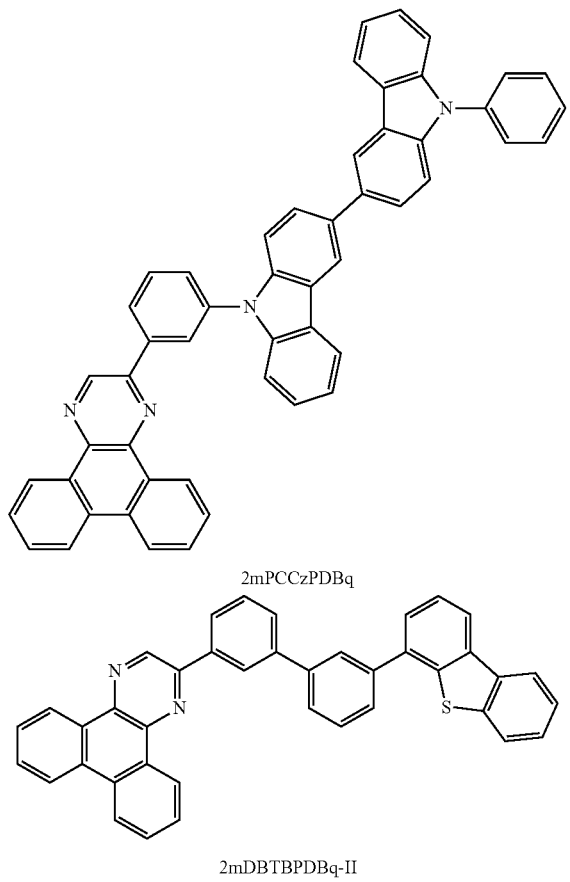

2mPCCzPDBq

2mDBTBPDBq-II

Fabrication of Light-Emitting Element 1, Light-Emitting Element 2, and Comparative Light-Emitting Element 3

First, indium tin oxide containing silicon oxide (ITSO) was deposited over a glass substrate 1100 by a sputtering method, so that a first electrode 1101 functioning as an anode was formed. Note that the thickness of the first electrode 1101 was set to be 110 nm and that the area of the first electrode 1101 was set to be 2 mm×2 mm.

Next, as pretreatment for forming the light-emitting element 1, the light-emitting element 2, and the comparative light-emitting element 3 over the substrate 1100, a surface of the substrate was washed with water, baking was performed at 200° C. for 1 hour, and then UV ozone treatment was performed for 370 seconds.

After that, the substrate 1100 was transferred into a vacuum evaporation apparatus in which the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case will be described where a hole-injection layer 1111, a hole-transport layer 1112, a light-emitting layer 1113, an electron-transport layer 1114, and an electron-injection layer 1115 which are included in an EL layer 1102 were sequentially formed by a vacuum evaporation method.

After reducing the pressure of the vacuum evaporation apparatus to $10^{-4}$ Pa, 1,3,5-tri(dibenzothiophen-4-yl)benzene (abbreviation: DBT3P-II) and molybdenum oxide were deposited by co-evaporation so that the mass ratio of DBT3P-II to molybdenum oxide was 4:2, whereby the hole-injection layer 1111 was formed on the first electrode 1101. The thickness of the hole-injection layer 1111 was set to be 20 nm. Note that co-evaporation is an evaporation method in which a plurality of different substances are concurrently vaporized from their respective evaporation sources.

Then, 4-phenyl-4'-(9-phenylfluoren-9-yl)triphenylamine (abbreviation: BPAFLP) was deposited by evaporation to a thickness of 20 nm, whereby the hole-transport layer 1112 was formed.

Next, the light-emitting layer 1113 was formed on the hole-transport layer 1112. In the case of the light-emitting element 1, 2-{3-[2-(N-phenyl-9H-carbazol-3-yl)-9H-carbazol-9-yl]phenyl}dibenzo[f,h]quinoxaline (abbreviation: 2mPCCzPDBq-02, represented by the structural formula (103)), N-(1,1'-biphenyl-4-yl)-N-[4-(9-phenyl-9H-carbazol-3-yl)phenyl]-9,9-dimethyl-9H-fluor en-2-amine (abbreviation: PCBBiF), and (acetylacetonato)bis(6-tert-butyl-4-phenylpyrimidinato)iridium(III) (abbreviation: [Ir(tBuppm)$_2$(acac)]) were deposited to a thickness of 20 nm by co-evaporation, so that the mass ratio of 2mPCCzPDBq-02 to PCBBiF and [Ir(tBuppm)$_2$(acac)] was 0.7:0.3:0.05. Then, 2mPCCzPDBq-02, PCBBiF, and [Ir(tBuppm)$_2$(acac)] were deposited to a thickness of 20 nm by co-evaporation, so that the mass ratio of 2mPCCzPDBq-02 to PCBBiF and [Ir(tBuppm)$_2$(acac)] was 0.8:0.2:0.05. In this manner, the light-emitting layer 1113 having a stacked structure and a thickness of 40 nm was formed.

In the case of the light-emitting element 2, 2-{3-[3-(N-phenyl-9H-carbazol-3-yl)-9H-carbazol-9-yl]phenyl}dibenzo[f,h]quinoxaline (abbreviation: 2mPCCzPDBq, represented by the structural formula (101)), PCBBiF, and [Ir(tBuppm)$_2$(acac)] were deposited to a thickness of 20 nm by co-evaporation, so that the mass ratio of 2mPCCzPDBq to PCBBiF and [Ir(tBuppm)$_2$(acac)] was 0.7:0.3:0.05. Then, 2mPCCzPDBq, PCBBiF, and [Ir(tBuppm)$_2$(acac)] were deposited to a thickness of 20 nm by co-evaporation, so that the mass ratio of 2mPCCzPDBq to PCBBiF and [Ir(tBuppm)$_2$(acac)] was 0.8:0.2:0.05. In this manner, the light-emitting layer 1113 having a stacked structure and a thickness of 40 nm was formed.

In the case of the comparative light-emitting element 3, 2-[3'-(dibenzothiophen-4-yl)biphenyl-3-yl]dibenzo[f,h]quinoxaline (abbreviation: 2mDBTBPDBq-II), PCBBiF, and [Ir(tBuppm)$_2$(acac)] were deposited to a thickness of 20 nm by co-evaporation, so that the mass ratio of 2mDBTBPDBq-II to PCBBiF and [Ir(tBuppm)$_2$(acac)] was 0.7:0.3:0.05. Then, 2mDBTBPDBq-II, PCBBiF, and [Ir(tBuppm)$_2$(acac)] were deposited to a thickness of 20 nm by co-evaporation, so that the mass ratio of 2mDBTBPDBq-II to PCBBiF and [Ir(tBuppm)$_2$(acac)] was 0.8:0.2:0.05. In this manner, the light-emitting layer 1113 having a stacked structure and a thickness of 40 nm was formed.

Then, in the case of the light-emitting element 1, 2mPCCzPDBq-02 was deposited to a thickness of 20 nm on the light-emitting layer 1113 by evaporation and bathophenanthroline (abbreviation: Bphen) was then deposited to a thickness of 10 nm by evaporation, whereby the electron-transport layer 1114 was formed. In the case of the light-emitting element 2, 2mPCCzPDBq was deposited to a thickness of 20 nm on the light-emitting layer 1113 by evaporation and bathophenanthroline (abbreviation: Bphen) was then deposited to a thickness of 10 nm by evaporation, whereby the electron-transport layer 1114 was formed. In the case of the comparative light-emitting element 3, 2mDBTBPDBq-II was deposited to a thickness of 20 nm on the light-emitting layer 1113 by evaporation and bathophenanthroline (abbreviation: Bphen) was then deposited to a thickness of 10 nm by evaporation, whereby the electron-transport layer 1114 was formed.

Furthermore, lithium fluoride was deposited to a thickness of 1 nm on the electron-transport layer 1114 by evaporation, whereby the electron-injection layer 1115 was formed.

Finally, aluminum was deposited to a thickness of 200 nm on the electron-injection layer 1115 by evaporation to form a second electrode 1103 serving as a cathode; thus, the light-emitting element 1, the light-emitting element 2, and the comparative light-emitting element 3 were fabricated. Note that in all the above evaporation steps, evaporation was performed by a resistance-heating method.

Table 1 shows the element structures of the light-emitting element 1, the light-emitting element 2, and the comparative light-emitting element 3 that were fabricated as described above.

TABLE 1

| | First Electrode | Hole-injection Layer | Hole-transport Layer | Light-emitting Layer | Electron-transport Layer | | Electron-injection Layer | Second Electrode |
|---|---|---|---|---|---|---|---|---|
| Light-emitting Element 1 | ITSO (110 nm) | DBT3P-II:MoOx (4:2 20 nm) | BPAFLP (20 nm) | * | 2mPCCzPDBq-02 (20 nm) | Bphen (10 nm) | LiF (1 nm) | Al (200 nm) |
| Light-emitting Element 2 | ITSO (110 nm) | DBT3P-II:MoOx (4:2 20 nm) | BPAFLP (20 nm) | ** | 2mPCCzPDBq (20 nm) | Bphen (10 nm) | LiF (1 nm) | Al (200 nm) |
| Comparative Light-emitting Element 3 | ITSO (110 nm) | DBT3P-II:MoOx (4:2 20 nm) | BPAFLP (20 nm) | *** | 2mDBTBPDBq-II (20 nm) | Bphen (10 nm) | LiF (1 nm) | Al (200 nm) |

* 2mPCCzPDBq-02:PCBBiF:[Ir(tBuppm)$_2$(acac)] (0.7:0.3:0.05 (20 nm)\0.8:0.2:0.05 (20 nm))
** 2mPCCzPDBq:PCBBiF:[Ir(tBuppm)$_2$(acac)] (0.7:0.3:0.05 (20 nm)\0.8:0.2:0.05 (20 nm))
*** 2mDBTBPDBq-II:PCBBiF:[Ir(tBuppm)$_2$(acac)] (0.7:0.3:0.05 (20 nm)\0.8:0.2:0.05 (20 nm))

The fabricated light-emitting element 1, light-emitting element 2, and comparative light-emitting element 3 were sealed in a glove box under a nitrogen atmosphere so as not to be exposed to the air (specifically, a sealant was applied to surround the elements, UV treatment was performed, and heat treatment was performed at 80° C. for 1 hour).

Operation Characteristics of Light-Emitting Element 1, Light-Emitting Element 2, and Comparative Light-Emitting Element 3

Operation characteristics of the fabricated light-emitting element 1, light-emitting element 2, and comparative light-emitting element 3 were measured. Note that the measurements were performed at room temperature (in an atmosphere kept at 25° C.). Results are shown in FIG. 23, FIG. 24, FIG. 25, and FIG. 26.

Table 2 shows initial values of main characteristics of the light-emitting element 1, the light-emitting element 2, and the comparative light-emitting element 3 at a luminance of approximately 1000 cd/m$^2$.

TABLE 2

| | Voltage (V) | Current (mA) | Current Density (mA/cm$^2$) | Chromaticity (x, y) | Luminance (cd/m$^2$) | Current Efficiency (cd/A) | Power Efficiency (lm/W) | External Quantum Efficiency (%) |
|---|---|---|---|---|---|---|---|---|
| Light-emitting Element 1 | 2.9 | 0.038 | 1.0 | (0.42, 0.57) | 1100 | 110 | 120 | 29 |
| Light-emitting Element 2 | 2.8 | 0.033 | 0.8 | (0.41, 0.58) | 920 | 110 | 120 | 29 |
| Comparative Light-emitting Element 3 | 2.9 | 0.035 | 0.88 | (0.42, 0.57) | 980 | 110 | 120 | 30 |

Figure 27:
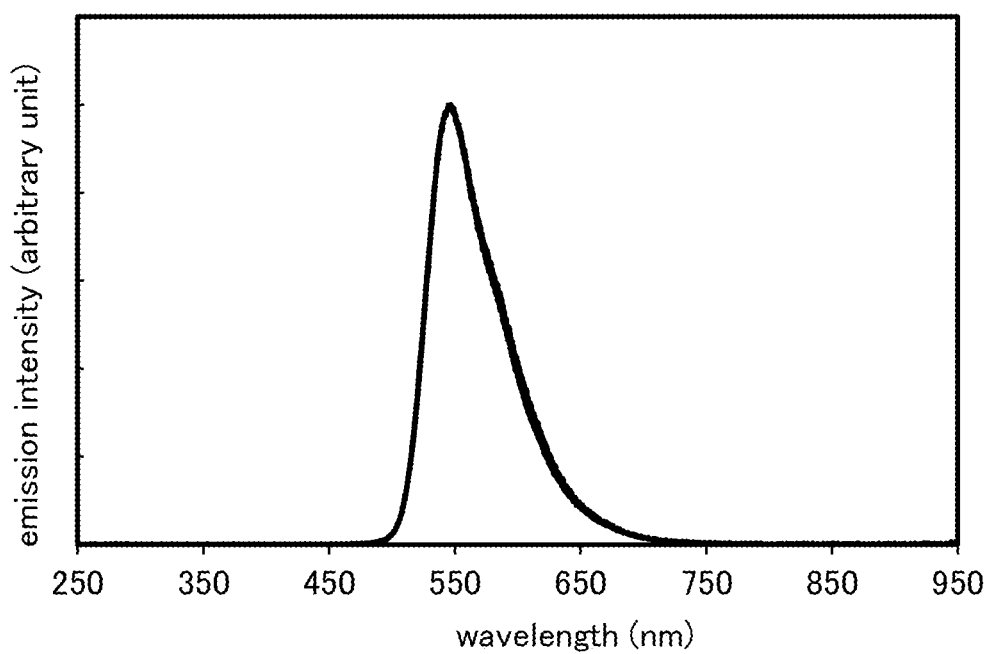
FIG. 27 shows the emission spectra of the light-emitting element 1, the light-emitting element 2, and the comparative light-emitting element 3.

FIG. 27 shows the emission spectra of the light-emitting element 1, the light-emitting element 2, and the comparative light-emitting element 3, through which a current flows at a current density of 2.5 mA/cm². As shown in FIG. 27, the emission spectra of the light-emitting element 1, the light-emitting element 2, and the comparative light-emitting element 3 each have a peak at approximately 546 nm, which is attributed to [Ir(tBuppm)$_2$(acac)].

Figure 28A:
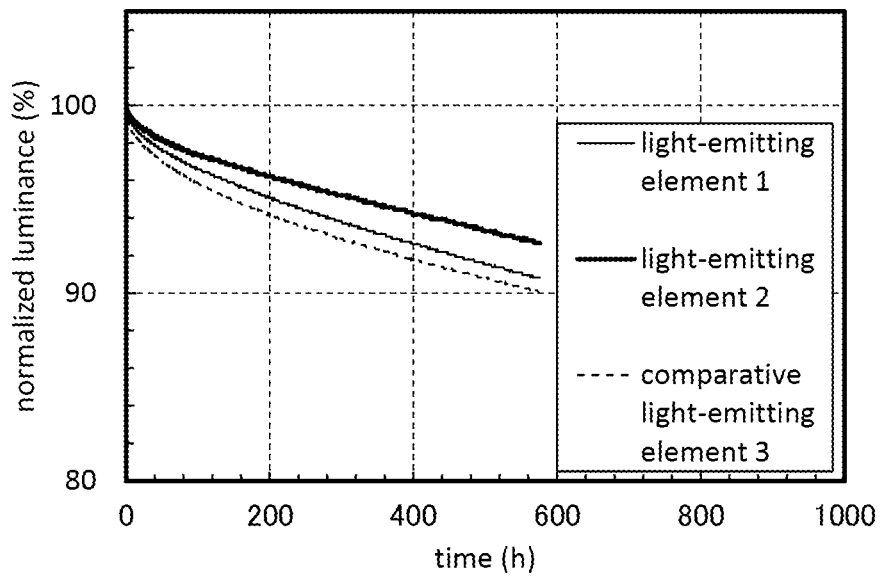
FIGS. 28A and 28B show the reliability of each of the light-emitting element 1, the light-emitting element 2, and the comparative light-emitting element 3.

FIG. 28A shows results of reliability tests on the light-emitting element 1, the light-emitting element 2, and the comparative light-emitting element 3. In FIG. 28A, the vertical axis represents normalized luminance (%) on the assumption that the initial luminance is 100%, and the horizontal axis represents driving time (h) of the elements. Note that in the reliability tests, the light-emitting element 1, the light-emitting element 2, and the comparative light-emitting element 3 were driven under the conditions where the initial luminance was set to be 5000 cd/m² and the current density was constant.

The results show that the light-emitting element 1 fabricated using 2mPCCzPDBq-02 and the light-emitting element 2 fabricated using 2mPCCzPDBq, which are embodiments of the present invention, have a higher reliability and a longer lifetime than the comparative light-emitting element 3 fabricated using 2mDBTBPDBq-II.

Figure 28B:
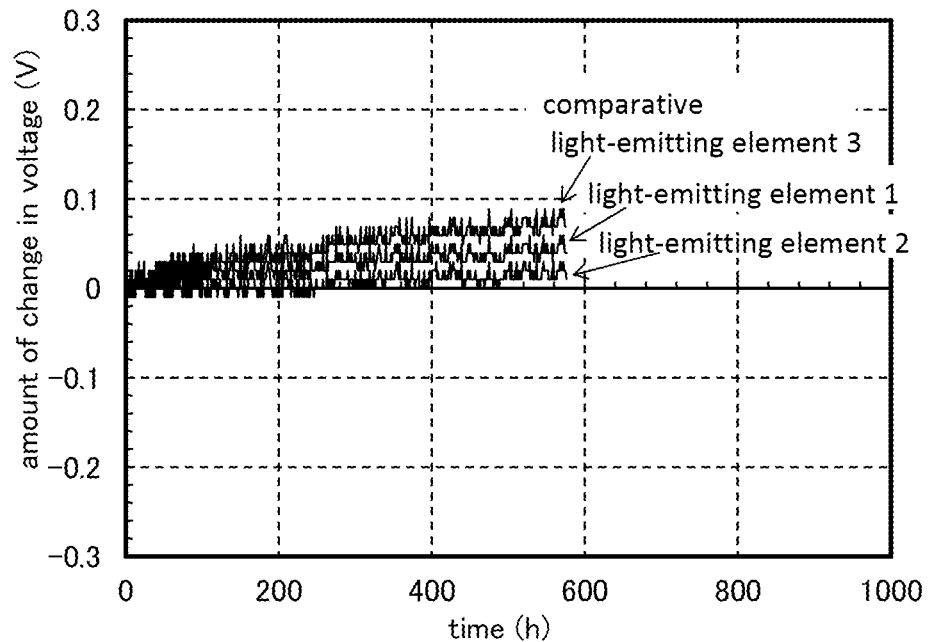
Figure 29:
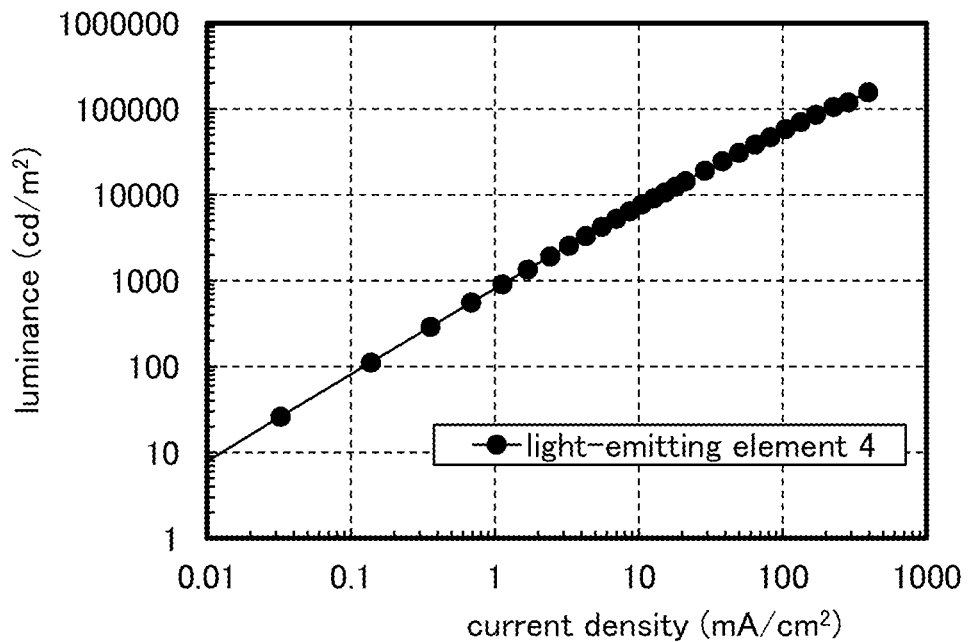
FIG. 29 shows current density-luminance characteristics of a light-emitting element 4.
Figure 30:
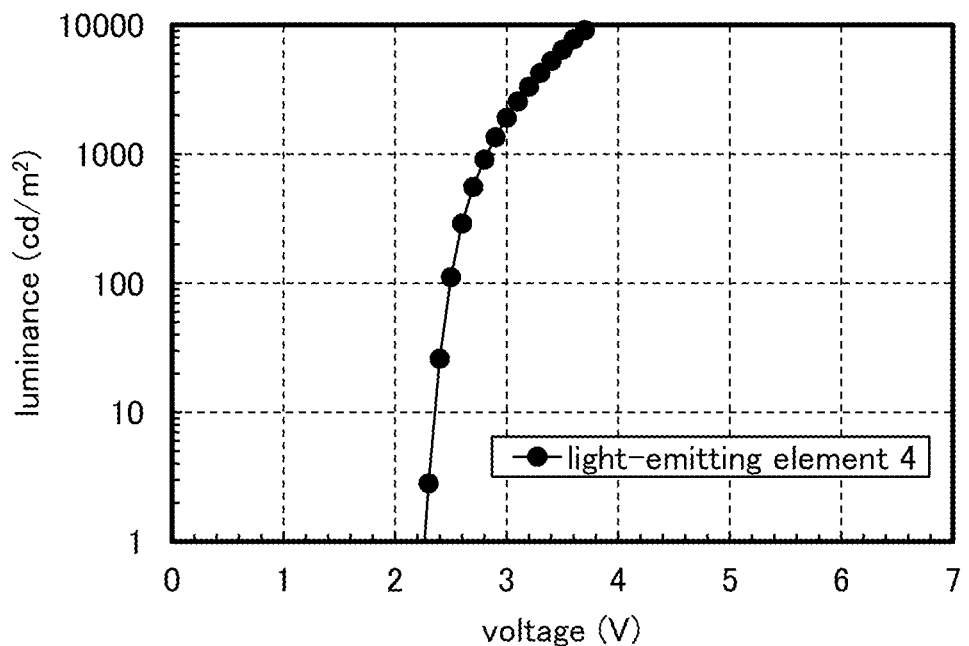
FIG. 30 shows voltage-luminance characteristics of the light-emitting element 4.
Figure 31:
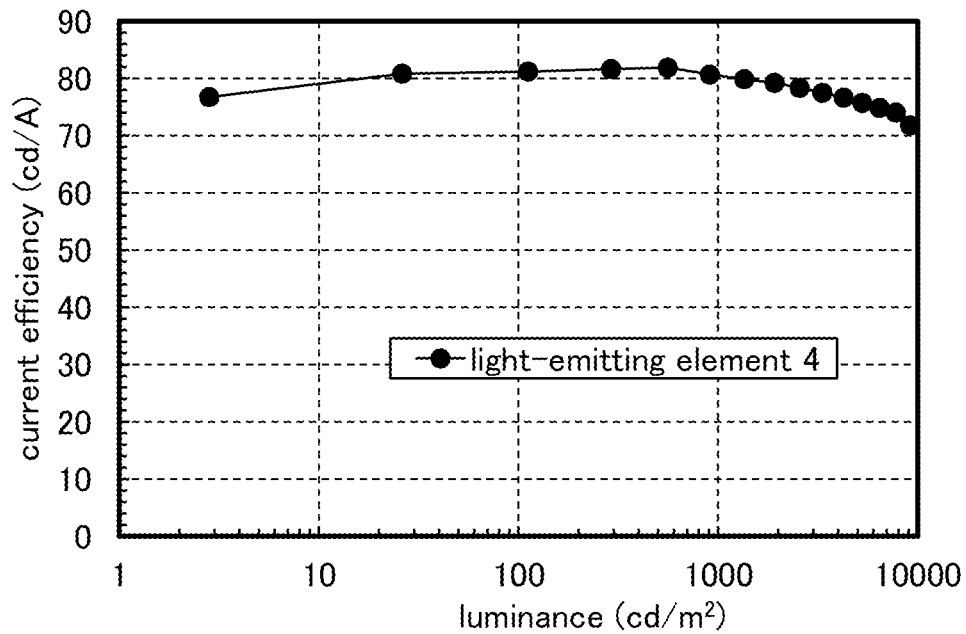
FIG. 31 shows luminance-current efficiency characteristics of the light-emitting element 4.
Figure 32:
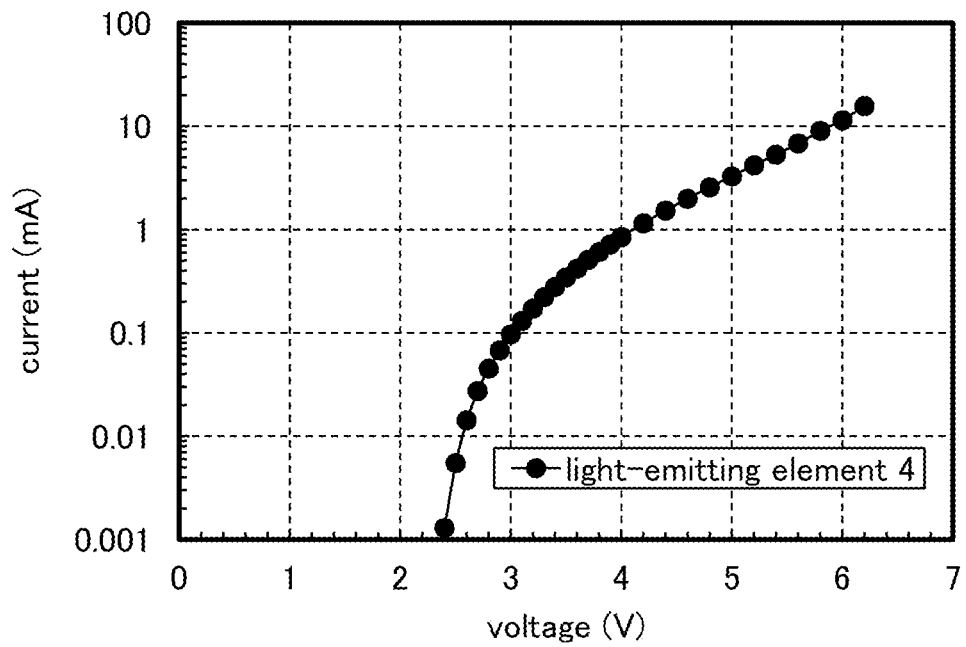
FIG. 32 shows voltage-current characteristics of the light-emitting element 4.

FIG. 28B shows measurement results of the amount of change in voltage at the reliability tests. The vertical axis represents the amount of change in voltage (V), and the horizontal axis represents driving time (h) of the elements. These results show that the amount of increase in voltage in each of the light-emitting element 1 and the light-emitting element 2 which were driven at constant current is smaller than that in the comparative light-emitting element 3. For example, after the light-emitting elements were driven for approximately 500 hours, the amount of increase in voltage in the comparative light-emitting element 3 is approximately 0.08 V, whereas those in the light-emitting elements 1 and 2 are approximately 0.05 V and 0.02 V, respectively. That is, the amount of increase in voltage in the light-emitting element 1 and that in the light-emitting element 2 are approximately as small as ½ and ¼, respectively, of that in the comparative light-emitting element 3, which indicates a significant effect of one embodiment of the present invention.

Note that the combination of PCBBiF and each of 2mPCCzPDBq-02, 2mPCCzPDBq, and 2mDBTBPDBq-II forms an exciplex (because the mixed film containing PCBBiF and any of these dibenzoquinoxaline compounds exhibits yellow-green light emission having a longer wavelength than the film containing only PCBBiF or the film containing only any of these dibenzoquinoxaline compounds). Furthermore, the HOMO levels of 2mPCCzPDBq-02, 2mPCCzPDBq, 2mDBTBPDBq-II, and PCBBiF are −5.69 eV, −5.63 eV, −6.22 eV, and −5.36 eV, respectively. The HOMO levels were obtained through a cyclic voltammetry (CV) measurement.

By using the HOMO levels obtained as described above, $\Delta E_{HOMO}$ in the light-emitting layer of each light-emitting element was calculated. Table 3 shows the results.

TABLE 3

|  | $\Delta E_{HOMO}$ (eV) |
| --- | --- |
| Light-emitting Element 1 | 0.33 |
| Light-emitting Element 2 | 0.27 |
| Comparative Light-emitting Element 3 | 0.86 |

According to the results, it is important that $\Delta E_{HOMO}$ is less than or equal to 0.4 eV, preferably less than or equal to 0.3 eV.

Furthermore, the HOMO level of BPAFLP used for the hole-transport layer is −5.51 eV. Therefore, it is found that the HOMO level of the third organic compound used for the hole-transport layer is lower than the HOMO level of PCBBiF that is the second organic compound and is located between the HOMO level of PCBBiF that is the second organic compound and the HOMO level of the first organic compound (2mPCCzPDBq-02 or 2mPCCzPDBq). This is important because holes are injected not only into the second organic compound but also partly into the first organic compound.

Example 6

In this example, a light-emitting element 4 containing a dibenzo[f,h]quinoxaline derivative which is one embodiment of the present invention was fabricated. The structure of the light-emitting element will be described with reference to FIG. 22 as in Example 5. Chemical formulae of materials used in this example are shown below.

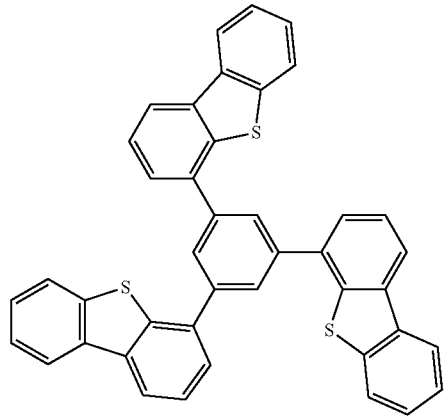

DBT3P-II

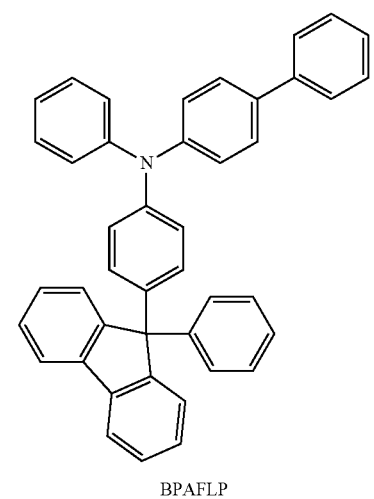

BPAFLP

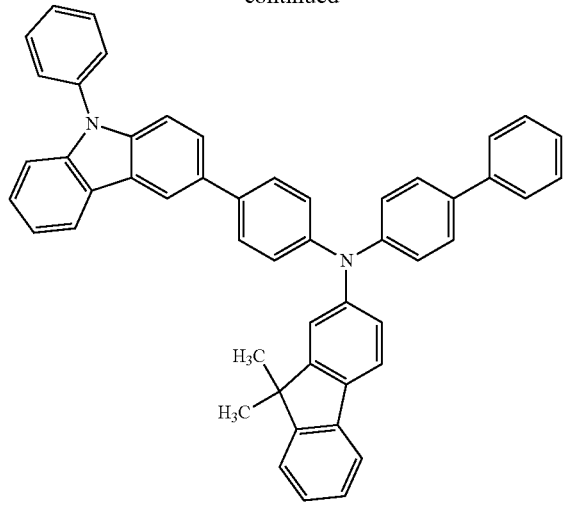

PCBBiF

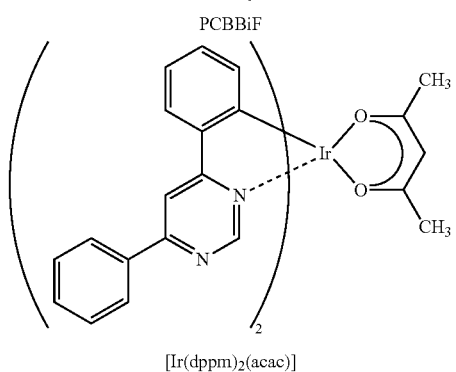

[Ir(dppm)₂(acac)]

(102)

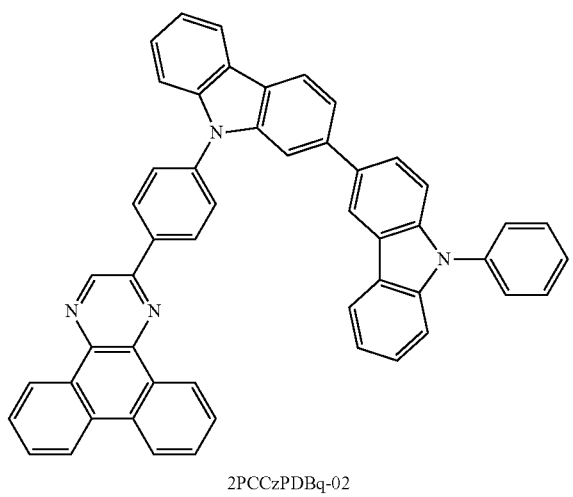

2PCCzPDBq-02

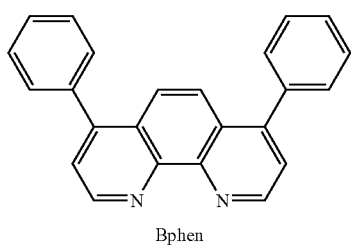

Bphen

Fabrication of Light-Emitting Element 4

First, indium tin oxide containing silicon oxide (ITSO) was deposited over a glass substrate 1100 by a sputtering method, so that a first electrode 1101 functioning as an anode was formed. Note that the thickness of the first electrode 1101 was set to be 110 nm and that the area of the first electrode 1101 was set to be 2 mm×2 mm.

Next, as pretreatment for forming the light-emitting element 4 over the substrate 1100, a surface of the substrate was washed with water, baking was performed at 200° C. for 1 hour, and then UV ozone treatment was performed for 370 seconds.

After that, the substrate 1100 was transferred into a vacuum evaporation apparatus in which the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case will be described where a hole-injection layer 1111, a hole-transport layer 1112, a light-emitting layer 1113, an electron-transport layer 1114, and an electron-injection layer 1115 which are included in an EL layer 1102 were sequentially formed by a vacuum evaporation method.

After reducing the pressure of the vacuum evaporation apparatus to $10^{-4}$ Pa, 1,3,5-tri(dibenzothiophen-4-yl)benzene (abbreviation: DBT3P-II) and molybdenum oxide were deposited by co-evaporation so that the mass ratio of DBT3P-II to molybdenum oxide was 4:2, whereby the hole-injection layer 1111 was formed on the first electrode 1101. The thickness of the hole-injection layer 1111 was set to be 20 nm. Note that co-evaporation is an evaporation method in which a plurality of different substances are concurrently vaporized from their respective evaporation sources.

Then, 4-phenyl-4'-(9-phenylfluoren-9-yl)triphenylamine (abbreviation: BPAFLP) was deposited to a thickness of 20 nm by evaporation, whereby the hole-transport layer 1112 was formed.

Next, the light-emitting layer 1113 was formed on the hole-transport layer 1112. By co-evaporation, 2-{4-[2-(N-phenyl-9H-carbazol-3-yl)-9H-carbazol-9-yl]phenyl}dibenzo[f,h]quinoxaline (abbreviation: 2PCCzPDBq-02, represented by the structural formula (102)), N-(1,1'-biphenyl-4-yl)-N-[4-(9-phenyl-9H-carbazol-3-yl)phenyl]-9,9-dimethyl-9H-fluor en-2-amine (abbreviation: PCBBiF), and (acetylacetonato)bis(4,6-diphenylpyrimidinato)iridium(III) (abbreviation: [Ir(dppm)₂(acac)]) were deposited to a thickness of 20 nm, so that the mass ratio of 2PCCzPDBq-02 to PCBBiF and [Ir(dppm)₂(acac)] was 0.7:0.3:0.05. Then, 2PCCzPDBq-02, PCBBiF, and [Ir(dppm)₂(acac)] were deposited to a thickness of 20 nm by co-evaporation, so that the mass ratio of 2PCCzPDBq-02 to PCBBiF and [Ir(dppm)₂(acac)] was 0.8:0.2:0.05. In this manner, the light-emitting layer 1113 having a stacked structure and a thickness of 40 nm was formed.

Then, 2PCCzPDBq-02 was deposited to a thickness of 20 nm on the light-emitting layer 1113 by evaporation, and then bathophenanthroline (abbreviation: Bphen) was deposited to a thickness of 10 nm by evaporation, whereby the electron-transport layer 1114 was formed.

Furthermore, lithium fluoride was deposited to a thickness of 1 nm on the electron-transport layer 1114 by evaporation, whereby the electron-injection layer 1115 was formed.

Finally, aluminum was deposited to a thickness of 200 nm on the electron-injection layer 1115 by evaporation to form the second electrode 1103 serving as a cathode; thus, the light-emitting element 4 was fabricated. Note that in all the above evaporation steps, evaporation was performed by a resistance-heating method.

Table 4 shows the element structure of the light-emitting element 4 that was fabricated as described above.

TABLE 4

|  | First Electrode | Hole-injection Layer | Hole-transport Layer | Light-emitting Layer | Electron-transport Layer | | Electron-injection Layer | Second Electrode |
| --- | --- | --- | --- | --- | --- | --- | --- | --- |
| Light-emitting Element 4 | ITSO (110 nm) | DBT3P-II:MoOx (4:2 20 nm) | BPAFLP (20 nm) | * | 2PCCzPDBq-02 (20 nm) | Bphen (10 nm) | LiF (1 nm) | Al (200 nm) |

* 2PCCzPDBq-02:PCBBiF:[Ir(dppm)$_2$(acac)] (0.7:0.3:0.05 (20 nm)\0.8:0.2:0.05 (20 nm))

The fabricated light-emitting element 4 was sealed in a glove box under a nitrogen atmosphere so as not to be exposed to the air (specifically, a sealant was applied to surround the element, UV treatment was performed, and heat treatment was performed at 80° C. for 1 hour).

Operation Characteristics of Light-Emitting Element 4

Operation characteristics of the fabricated light-emitting element 4 were measured. Note that the measurements were performed at room temperature (in an atmosphere kept at 25° C.). Results are shown in FIG. 29, FIG. 30, FIG. 31, and FIG. 32.

Table 5 shows initial values of main characteristics of the light-emitting element 4 at a luminance of approximately 1000 cd/m$^2$.

TABLE 5

|  | Voltage (V) | Current (mA) | Current Density (mA/cm$^2$) | Chromaticity (x, y) | Luminance (cd/m$^2$) | Current Efficiency (cd/A) | Power Efficiency (lm/W) | External Quantum Efficiency (%) |
| --- | --- | --- | --- | --- | --- | --- | --- | --- |
| Light-emitting Element 4 | 2.8 | 0.045 | 1.1 | (0.56, 0.44) | 910 | 81 | 91 | 30 |

Figure 33:
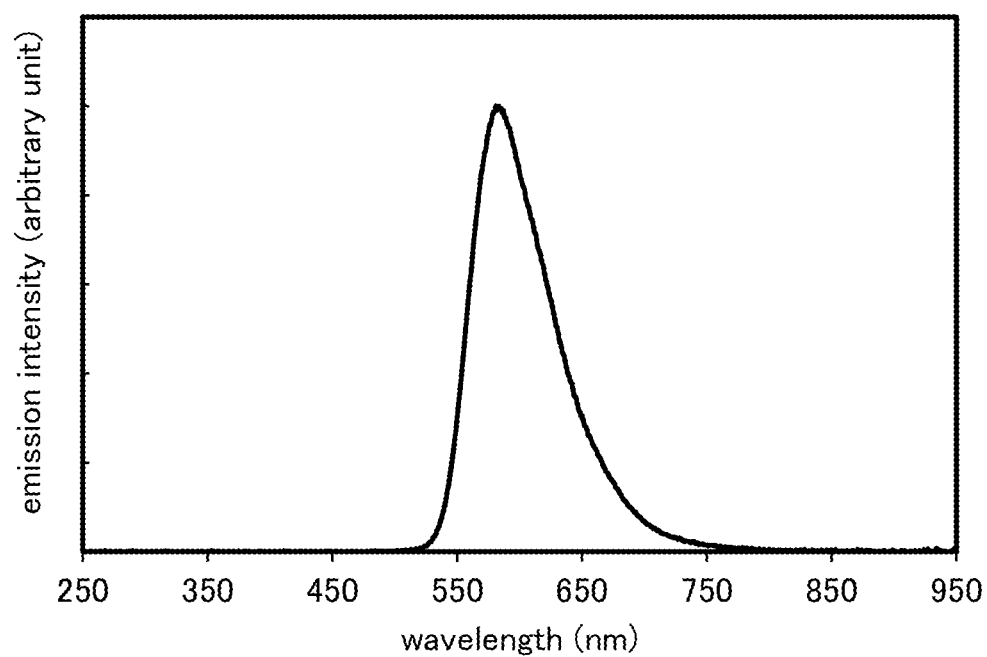
FIG. 33 shows the emission spectrum of the light-emitting element 4.

FIG. 33 shows the emission spectrum of the light-emitting element 4 through which current flows at a current density of 2.5 mA/cm$^2$. As shown in FIG. 33, the emission spectrum of the light-emitting element 4 has a peak at approximately 581 nm, which is attributed to [Ir(dppm)$_2$(acac)].

Figure 34A:
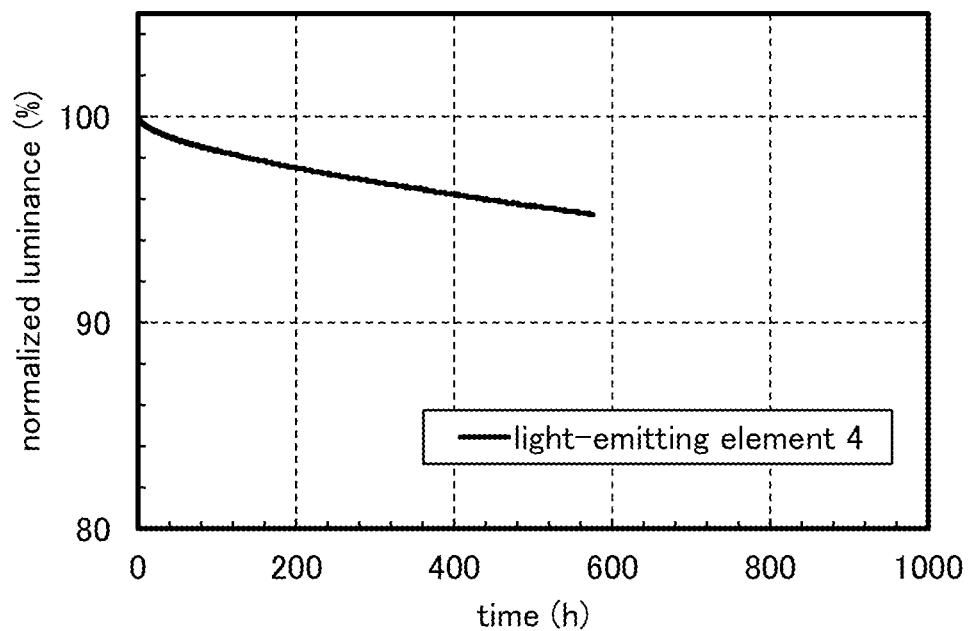
FIGS. 34A and 34B show the reliability of the light-emitting element 4.

FIG. 34A shows results of a reliability test on the light-emitting element 4. In FIG. 34A, the vertical axis represents normalized luminance (%) on the assumption that the initial luminance is 100%, and the horizontal axis represents driving time (h) of the element. Note that in the reliability test, the light-emitting element 4 was driven under the conditions where the initial luminance was set to be 5000 cd/m$^2$ and the current density was constant.

The results show that the light-emitting element 4 fabricated using 2PCCzPDBq-02, which is one embodiment of the present invention, has a high reliability and a long lifetime.

Figure 34B:
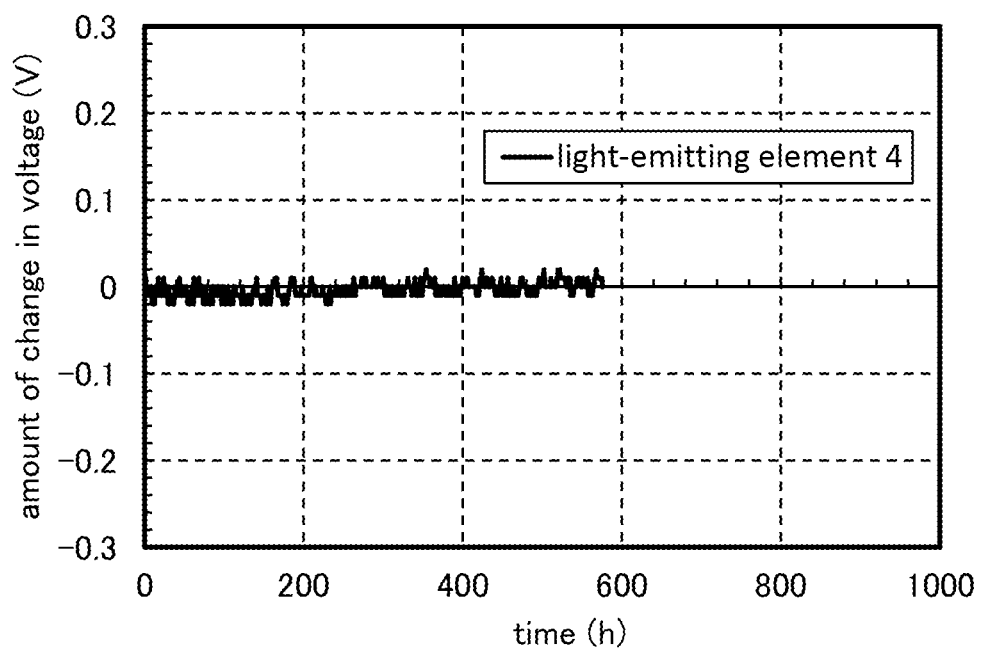

FIG. 34B shows measurement results of the amount of change in voltage at the reliability test. The vertical axis represents the amount of change in voltage (V), and the horizontal axis represents driving time (h) of the element. The results show that the amount of increase in voltage in the light-emitting element 4 which was driven at constant current is small. For example, after the light-emitting element 4 was driven for approximately 500 hours, the amount of increase in voltage is approximately 0.01 V A comparative light-emitting element 9 was fabricated using 2mDBTBPDBq-II instead of 2PCCzPDBq-02 of the light-emitting element 4 and driven under conditions similar to those of the light-emitting element 4. In that case, the amount of increase in voltage was approximately 0.06 V after the comparative light-emitting element 9 was driven for approximately 500 hours. That is, the amount of increase in voltage in the light-emitting element 4 is approximately as small as ⅙ of that in the comparative light-emitting element 9, which indicates a significant effect of one embodiment of the present invention.

Note that the combination of 2PCCzPDBq-02 and PCBBiF forms an exciplex (because the mixed film containing this dibenzoquinoxaline compound and PCBBiF exhibits green light emission having a longer wavelength than the film containing only this dibenzoquinoxaline compound or the film containing only PCBBiF). Furthermore, since the HOMO level of 2PCCzPDBq-02 is −5.68 eV, $\Delta E_{HOMO}$ in the light-emitting layer of the light-emitting element 4 is 0.32 eV. Accordingly, it is important that $\Delta E_{HOMO}$ is less than or equal to 0.4 eV.

Furthermore, the HOMO level of BPAFLP used for the hole-transport layer is −5.51 eV Therefore, it is found that the HOMO level of the third organic compound used for the hole-transport layer is lower than the HOMO level of PCBBiF that is the second organic compound and is located between the HOMO level of PCBBiF that is the second organic compound and the HOMO level of the first organic compound (2PCCzPDBq-02). This is important because holes are injected not only into the second organic compound but also partly into the first organic compound.

Example 7

Synthesis Example 5

In this example, as a synthesis method of one embodiment of the present invention, a synthesis method of 2-{3'-[3-(N-phenyl-9H-carbazol-3-yl)-9H-carbazol-9-yl]biphenyl-3-yl}dibenzo[f,h]quin oxaline (abbreviation: 2mPCCzBPDBq, represented by the structural formula (122)) will be described. The structure of 2mPCCzBPDBq is shown below.

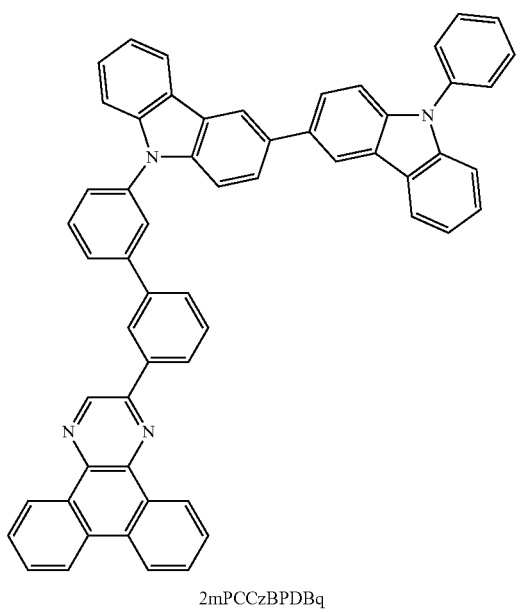

(122)

2mPCCzBPDBq

Synthesis of 2-{3'-[3-(N-phenyl-9H-carbazol-3-yl)-9H-carbazol-9-yl]biphenyl-3-yl}dibenzo[f,h]quin oxaline (abbreviation: 2mPCCzBPDBq)

First, 2.0 g (4.3 mmol) of 2-(3'-bromobiphenyl-3-yl)dibenzo[f,h]quinoxaline, 1.8 g (4.3 mmol) of 3-(9-phenyl-9H-carbazol-3-yl)-9H-carbazole, and 0.83 g (8.6 mmol) of sodium-tert-butoxide were put in a 100-mL three-neck flask and mixed, and the air in the flask was replaced with nitrogen. To this mixture was added 22 mL of mesitylene, and the resulting mixture was degassed by being stirred while the pressure in the flask was reduced.

Next, 25 mg (0.040 mmol) of bis(dibenzylideneacetone)palladium(0) (abbreviation: Pd(dba)$_2$) and 35 mg (0.09 mmol) of 2-dicyclohexylphosphino-2',6'-dimethoxybiphenyl (abbreviation: S-Phos) were added to this mixture. This mixture was stirred at 150° C. for 23 hours under a nitrogen stream. After a predetermined time elapsed, water and toluene were added to this mixture, and an aqueous layer of the obtained filtrate was subjected to extraction with toluene. The obtained extract solution and an organic layer were combined, washed with an aqueous solution of sodium hydrogen carbonate and saturated brine, and dried with magnesium sulfate. The obtained mixture was gravity-filtered, and the filtrate was concentrated to give an oily substance. The oily substance was dissolved in toluene, and this solution was suction-filtered through a stack of Celite and alumina. The obtained filtrate was concentrated to give a brown oily substance. This oily substance was purified by high performance liquid chromatography. Column chromatography was performed using chloroform as a developing solvent (the pressure: 4.5 MPa, the flow rate: 100 mL/min, the holding time: 45 minutes, and the injection amount: 0.9 g/30 mL). The obtained fraction was concentrated and recrystallized with hexane to give 0.66 g of a yellow powder, which was the target substance, in a yield of 18%.

By a train sublimation method, 0.66 g of the obtained yellow powdered solid, which was the target substance, was purified. The sublimation purification was carried out at 385° C. under a pressure of 2.6 Pa with a flow rate of an argon gas at 5 mL/min. After the sublimation purification, 0.5 g of a yellow glassy solid of 2mPCCzBPDBq was obtained at a collection rate of 83%. The synthesis scheme of this step is shown in the following scheme (e-1).

(e-1)

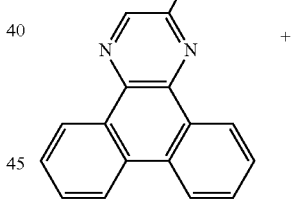

+

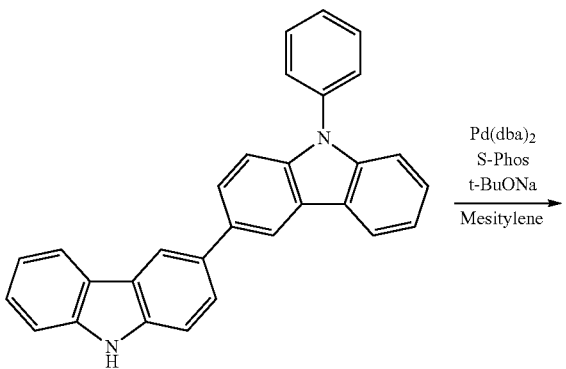

Pd(dba)$_2$
S-Phos
t-BuONa
⟶
Mesitylene

-continued

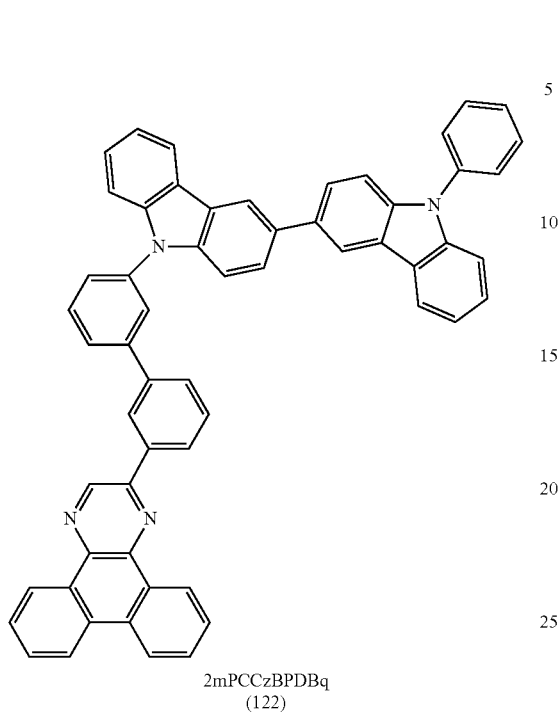

2mPCCzBPDBq
(122)

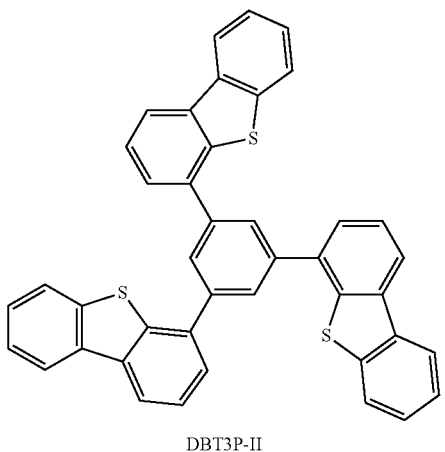

DBT3P-II

Figure 35A:
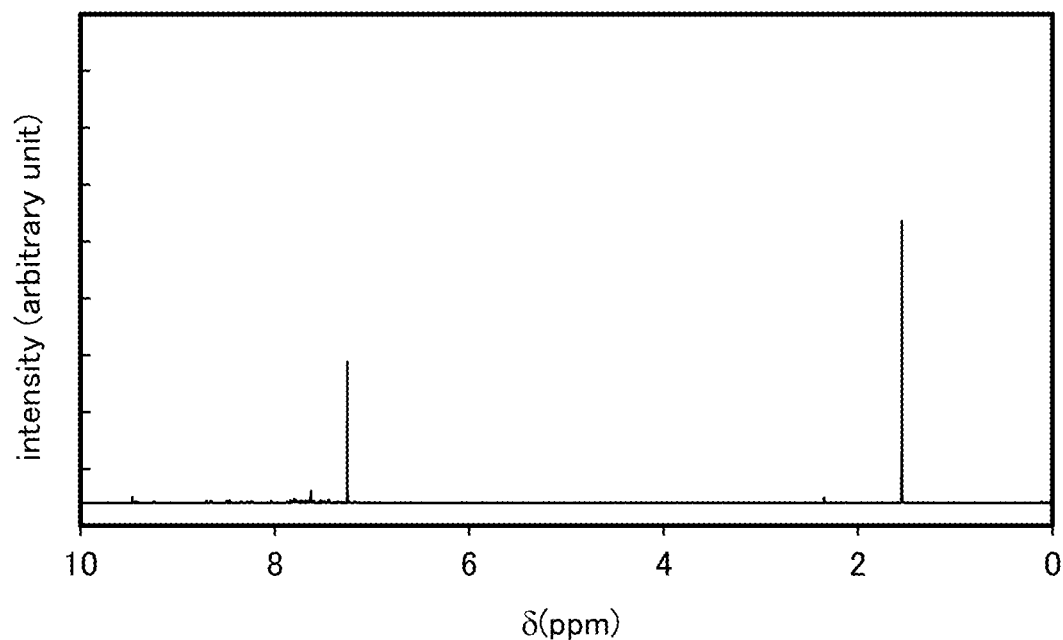
FIGS. 35A and 35B are $^1$H-NMR charts of a dibenzo[f,h]quinoxaline derivative represented by the structural formula (122).
Figure 35B:
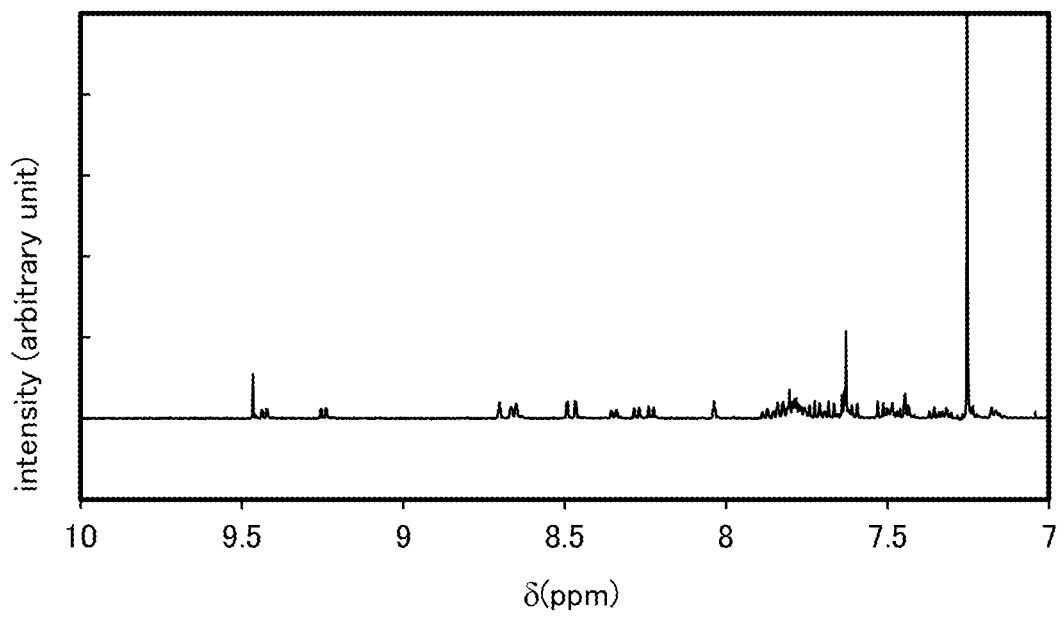

Analysis results by nuclear magnetic resonance spectroscopy ($^1$H-NMR) of the yellow powdered solid obtained in the above step will be described below. $^1$H-NMR charts are shown in FIGS. 35A and 35B. FIG. 35B is a chart in which the range from 7.0 (ppm) to 10 (ppm) on the horizontal axis (δ) in FIG. 35A is enlarged. These results show that 2-{3'-[3-(N-phenyl-9H-carbazol-3-yl)-9H-carbazol-9-yl]biphenyl-3-yl}dibenzo[f,h]quin oxaline (abbreviation: 2mPCCzBPDBq, represented by the structural formula (122)) was obtained in the above step.

$^1$H-NMR (CDCl$_3$, 500 MHz): δ (ppm)=7.30-7.37 (m, 2H), 7.41-7.53 (m, 5H), 7.59-7.89 (m, 18H), 8.04 (dd, J=1.7 Hz, 1H), 8.23 (d, J=7.5 Hz, 1H), 8.28 (d, 8.0 Hz, 1H), 8.35 (d, J=8.0 Hz, 1H), 8.48 (dd, J=11.4 Hz, J=1.7 Hz, 2H), 8.66 (d, J=8.1 Hz, 1H), 8.70 (s, 1H), 9.25 (dd, J=6.3 Hz, J=1.1 Hz, 1H), 9.43 (dd, J=7.5 Hz, J=1.7 Hz, 1H), 9.47 (s, 1H).

Example 8

In this example, a light-emitting element 5 containing the dibenzo[f,h]quinoxaline derivative, 2mPCCzPDBq, which is represented by the structural formula (101) and is one embodiment of the present invention, a comparative light-emitting element 6 containing a comparative material, 2mDBTPDBq-II, and a comparative light-emitting element 7 containing a comparative material, 2-[3-(9H-carbazol-9-yl)phenyl]dibenzo[f,h]quinoxaline (abbreviation: 2mCzPDBq), were fabricated. A fabrication method of each light-emitting element is basically the same as that in Example 5 and thus omitted. Chemical formulae of materials used in this example are shown below.

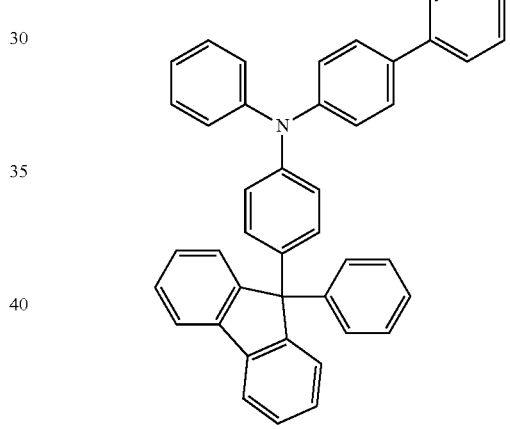

BPAFLP

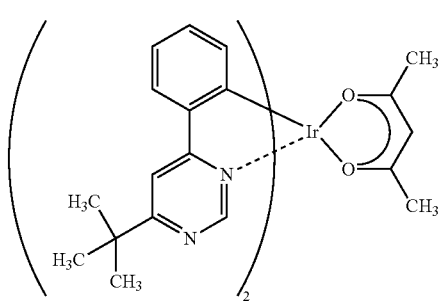

[Ir(tBuppm)$_2$(acac)]

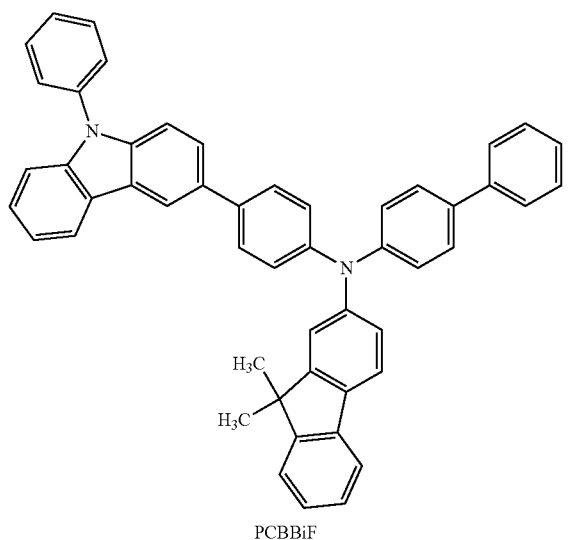
PCBBiF
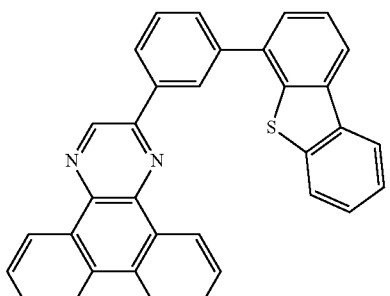
2mDBTPDBq-II
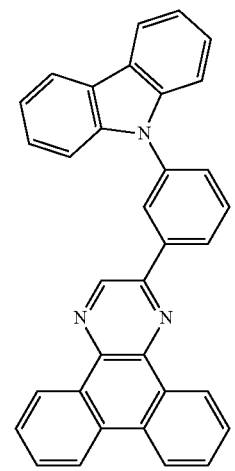
2mCzPDBq
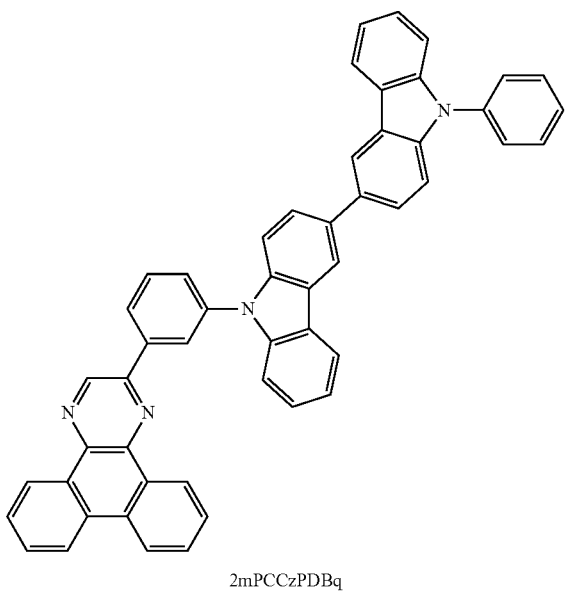
2mPCCzPDBq
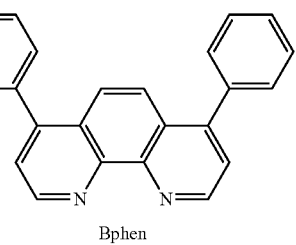
Bphen
Fabrication of Light-Emitting Element 5, Comparative Light-Emitting Element 6, and Comparative Light-Emitting Element 7
Table 6 shows the element structures of the light-emitting element 5, the comparative light-emitting element 6, and the comparative light-emitting element 7 fabricated in this example.

TABLE 6

| | First Electrode | Hole-injection Layer | Hole-transport Layer | Light-emitting Layer | Electron-transport Layer | Electron-injection Layer | Second Electrode |
|---|---|---|---|---|---|---|---|
| Light-emitting Element 5 | ITO (110 nm) | DBT3P-II:MoOx (4:2 20 nm) | BPAFLP (20 nm) | * | 2mPCCzPDBq (20 nm) | Bphen (10 nm) | LiF (1 nm) | Al (200 nm) |
| Comparative Light-emitting Element 6 | ITO (110 nm) | DBT3P-II:MoOx (4:2 20 nm) | BPAFLP (20 nm) | ** | 2mDBTPDBq-II (20 nm) | Bphen (10 nm) | LiF (1 nm) | Al (200 nm) |
| Comparative Light-emitting Element 7 | ITO (110 nm) | DBT3P-II:MoOx (4:2 20 nm) | BPAFLP (20 nm) | *** | 2mCzPDBq (20 nm) | Bphen (10 nm) | LiF (1 nm) | Al (200 nm) |

* 2mPCCzPDBq:PCBBiF:[Ir(tBuppm)$_2$(acac)] (0.7:0.3:0.05 (20 nm)\0.8:0.2:0.05 (20 nm))
** 2mDBTPDBq-II:PCBBiF:[Ir(tBuppm)$_2$(acac)] (0.7:0.3:0.05 (20 nm)\0.8:0.2:0.05 (20 nm))
*** 2mCzPDBq:PCBBiF:[Ir(tBuppm)$_2$(acac)] (0.7:0.3:0.05 (20 nm)\0.8:0.2:0.05 (20 nm))

The fabricated light-emitting element 5, comparative light-emitting element 6, and comparative light-emitting element 7 were sealed in a glove box under a nitrogen atmosphere so as not to be exposed to the air (specifically, a sealant was applied to surround the elements, UV treatment was performed, and heat treatment was performed at 80° C. for 1 hour).

Operation Characteristics of Light-Emitting Element 5, Comparative Light-Emitting Element 6, and Comparative Light-Emitting Element 7

Operation characteristics of the fabricated light-emitting element 5, comparative light-emitting element 6, and comparative light-emitting element 7 were measured. Note that the measurements were performed at room temperature (in an atmosphere kept at 25° C.).

Figure 36:
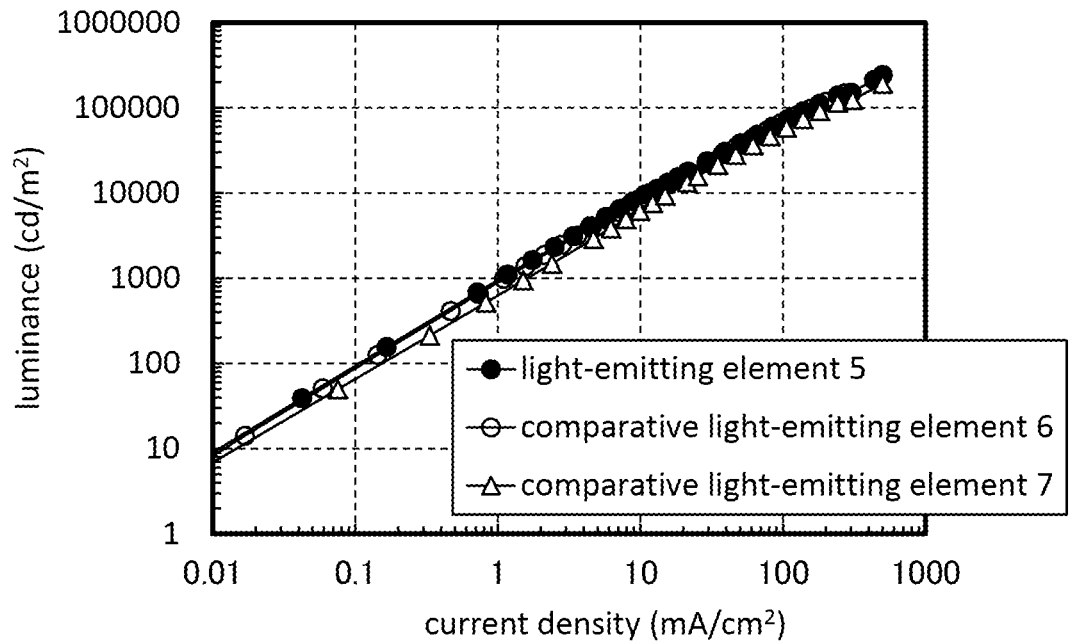
FIG. 36 shows current density-luminance characteristics of a light-emitting element 5, a comparative light-emitting element 6, and a comparative light-emitting element 7.
Figure 37:
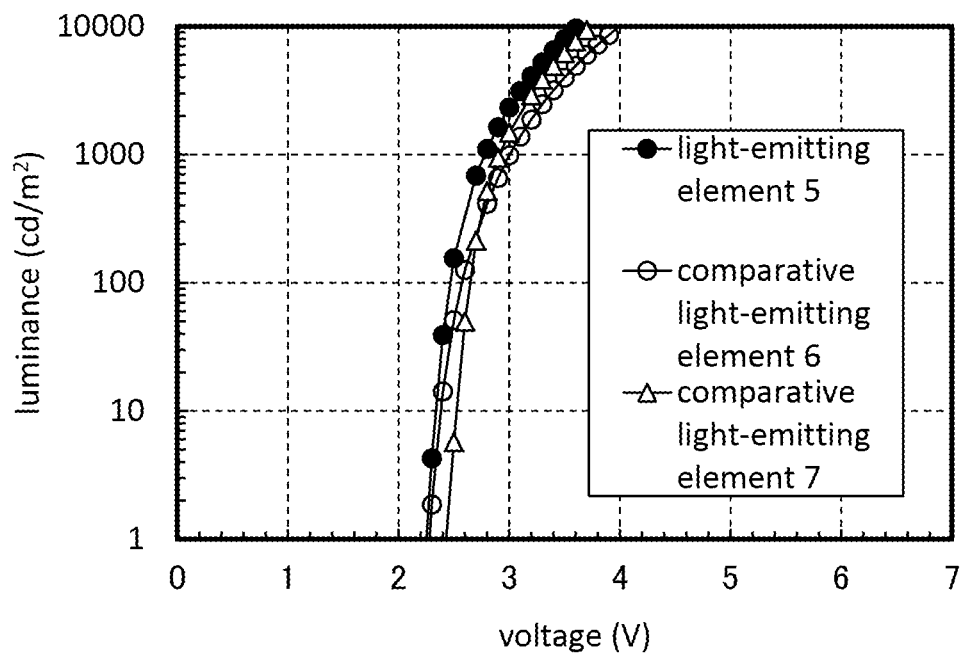
FIG. 37 shows voltage-luminance characteristics of the light-emitting element 5, the comparative light-emitting element 6, and the comparative light-emitting element 7.
Figure 38:
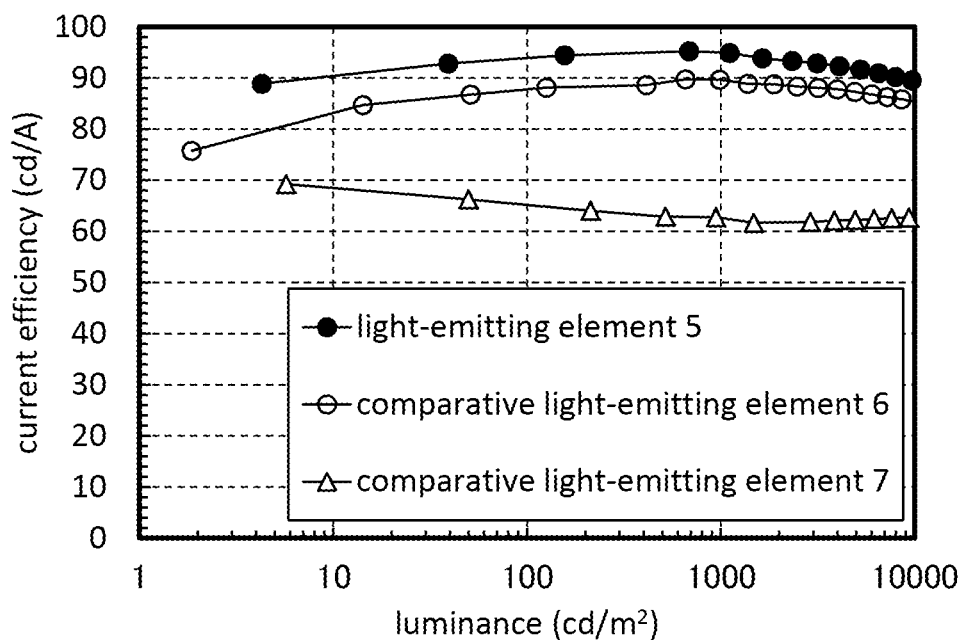
FIG. 38 shows luminance-current efficiency characteristics of the light-emitting element 5, the comparative light-emitting element 6, and the comparative light-emitting element 7.
Figure 39:
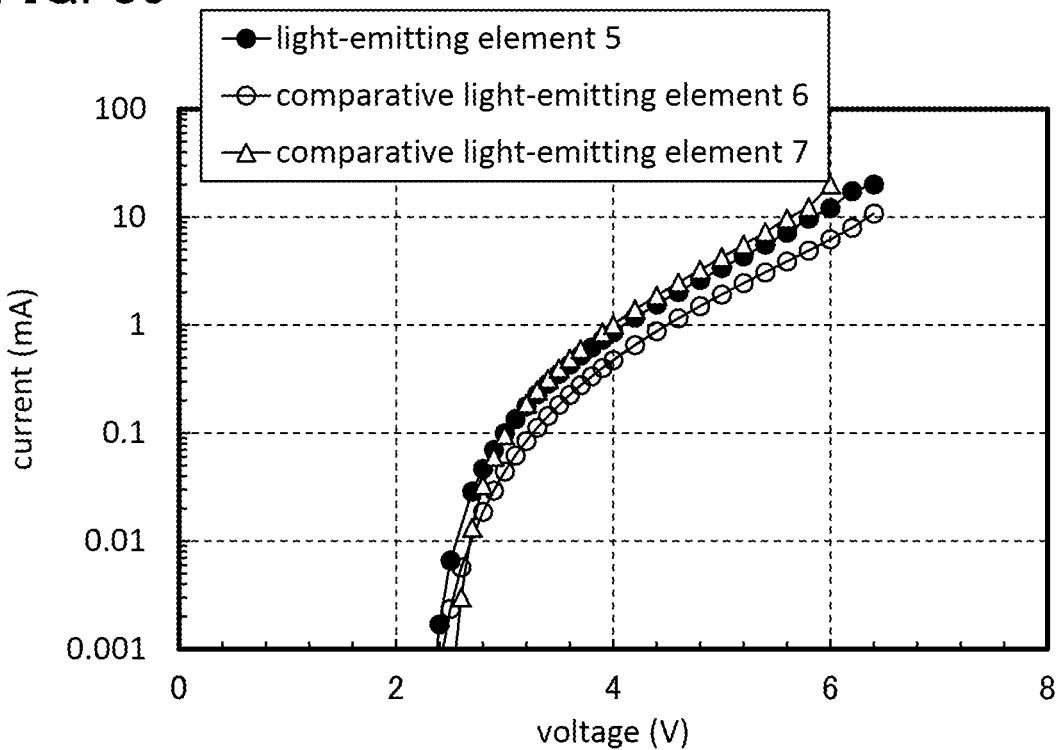
FIG. 39 shows voltage-current characteristics of the light-emitting element 5, the comparative light-emitting element 6, and the comparative light-emitting element 7.

FIG. 36 shows current density-luminance characteristics, FIG. 37 shows voltage-luminance characteristics, FIG. 38 shows luminance-current efficiency characteristics, and FIG. 39 shows voltage-current characteristics of each light-emitting element.

Table 7 shows initial values of main characteristics of the light-emitting element 5, the comparative light-emitting element 6, and the comparative light-emitting element 7 at a luminance of approximately 1000 cd/m$^2$.

Figure 40:
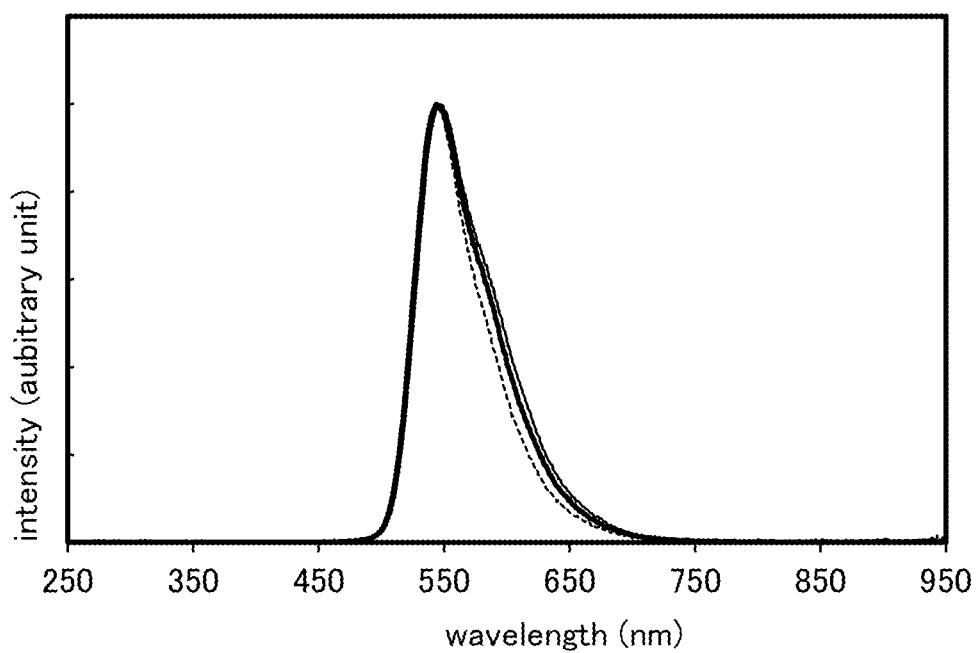
FIG. 40 shows the emission spectra of the light-emitting element 5, the comparative light-emitting element 6, and the comparative light-emitting element 7.

FIG. 40 shows the emission spectra of the light-emitting element 5, the comparative light-emitting element 6, and the comparative light-emitting element 7, through which a current flows at a current density of 2.5 mA/cm$^2$. As shown in FIG. 40, the emission spectra of the light-emitting element 5, the comparative light-emitting element 6, and the comparative light-emitting element 7 each have a peak at approximately 544 nm, which is attributed to [Ir(tBuppm)$_2$ (acac)].

Figure 41A:
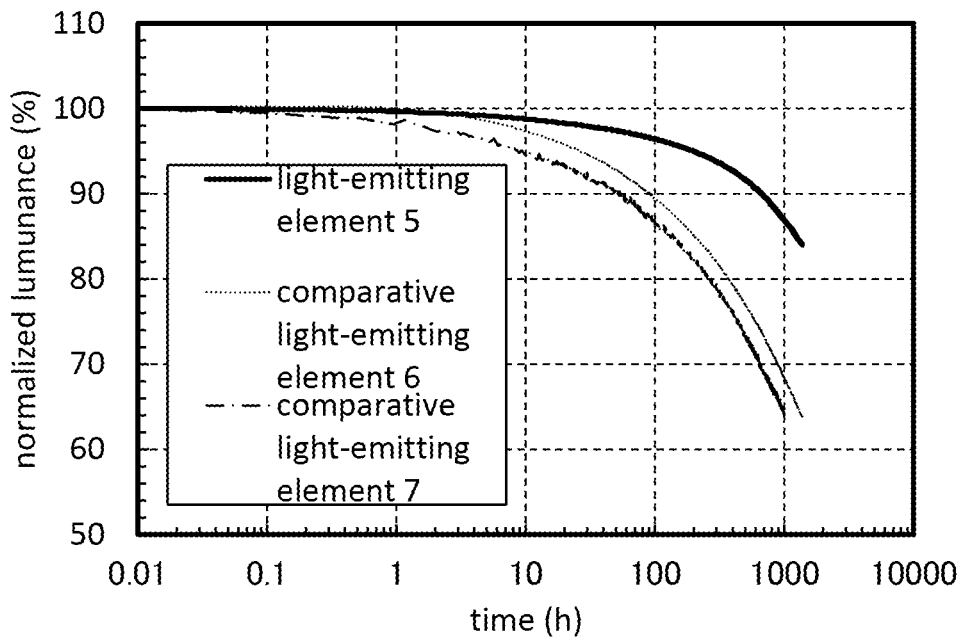
FIGS. 41A and 41B show the reliability of each of the light-emitting element 5, the comparative light-emitting element 6, and the comparative light-emitting element 7.

FIG. 41A shows results of reliability tests on the light-emitting element 5, the comparative light-emitting element 6, and the comparative light-emitting element 7. In FIG. 41A, the vertical axis represents normalized luminance (%) on the assumption that the initial luminance is 100%, and the horizontal axis represents driving time (h) of the elements. Note that in the reliability tests, the light-emitting element 5, the comparative light-emitting element 6, and the comparative light-emitting element 7 were driven under the conditions where the initial luminance was set to be 5000 cd/m$^2$ and the current density was constant.

The results show that the light-emitting element 5 fabricated using 2mPCCzPDBq, which is one embodiment of the present invention, has a higher reliability and a longer lifetime than the comparative light-emitting element 6 fabricated using 2mDBTPDBq-II and the comparative light-emitting element 7 fabricated using 2mCzPDBq.

Figure 41B:
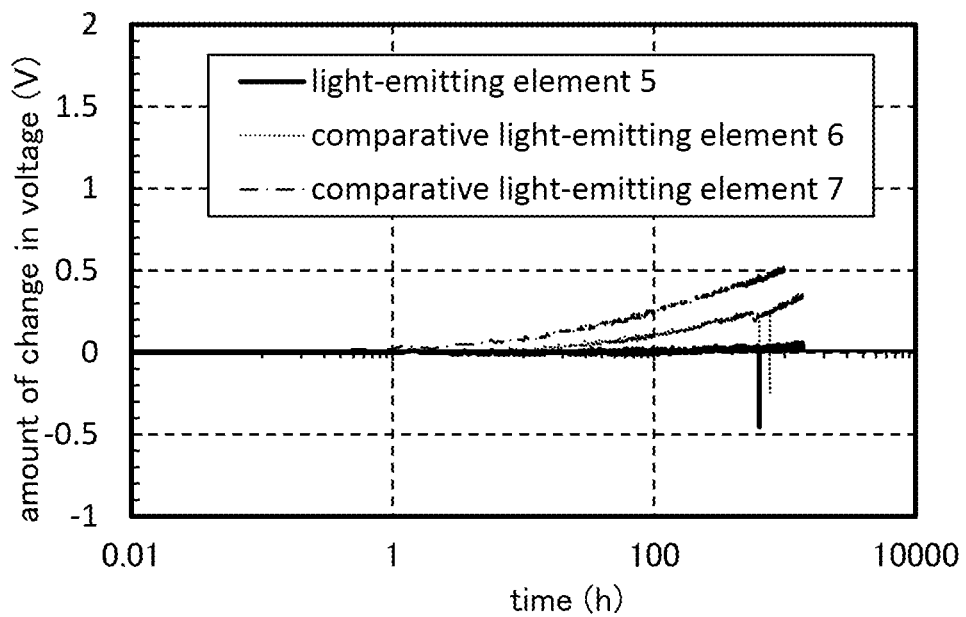

FIG. 41B shows measurement results of the amount of change in voltage at the reliability tests. The vertical axis represents the amount of change in voltage (V), and the horizontal axis represents the driving time (h) of the ele-

TABLE 7

| | Voltage (V) | Current (mA) | Current Density (mA/cm$^2$) | Chromaticity (x, y) | Luminance (cd/m$^2$) | Current Efficiency (cd/A) | Power Efficiency (lm/W) | External Quantum Efficiency (%) |
|---|---|---|---|---|---|---|---|---|
| Light-emitting Element 5 | 2.8 | 0.047 | 1.2 | (0.42, 0.57) | 1100 | 95 | 110 | 25 |
| Comparative Light-emitting Element 6 | 3.0 | 0.044 | 1.1 | (0.43, 0.56) | 990 | 90 | 94 | 24 |
| Comparative Light-emitting Element 7 | 2.9 | 0.060 | 1.5 | (0.41, 0.58) | 940 | 63 | 68 | 16 | ments. These results show that the amount of increase in voltage in the light-emitting element 5 which was driven at constant current is smaller than those in the comparative light-emitting elements 6 and 7. For example, after the light-emitting elements were driven for approximately 1000 hours, the amount of increase in voltage in the comparative light-emitting element 6 is approximately 0.31 V and that in the comparative light-emitting element 7 is approximately 0.50 V, whereas that in the light-emitting element 5 is approximately 0.04 V That is, the amount of increase in voltage in the light-emitting element 5 is much smaller than those in the comparative light-emitting elements 6 and 7, which indicates a significant effect of one embodiment of the present invention.

Note that the combination of PCBBiF and each of 2mPCCzPDBq, 2mDBTPDBq-II, and 2mCzPDBq forms an exciplex (because the mixed film containing PCBBiF and any of these dibenzoquinoxaline compounds exhibits yellow-green light emission having a longer wavelength than the film containing only PCBBiF or the film containing only any of these dibenzoquinoxaline compounds). Furthermore, the HOMO levels of 2mPCCzPDBq, 2mDBTPDBq-II, 2mCzPDBq, and PCBBiF are −5.63 eV, −6.22 eV, −5.91 eV, and −5.36 eV, respectively. The HOMO levels were obtained through a cyclic voltammetry (CV) measurement.

By using the HOMO levels obtained as described above, $\Delta E_{HOMO}$ in the light-emitting layer of each light-emitting element was calculated. Table 8 shows the results.

TABLE 8

| | $\Delta E_{HOMO}$ (eV) |
|---|---|
| Light-emitting Element 5 | 0.27 |
| Comparative Light-emitting Element 6 | 0.86 |
| Comparative Light-emitting Element 7 | 0.55 |

According to the results, it is important that $\Delta E_{HOMO}$ is less than or equal to 0.4 eV, preferably less than or equal to 0.3 eV.

Furthermore, the HOMO level of BPAFLP used for the hole-transport layer is −5.51 eV Therefore, it is found that the HOMO level of the third organic compound used for the hole-transport layer is lower than the HOMO level of PCBBiF that is the second organic compound and is located between the HOMO level of PCBBiF that is the second organic compound and the HOMO level of the first organic compound (2mPCCzPDBq). This is important because holes are injected not only into the second organic compound but also partly into the first organic compound.

Example 9

In this example, a light-emitting element 8 containing the dibenzo[f,h]quinoxaline derivative, 2mPCCzBPDBq, which is one embodiment of the present invention, was fabricated. A fabrication method of the light-emitting element 8 is basically the same as that in Example 5 and thus omitted. Chemical formulae of materials used in this example are shown below.

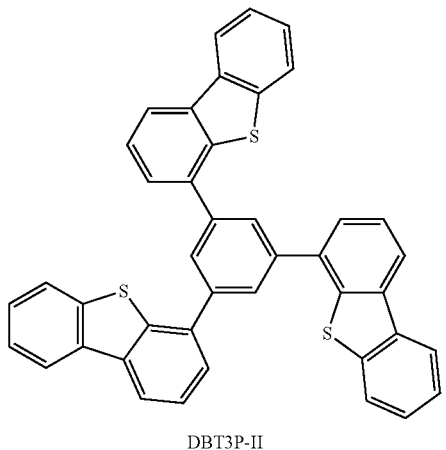

DBT3P-II

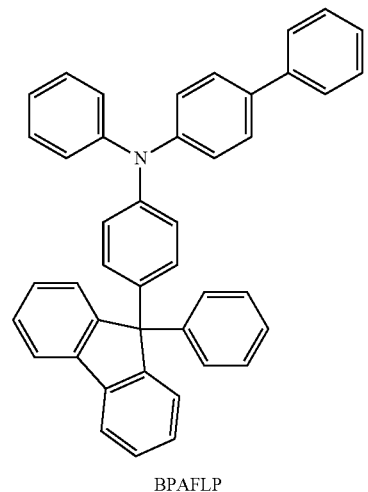

BPAFLP

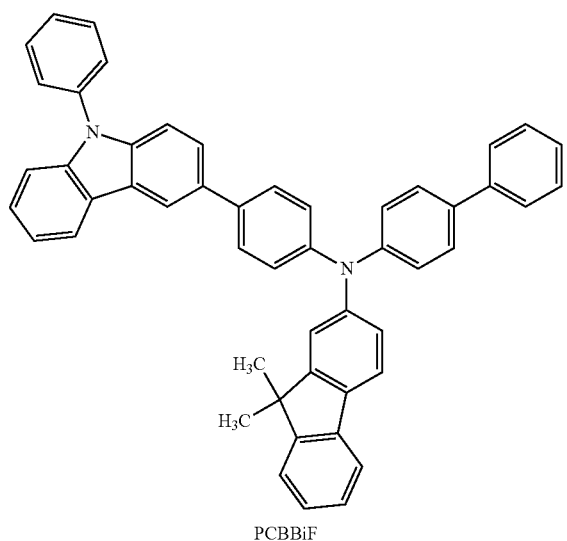

PCBBiF

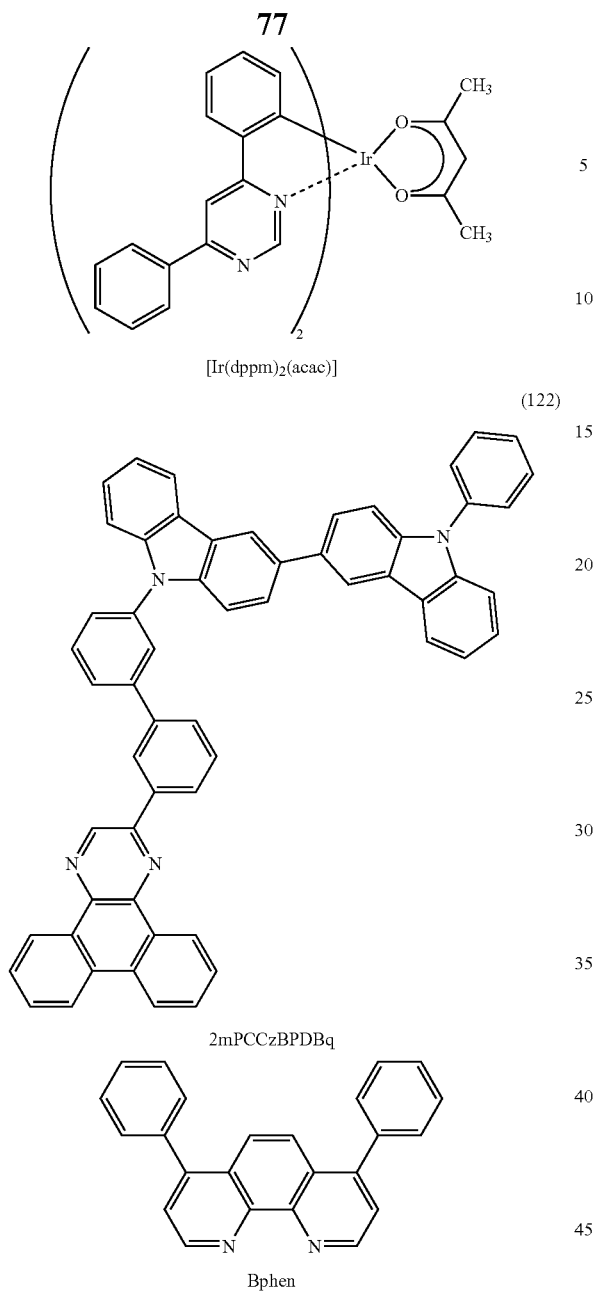

[Ir(dppm)₂(acac)]

(122)

2mPCCzBPDBq

Bphen

Fabrication of Light-Emitting Element 8

Table 9 shows the element structure of the light-emitting element 8 fabricated in this example.

TABLE 9

|  | First Electrode | Hole-injection Layer | Hole-transport Layer | Light-emitting Layer | Elecron-transport Layer | Electron-injection Layer | Second Electrode |
|---|---|---|---|---|---|---|---|
| Light-emitting Element 8 | ITO (110 nm) | DBT3P-II:MoOx (4:2 60 nm) | BPAFLP (20 nm) | * | 2mPCCzBPDBq (20 nm) | Bphen (10 nm) | LiF (1 nm) | Al (200 nm) |

* 2mPCCzBPDBq:PCBBiF:[Ir(dppm)₂(acac)] (0.7:0.3:0.05 (20 nm)\0.8:0.2:0.05 (20 nm))

The fabricated light-emitting element 8 was sealed in a glove box under a nitrogen atmosphere so as not to be exposed to the air (specifically, a sealant was applied to surround the element, UV treatment was performed, and heat treatment was performed at 80° C. for 1 hour).

Operation Characteristics of Light-Emitting Element 8

Operation characteristics of the fabricated light-emitting element 8 were measured. Note that the measurements were performed at room temperature (in an atmosphere kept at 25° C.).

Figure 42:
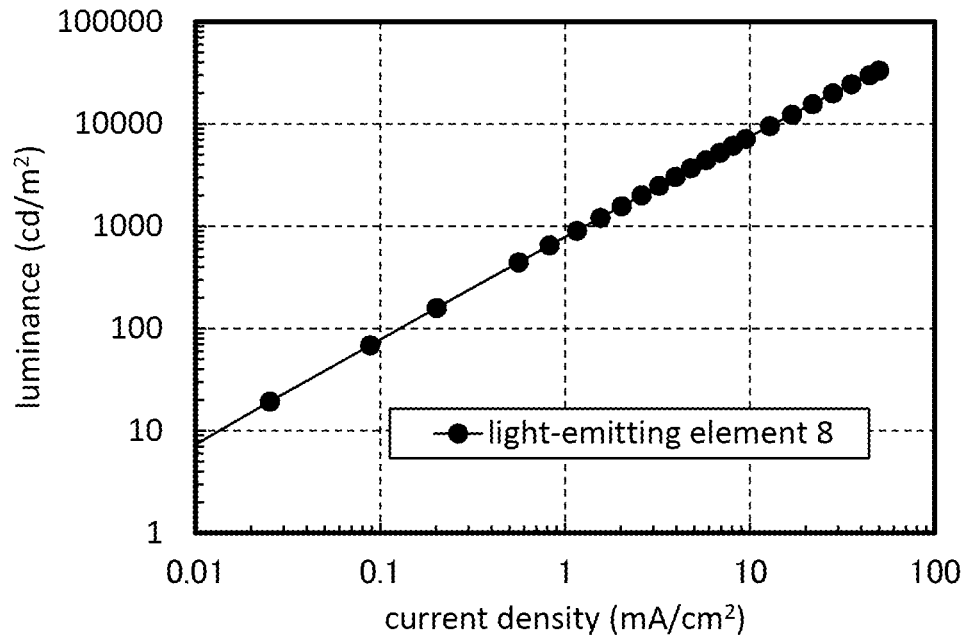
FIG. 42 shows current density-luminance characteristic of a light-emitting element 8.
Figure 43:
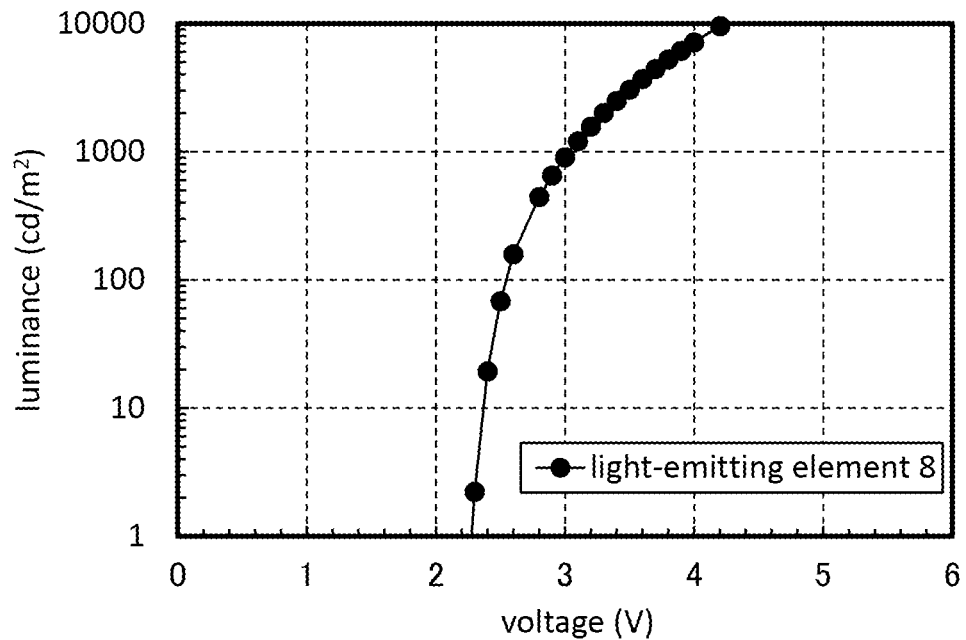
FIG. 43 shows voltage-luminance characteristic of the light-emitting element 8.
Figure 44:
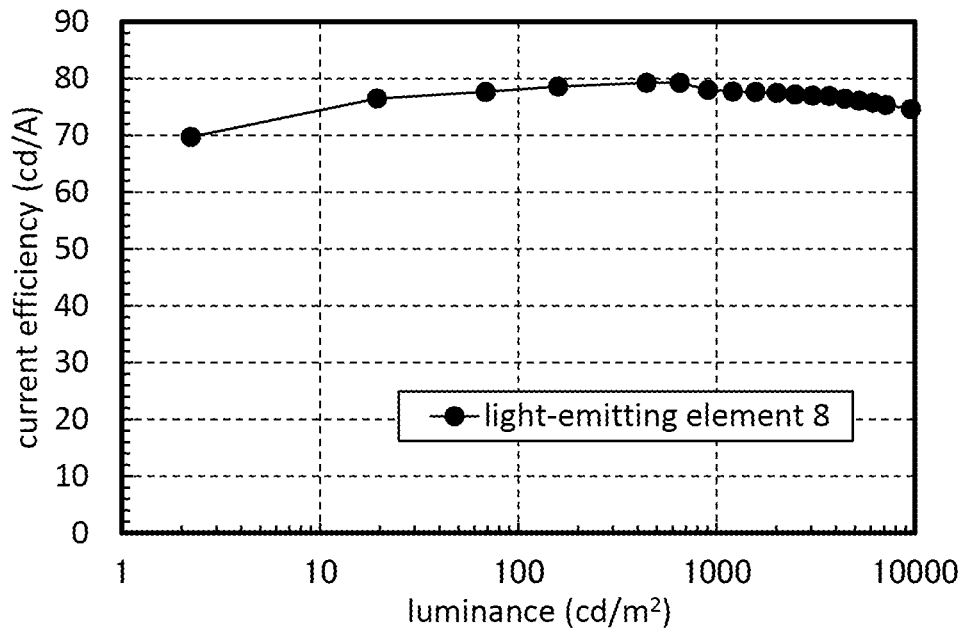
FIG. 44 shows luminance-current efficiency characteristics of the light-emitting element 8.
Figure 45:
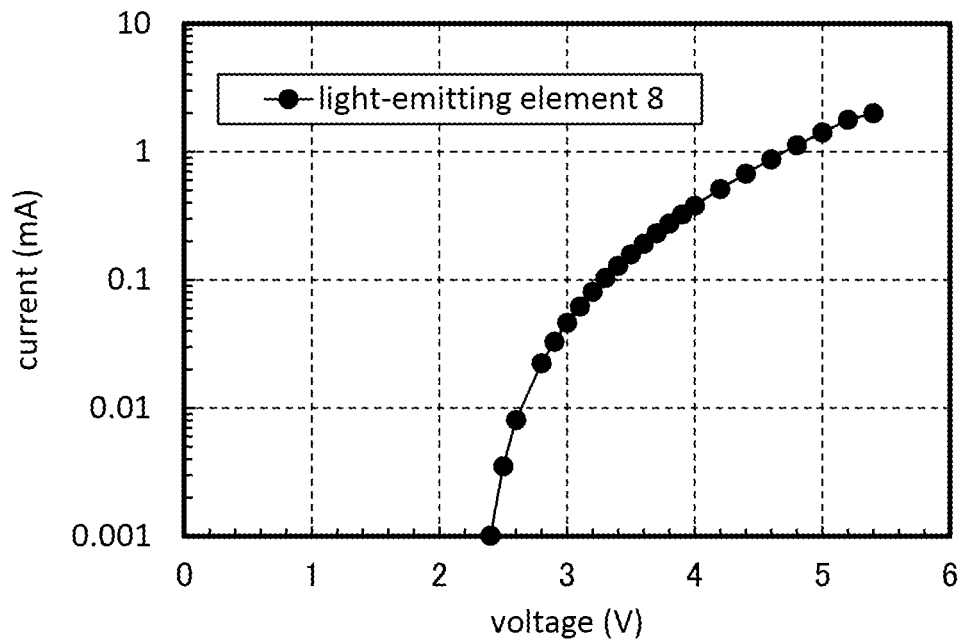
FIG. 45 shows voltage-current characteristics of the light-emitting element 8.

FIG. 42 shows current density-luminance characteristics, FIG. 43 shows voltage-luminance characteristics, FIG. 44 shows luminance-current efficiency characteristics, and FIG. 45 shows voltage-current characteristics of the light-emitting element 8.

Table 10 shows initial values of main characteristics of the light-emitting element 8 at a luminance of approximately 1000 cd/m$^2$.

TABLE 10

| | Voltage (V) | Current (mA) | Current Density (mA/cm$^2$) | Chromaticity (x, y) | Luminance (cd/m$^2$) | Current Efficiency (cd/A) | Power Efficiency (lm/W) | External Quantum Efficiency (%) |
|---|---|---|---|---|---|---|---|---|
| Light-emitting Element 8 | 3.0 | 0.046 | 1.2 | (0.56, 0.44) | 900 | 78 | 82 | 30 |

Figure 46:
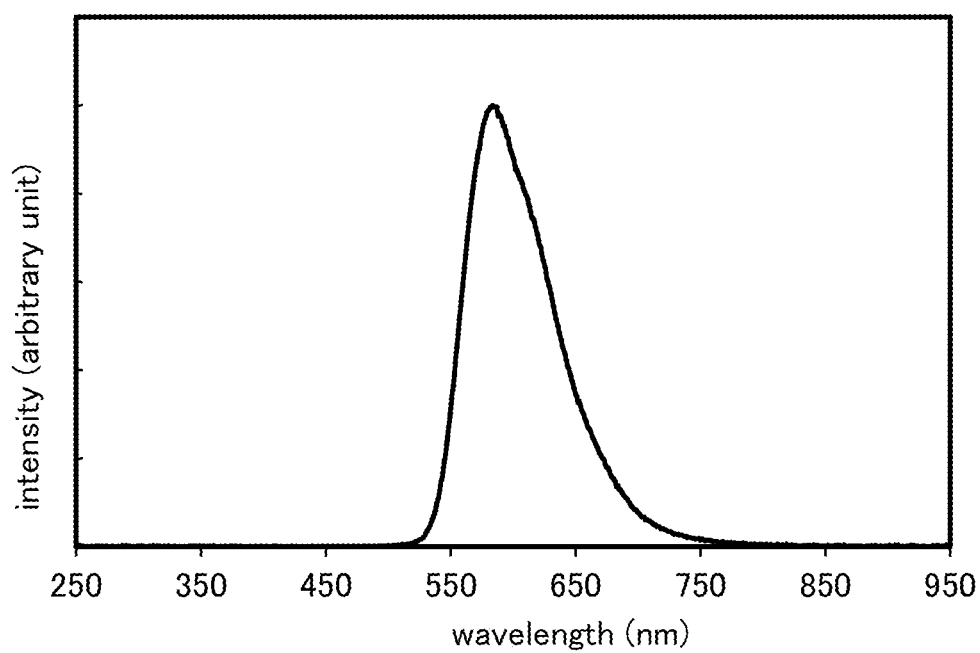
FIG. 46 shows the emission spectrum of the light-emitting element 8.

FIG. 46 shows the emission spectrum of the light-emitting element 8, through which a current flows at a current density of 2.5 mA/cm$^2$. As shown in FIG. 46, the emission spectrum of the light-emitting element 8 has a peak at approximately 584 nm, which is attributed to [Ir(dppm)$_2$(acac)].

Example 10

In this example, a light-emitting element which is one embodiment of the present invention was fabricated and subjected to a preservation test.

In this example, a light-emitting element 1A, a light-emitting element 2A, a comparative light-emitting element 3A, a light-emitting element 4A, and a light-emitting element 8A were fabricated. The structure and fabrication method of the light-emitting element 1A are the same as those of the light-emitting element 1 in Example 5. The structures and fabrication methods of the light-emitting element 2A, the comparative light-emitting element 3A, the light-emitting element 4A, and the light-emitting element 8A are the same as those of the light-emitting element 2 in Example 5, the comparative light-emitting element 3 in Example 5, the light-emitting element 4 in Example 6, and the light-emitting element 8 in Example 9, respectively.

In preservation tests of this example, the light-emitting elements were each preserved in a thermostatic oven maintained at 100° C. for a predetermined time, and the operation characteristics were measured. Note that the operation characteristics were measured at room temperature (in an atmosphere kept at 25° C.) after the light-emitting elements were taken out of the thermostatic oven.

Figure 47:
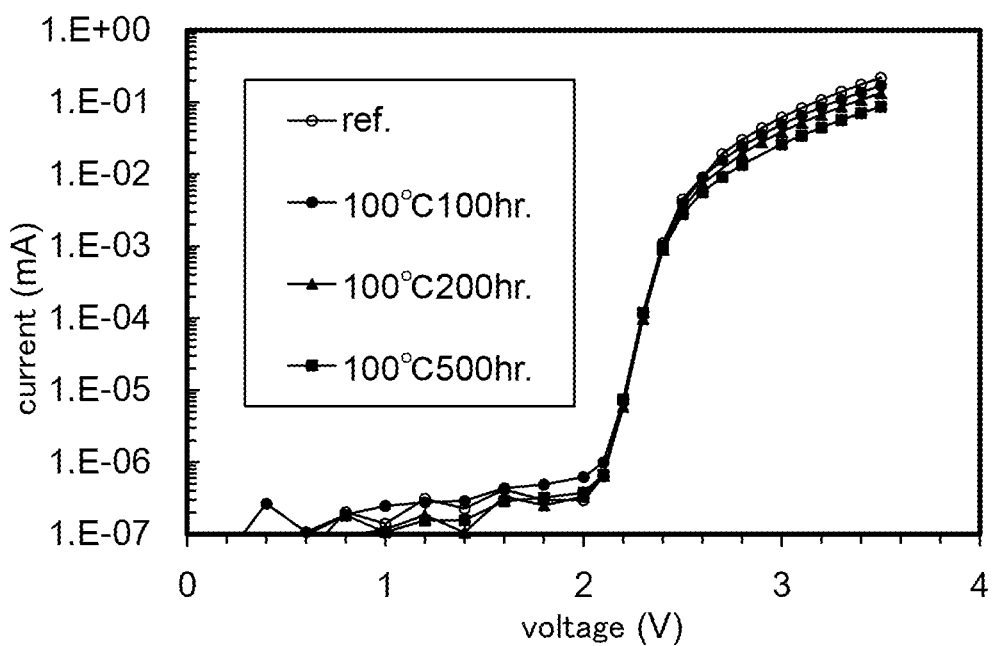
FIG. 47 shows voltage-current characteristics of a light-emitting element 1A after a preservation test.
Figure 48:
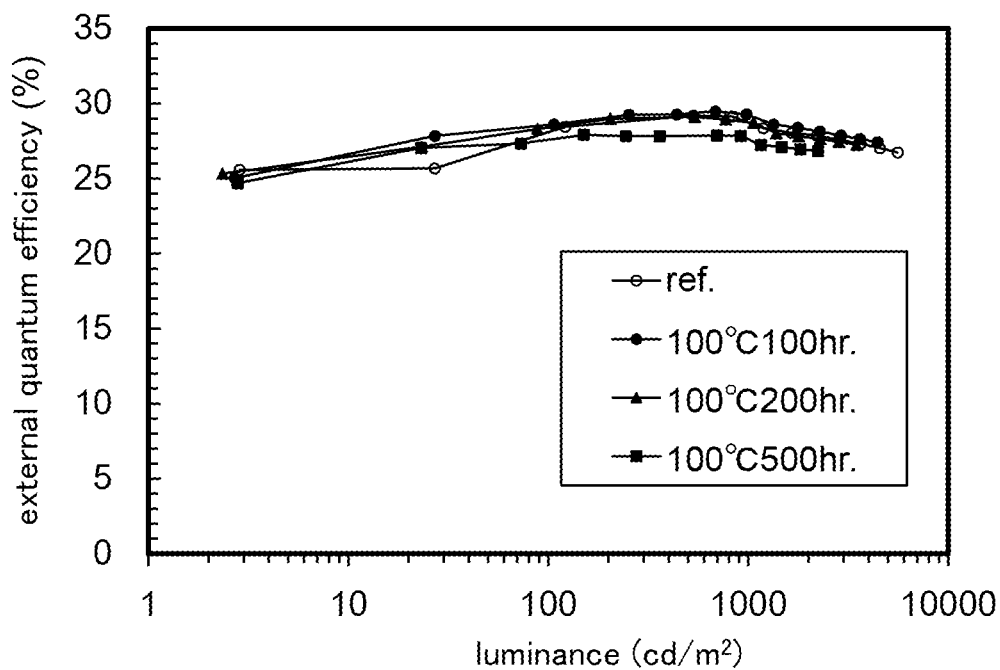
FIG. 48 shows luminance-external quantum efficiency characteristics of the light-emitting element 1A after the preservation test.

FIG. 47 shows voltage-current characteristics and FIG. 48 shows luminance-external quantum efficiency characteristics of the light-emitting element 1A after preservation at 100° C. for a predetermined time. In FIG. 47, the horizontal axis represents voltage (V), and the vertical axis represents current (mA). In FIG. 48, the horizontal axis represents luminance (cd/m$^2$), and the vertical axis represents external quantum efficiency (%).

Figure 49:
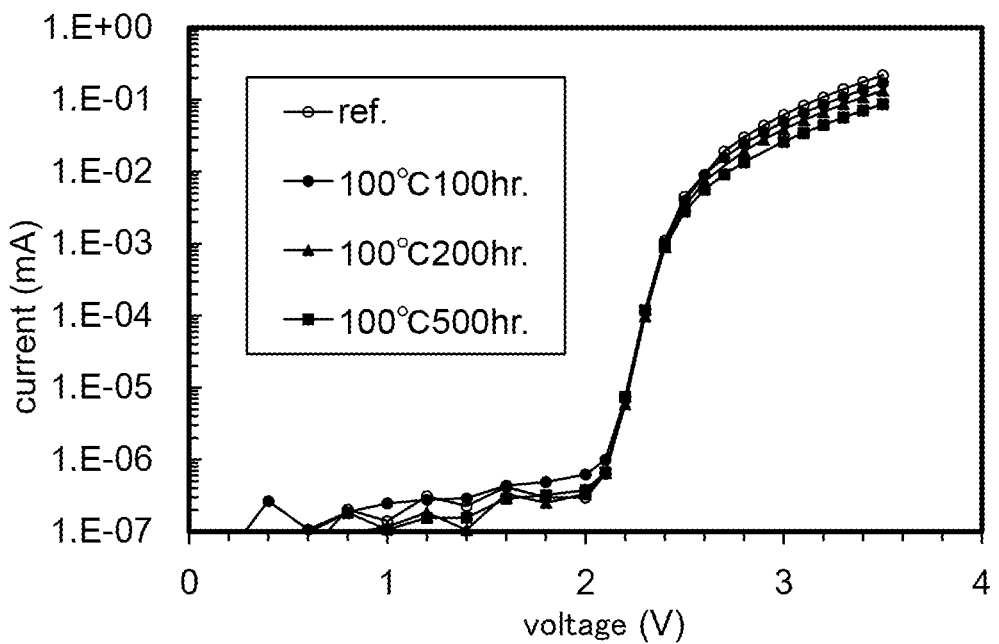
FIG. 49 shows voltage-current characteristics of a light-emitting element 2A after a preservation test.
Figure 50:
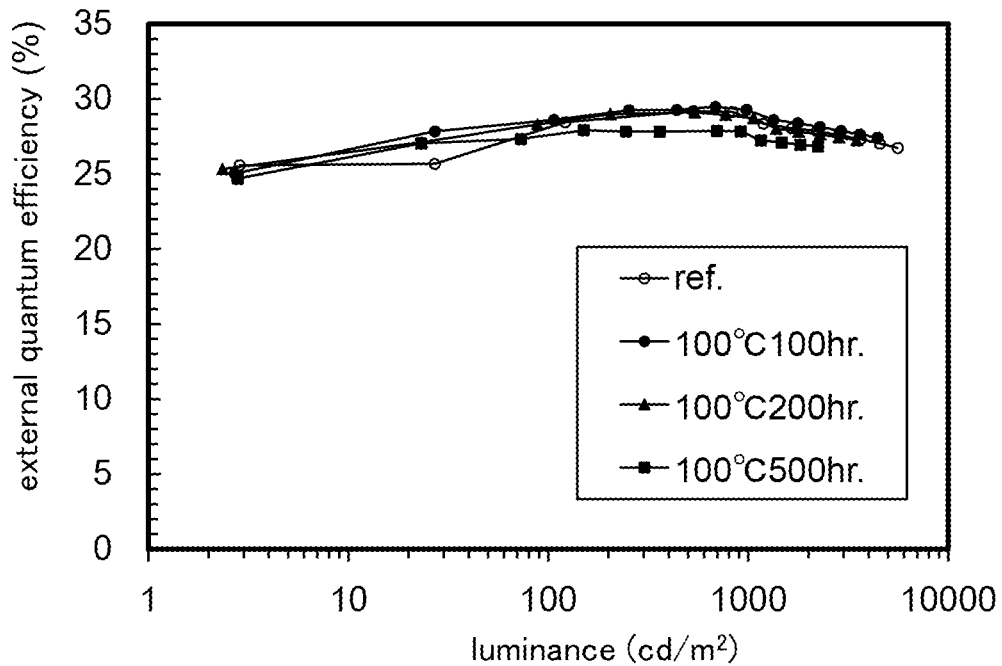
FIG. 50 shows luminance-external quantum efficiency characteristics of the light-emitting element 2A after the preservation test.

FIG. 49 shows voltage-current characteristics and FIG. 50 shows luminance-external quantum efficiency characteristics of the light-emitting element 2A after preservation at 100° C. for a predetermined time. In FIG. 49, the horizontal axis represents voltage (V), and the vertical axis represents current (mA). In FIG. 50, the horizontal axis represents luminance (cd/m$^2$), and the vertical axis represents external quantum efficiency (%).

Figure 51:
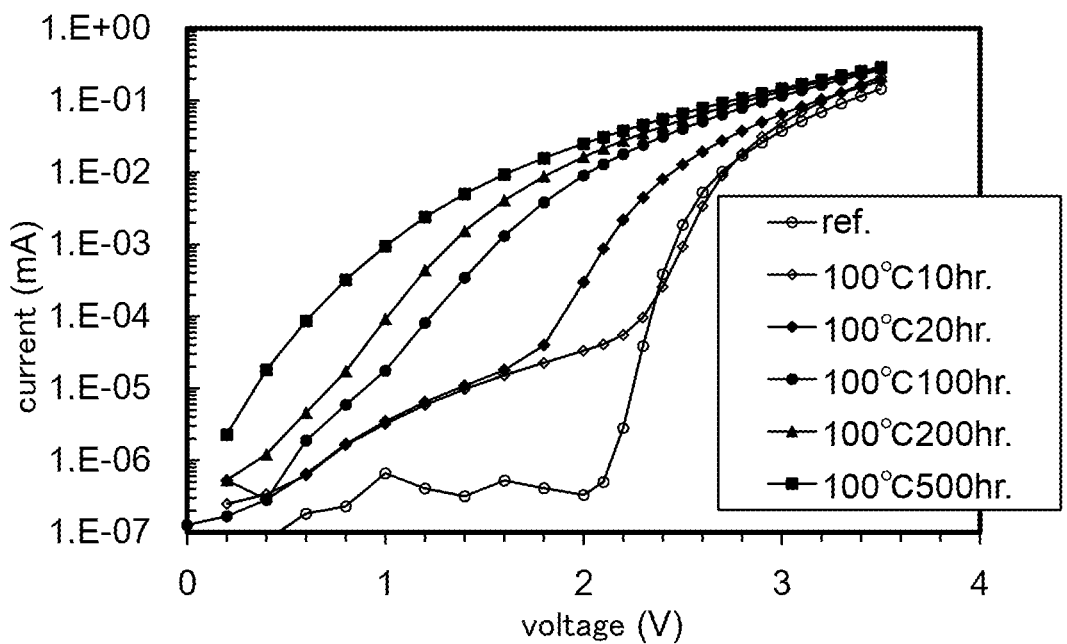
FIG. 51 shows voltage-current characteristics of a comparative light-emitting element 3A after a preservation test.
Figure 52:
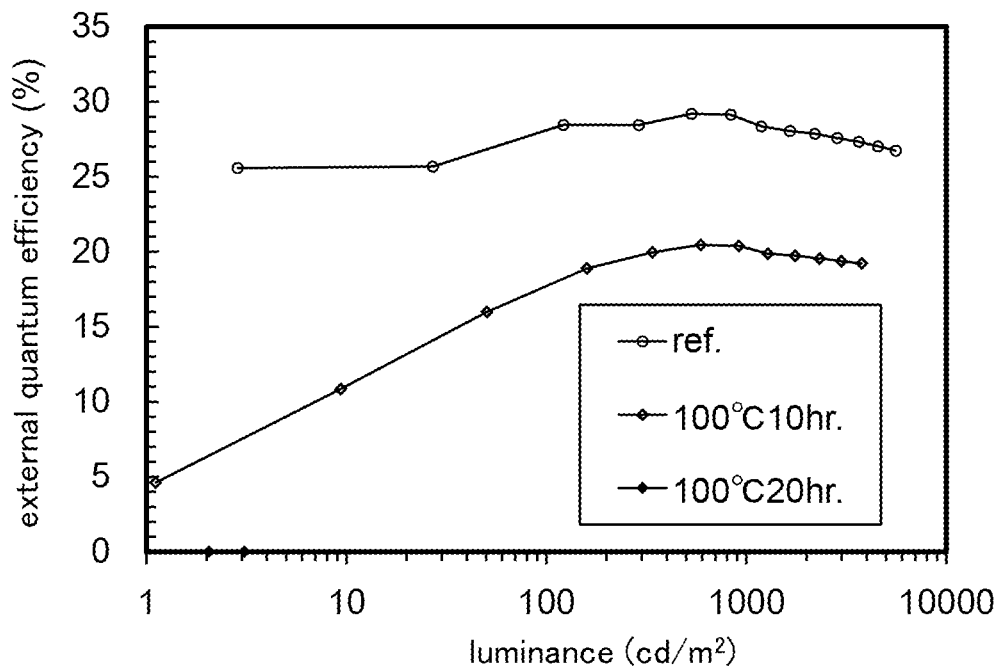
FIG. 52 shows luminance-external quantum efficiency characteristics of the comparative light-emitting element 3A after the preservation test.

FIG. 51 shows voltage-current characteristics and FIG. 52 shows luminance-external quantum efficiency characteristics of the comparative light-emitting element 3A after preservation at 100° C. for a predetermined time. In FIG. 51, the horizontal axis represents voltage (V), and the vertical axis represents current (mA). In FIG. 52, the horizontal axis represents luminance (cd/m$^2$), and the vertical axis represents external quantum efficiency (%). Since light emission could not be observed in the light-emitting element preserved over 20 hours, FIG. 52 does not show data on luminance-external quantum efficiency characteristics after preservation over 20 hours.

Figure 53:
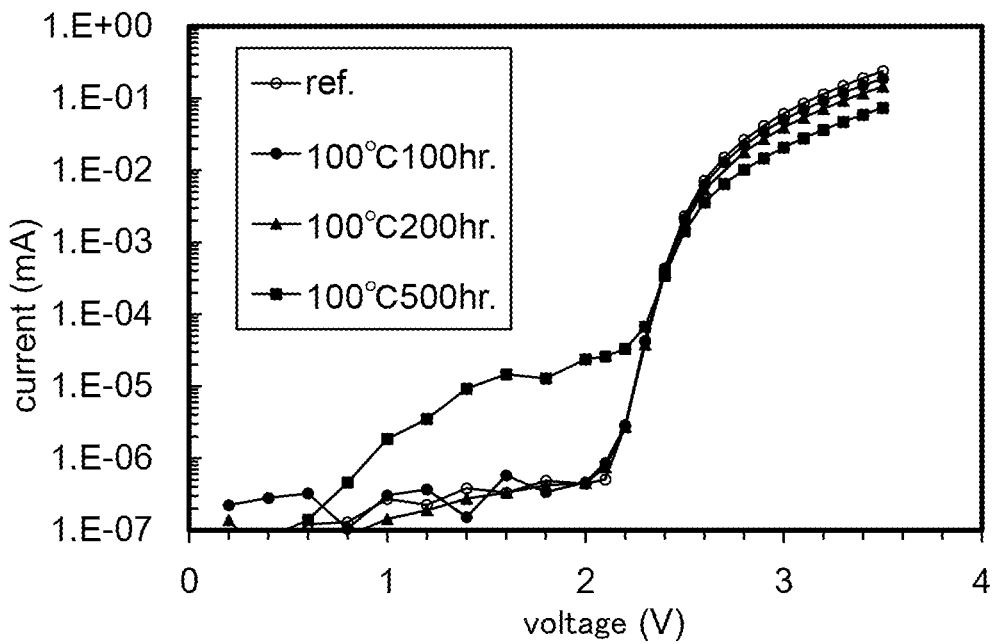
FIG. 53 shows voltage-current characteristics of a light-emitting element 4A after a preservation test.
Figure 54:
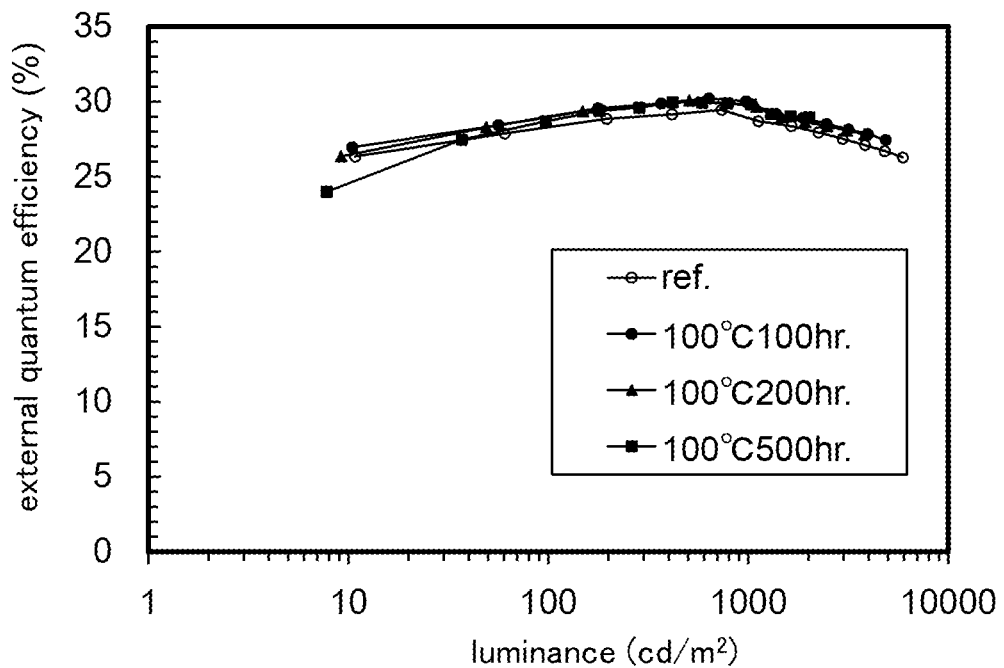
FIG. 54 shows luminance-external quantum efficiency characteristics of the light-emitting element 4A after the preservation test.

FIG. 53 shows voltage-current characteristics and FIG. 54 shows luminance-external quantum efficiency characteristics of the light-emitting element 4A after preservation at 100° C. for a predetermined time. In FIG. 53, the horizontal axis represents voltage (V), and the vertical axis represents current (mA). In FIG. 54, the horizontal axis represents luminance (cd/m$^2$), and the vertical axis represents external quantum efficiency (%).

Figure 55:
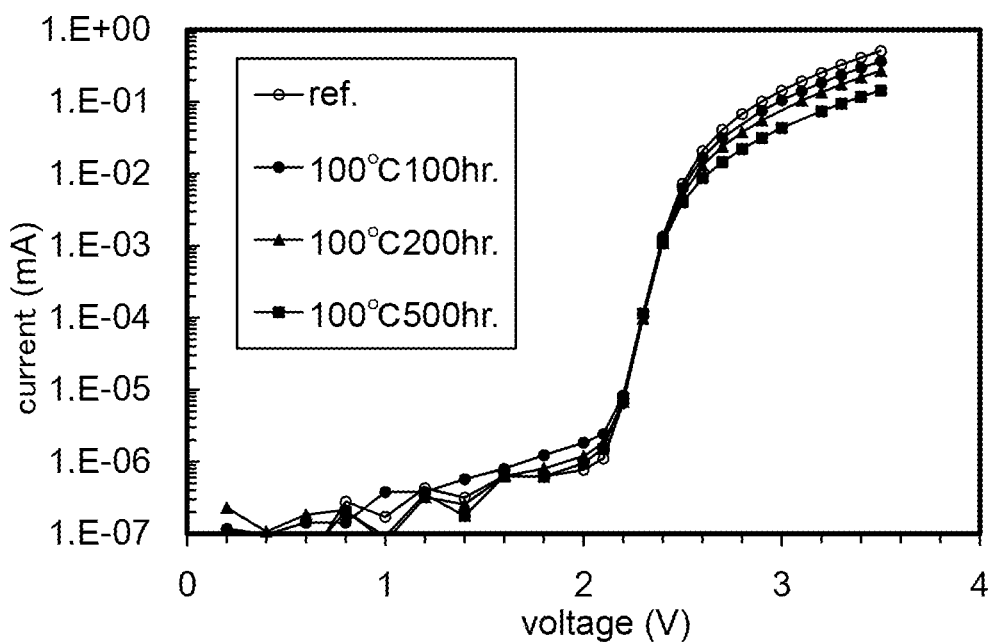
FIG. 55 shows voltage-current characteristics of a light-emitting element 8A after a preservation test.
Figure 56:
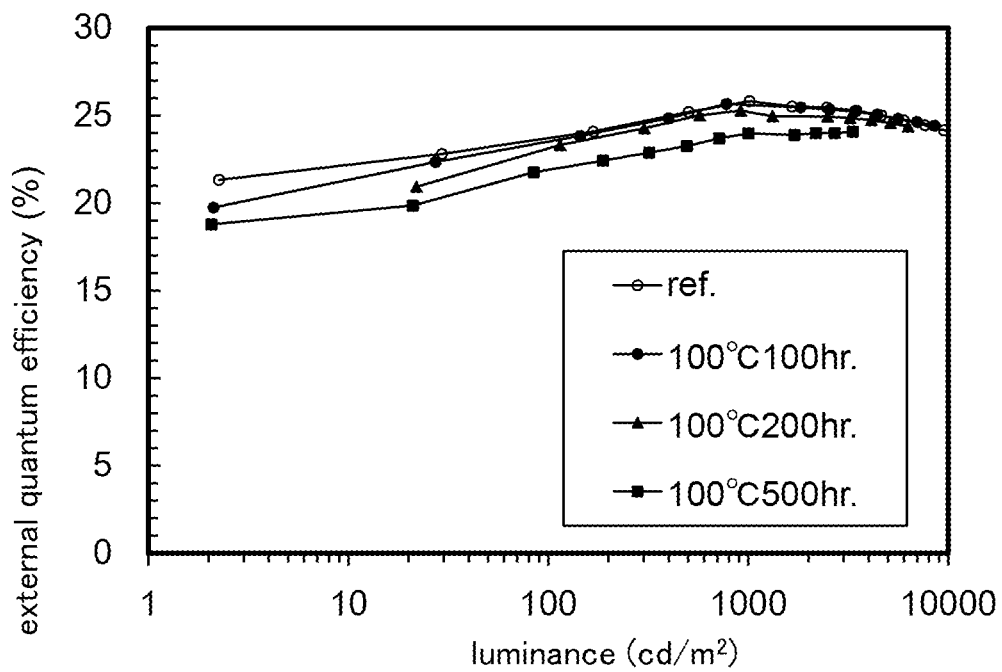
FIG. 56 shows luminance-external quantum efficiency characteristics of the light-emitting element 8A after the preservation test.

FIG. 55 shows voltage-current characteristics and FIG. 56 shows luminance-external quantum efficiency characteristics of the light-emitting element 8A after preservation at 100° C. for a predetermined time. In FIG. 55, the horizontal axis represents voltage (V), and the vertical axis represents current (mA). In FIG. 56, the horizontal axis represents luminance (cd/m$^2$), and the vertical axis represents external quantum efficiency (%).

FIGS. 47 to 50 and FIGS. 53 to 56 show that the light-emitting element 1A, the light-emitting element 2A, the light-emitting element 4A, and the light-emitting element 8A suffered only a small change in voltage-current characteristics and luminance-external quantum efficiency characteristics even after being preserved at 100° C. for 500 hours and that the element characteristics hardly deteriorated through preservation at high temperature. In contrast, FIG. 51 and FIG. 52 show that the comparative light-emitting element 3A suffered a considerable change in voltage-current characteristics and luminance-external quantum efficiency characteristics after being preserved at 100° C. and that the element characteristics deteriorated through preservation at high temperature. As shown in FIG. 51, in the comparative light-emitting element 3A, an initial insulating property is not maintained after 100 hours and leakage current is generated, and FIG. 52 indicates a defect, that is, no light emission of the element. The above results show that heat resistance of a light-emitting element in the case of preservation at high temperature is significantly increased by using a compound which is one embodiment of the present invention.

This application is based on Japanese Patent Application serial no. 2014-151493 filed with Japan Patent Office on Jul. 25, 2014, the entire contents of which are hereby incorporated by reference.

What is claimed is:

1. A light-emitting element comprising:
a light-emitting layer between an anode and a cathode,
wherein the light-emitting layer comprises a first organic compound, a second organic compound, and a phosphorescent compound,
wherein an emission spectrum of a mixed film of the first organic compound and the second organic compound is located on a longer wavelength side than a fluorescence spectrum of a film of the first organic compound and a fluorescence spectrum of a film of the second organic compound,
wherein the first organic compound comprises a 6-membered nitrogen-containing heteroaromatic ring and a carbazole skeleton and does not comprise a triarylamine skeleton,
wherein the 6-membered nitrogen-containing heteroaromatic ring is pyrazine, pyridazine, triazine, or tetrazine,
wherein a HOMO level of the first organic compound is lower than a HOMO level of the second organic compound, and
wherein a difference between the HOMO level of the first organic compound and the HOMO level of the second organic compound is less than or equal to 0.4 eV.

2. A light-emitting element comprising:
a light-emitting layer between an anode and a cathode,
wherein the light-emitting layer comprises a first organic compound, a second organic compound, and a phosphorescent compound,
wherein the first organic compound and the second organic compound form an exciplex,
wherein the first organic compound comprises a 6-membered nitrogen-containing heteroaromatic ring and a carbazole skeleton and does not comprise a triarylamine skeleton,
wherein the 6-membered nitrogen-containing heteroaromatic ring is pyrazine, pyridazine, triazine, or tetrazine,
wherein a HOMO level of the first organic compound is lower than a HOMO level of the second organic compound, and
wherein a difference between the HOMO level of the first organic compound and the HOMO level of the second organic compound is less than or equal to 0.4 eV.

3. A light-emitting element comprising:
a light-emitting layer between an anode and a cathode,
wherein the light-emitting layer comprises a first organic compound, a second organic compound, and a phosphorescent compound,
wherein an emission spectrum of a mixed film of the first organic compound and the second organic compound is located on a longer wavelength side than a fluorescence spectrum of a film of the first organic compound and a fluorescence spectrum of a film of the second organic compound,
wherein the first organic compound comprises a 6-membered nitrogen-containing heteroaromatic ring and a carbazole skeleton and does not comprise a triarylamine skeleton,
wherein a HOMO level of the first organic compound is lower than a HOMO level of the second organic compound,
wherein a difference between the HOMO level of the first organic compound and the HOMO level of the second organic compound is less than or equal to 0.4 eV, and
wherein the 6-membered nitrogen-containing heteroaromatic ring is condensed with a benzene ring.

4. The light-emitting element according to claim 1, wherein the phosphorescent compound comprises iridium.

5. The light-emitting element according to claim 1, wherein the difference between the HOMO level of the first organic compound and the HOMO level of the second organic compound is less than or equal to 0.3 eV.

6. The light-emitting element according to claim 2, wherein the phosphorescent compound comprises iridium.

7. The light-emitting element according to claim 2, wherein the difference between the HOMO level of the first organic compound and the HOMO level of the second organic compound is less than or equal to 0.3 eV.

8. The light-emitting element according to claim 3, wherein the phosphorescent compound comprises iridium.

9. The light-emitting element according to claim 3, wherein the difference between the HOMO level of the first organic compound and the HOMO level of the second organic compound is less than or equal to 0.3 eV.

10. The light-emitting element according to claim 3, wherein the first organic compound and the second organic compound form an exciplex.

11. The light-emitting element according to claim 3, wherein the 6-membered nitrogen-containing heteroaromatic ring is pyridine, pyrazine, pyrimidine, pyridazine, triazine, or tetrazine.

12. The light-emitting element according to claim 3, wherein the 6-membered nitrogen-containing heteroaromatic ring condensed with the benzene ring is quinoline, isoquinoline, dibenzo[f,h]quinoline, naphthyridine, dibenzo[f,h]quinoxaline, op dibenzo[f,h]quinazoline.

13. A light-emitting device comprising the light-emitting element according to claim 1.

14. An electronic device comprising:
the light-emitting device according to claim 13; and
at least one of a connection terminal and an operation key.

15. A light-emitting device comprising the light-emitting element according to claim 2.

16. An electronic device comprising:
the light-emitting device according to claim 15; and
at least one of a connection terminal and an operation key.

17. A light-emitting device comprising the light-emitting element according to claim 3.

18. An electronic device comprising:
the light-emitting device according to claim 17; and
at least one of a connection terminal and an operation key.

* * * * *